United States Patent [19]

Kishimoto et al.

[11] Patent Number: 5,541,088
[45] Date of Patent: Jul. 30, 1996

[54] RECOMBINANT PROCESS OF PRODUCING NON-GLYCOSYLATED B-CELL DEFFERENTIATION FACTOR

[75] Inventors: Tadamitsu Kishimoto, Tondabayashi; Toshio Hirano, Ibaraki; Hiroshi Matsui; Yoshiyuki Takahara, both of Kawasaki; Yukio Akiyama; Akira Okano, both of Kawasaki, all of Japan

[73] Assignees: Ajinomoto Co., Inc., Tokyo; Tadamitsu Kishimoto, Tondabayashi, both of Japan

[21] Appl. No.: 309,612

[22] Filed: Sep. 21, 1994

Related U.S. Application Data

[63] Continuation of Ser. No. 102,499, Aug. 5, 1993, abandoned, which is a continuation of Ser. No. 813,508, Dec. 26, 1991, abandoned, which is a continuation of Ser. No. 81,746, Aug. 5, 1987, abandoned.

[30] Foreign Application Priority Data

| Aug. 6, 1986 | [JP] | Japan | 61-184858 |
| Aug. 27, 1986 | [JP] | Japan | 61-200433 |
| Dec. 18, 1986 | [JP] | Japan | 61-302699 |
| May 13, 1987 | [JP] | Japan | 62-116332 |

[51] Int. Cl.$^6$ .......................... C12N 15/70; C07K 14/54
[52] U.S. Cl. .......................... 435/69.52; 530/351
[58] Field of Search .................. 435/69.5, 69.52, 435/252.31, 252.33; 530/351

[56] References Cited

U.S. PATENT DOCUMENTS

| 4,338,397 | 7/1982 | Gilbert et al. | 435/172.3 |
| 4,559,302 | 12/1985 | Ingolia | 435/172.3 |
| 5,126,325 | 6/1992 | Kishimoto et al. | 514/12 |
| 5,186,931 | 2/1993 | Kishimoto et al. | 424/85.2 |
| 5,324,640 | 6/1994 | Honjo et al. | 435/69.52 |

FOREIGN PATENT DOCUMENTS

| 0220574 | 5/1987 | European Pat. Off. |
| 2063882 | 6/1981 | United Kingdom |
| WO88/00206 | 1/1988 | WIPO |

OTHER PUBLICATIONS

Hirano et al, Nature 324:73–76 (Nov. 1986).
Haegeman et al, Eur. J. Biochem. 159:625–632 (Sep. 1986).
Weissenbach et al, PNAS 77(12):7152–7156 (Dec. 1980).
Copsey et al, *Genetically Engineered Human Therapeutic Drugs*, pp. 13, 445, 471, 475, 479 (Stockton Press, Macmillan 1988).
Database WPI Week 8628, 2 Jun. 1986, Derwent Publications Ltd., London, GB; AN 86–180547 & JP–A–61 115 025 (Chuzo Kishimoto) 2 Jun. 1986 *Abstract*.
Database WPI, Section CH, Week 8541, 2 Sep. 1985, Derwent Publications Ltd., London, GB; C LASS B04, AN 85–253801 & JP–A–60 169 424 (Kishimoto C) 2 Sep. 1985 *Abstract*.
Toshio Hirano et al, Proceeding Of The National Academy Of Sciences Of USA, vol. 82, Aug. 1985, Washington US, pp. 5490–5494.

*Primary Examiner*—Stephen G. Walsh
*Attorney, Agent, or Firm*—Oblon, Spivak, McClelland, Maier & Neustadt, P.C.

[57] ABSTRACT

A purified human B-cell differentiation factor (BCDF) which does not have a natural signal peptide attached to the N-terminal thereof, DNA encoding the BCDF, transformed cells containing such DNA, a process for producing and obtaining the BCDF, and compositions containing the BCDF are disclosed.

1 Claim, 28 Drawing Sheets

P: PstI   A: AluI
M: MvaI   T: TaqI
X: XbaI   S: Sau3AI
D: DraI   H: HhaI

```
GGGGGGGGGGGGGGGGGGGGGAGAGAAGCTCTATCTCCCCTCCAGGAGCCCAGCT ATG  AAC TCC
                                                        1
                                                       (MET) ASN SER 10                      20
TTC TCC ACA AGC GCC TTC TCC CTG GGG CTG CTG CTC CTG GTG TTG CCT GCT
PHE SER THR SER ALA PHE SER LEU GLY LEU LEU LEU LEU VAL LEU PRO ALA 30                       40
GCC TTC CCT GCC CCA GTA CCC CCA GGA GAA GAT TCC AAA GAT GTA GCC CCA CAC AGA CAG
ALA PHE PRO ALA PRO VAL PRO PRO GLY GLU ASP SER LYS ASP VAL ALA PRO HIS ARG GLN 50                       60
CCA CTC ACC TCT GAA CGA ATT GAC AAA CAA ATT CGG TAC ATC CTC GAC GGC ATC TCA GCC
PRO LEU THR SER GLU ARG ILE ASP LYS GLN ILE ARG TYR ILE LEU ASP GLY ILE SER ALA 70                       80
CTG AGA AAG GAG ACA TGT AAC AAG AGT AAC ATG TGT GAA AGC AGC AAA GAG GCA CTG GCA GAA
LEU ARG LYS GLU THR CYS ASN LYS SER ASN MET CYS GLU SER SER LYS GLU ALA LEU ALA GLU 90                      100
AAC AAC CTG AAC CTT CCA AAG ATG GCT GAA AAA GAT GGA TGC TTC CAA TCT GGA TTC AAT GAG
ASN ASN LEU ASN LEU PRO LYS MET ALA GLU LYS ASP GLY CYS PHE GLN SER GLY PHE ASN GLU 110                      120
GAG ACT TGC CTG GTG AAA ATC ATC ACT GGT CTT TTG GAG TTT GAG GTA TAC CTA GAG TAC CTC
GLU THR CYS LEU VAL LYS ILE ILE THR GLY LEU LEU GLU PHE GLU VAL TYR LEU GLU TYR LEU
```

FIG. 5A

```
130                            140                                     150
CAG AAC AGA TTT GAG AGT AGT GAG GAA CAA GCC AGA GCT GTG CAG ATG AGT ACA AAA GTC CTG
GLN ASN ARG PHE GLU SER SER GLU GLU GLN ALA ARG ALA VAL GLN MET SER THR LYS VAL LEU
                                         160                            170
ATC CAG TTC CTG CAG AAA AAG GCA AAG AAT CTA GAT GCA ATA ACC ACC CCT GAC CCA ACC ACA
ILE GLN PHE LEU GLN LYS LYS ALA LYS ASN LEU ASP ALA ILE THR THR PRO ASP PRO THR THR
                       180                                     190
AAT GCC AGC CTG CTG ACG AAG CTG CAG CAG GCA CAG AAC CAG TGG CTG CAG GAC ATG ACA ACT CAT
ASN ALA SER LEU LEU THR LYS LEU GLN GLN ALA GLN ASN GLN TRP LEU GLN ASP MET THR THR HIS
                                200                             205
CTC ATT CTG CGC AGC TTT AAG GAG TTC CTG CAG TCC AGC CTG AGG GCT CTT CGG CAA ATG TAG
LEU ILE LEU ARG SER PHE LYS GLU PHE LEU GLN SER SER LEU ARG ALA LEU ARG GLN MET
CATGGGCACCTCAGATTGTTGTTGTTAATGGGCATTCCTCTTCTGGTCAGAAACCTGTCCACTGGGCACAGAACTTATGTTG
TTCTCTATGGAGAACTAAAAGTATGAGCGTTAGGACACTATTTAATTATTTTAATTATTAATATTTAATATGTGAAGCT
GAGTTAATTTATGTAAGTCATATATTTAAGAAGTACCACTTGAAACATTTATGTATTAGTTTTGAAATAATGA
AAGTGGCTATGCAGTTTGAATATCCTTTGTTTCAGAGCCAGATCATTTCTTGGAAAGTGTAGGCTTACCTCAAATAAATGGCT
AACTTATACACATATTTTAAAGAAATATTTATATTGTATTTATATATATGTTTTTATACCAATAAATGGCATTTTA
AAAAATTCAGCAAAAAAAAAAAAAAAAAAAAAAAAAA
```

FIG. 5B

Synthetic DNA (A)

```
                                                            b                                         Met    21
                                                            |                                         |     Ala
         AACTAGTACGCAAGTTCACGTAAAAAGGGTAT|CGATAAGCC                                                    ATG   GCA
         TTGATCATGCGTTCAAGTGCATTTTTCCCATAGCTATTCGG                                                    TAC   CGT
         |_____|                                                         NcoI
         a                               ClaI(Toql)
                                              1 d
                                                                                    |           40
Pro Thr Ser Ser Ser Thr Lys Lys Thr Gln Leu Glu His Leu Leu Leu Asp Leu Gln Met
CCT ACC TCG AGT AGT ACT AAG AAA ACA CAG CTG GAG CAT CTG CTA GAT CTA CAG ATG
GGA TGG AGC TCA TCA TGA TTC TTT TGT GTC GAC CTC GTA GAC GAT GAT CTA GAG GTC
    XhoI    ScaI(RsaI)        PvuII PstI AluI          BglII(Sau3A)
    AvaI                            (AluII)
                  c                              k

60
Ile Leu Asn Gly Ile Asn Asn Tyr Lys Asn Pro Lys Leu Thr Arg Met Leu Thr Phe Lys Phe Tyr
ATT TTG AAG GGA ATT AAT AAT TAC AAG AAT CCC AAG CTT ACG CGT ATG TTA ACA TTT AAA TTT TAC
TAA AAC TTA CCT TAA TTA TTA ATG TTC TTA GGG TTC GAA TGC GCA TAC AAT TGT AAA TTT AAA ATG
                                          HinfI HindIII MluI   HpaI    DraI
                                                         i
                                     e
```

FIG. 8A

○ Human Ala-BCDF (57 ng/ml)
● Human BCDF (79 ng/ml)
★ Human BCDF (STANDARD)(100 u/ml)
--- Human BCDF NOT ADDED

RECOMBINANT PROCESS OF PRODUCING NON-GLYCOSYLATED B-CELL DEFFERENTIATION FACTOR

This application is a continuation of application Ser. No. 08/102,499, filed on Aug. 5, 1993, now abandoned, which is a continuation of Ser. No. 07/813,508, filed Dec. 26, 1991, now abandoned, which is a continuation of Ser. No. 07/081,746, filed Aug. 5, 1987, all now abandoned.

BACKGROUND OF THE INVENTION

1. Field of the Invention:

The present invention relates to B cell differentiation factor (hereafter referred to as "BCDF") having activity in humans, a gene corresponding to human BCDF polypeptide, biotic cells having incorporated therein the gene, a method for production of the BCDF using the biotic cells as well as an immunotherapeutic composition comprising human BCDF as an effective component.

2. Description of the Related Art:

Mature human BCDF is a material that was first discovered as a discrete substance by the present invention. It can be widely utilized as a therapeutic composition for immunodeficiency diseases.

European Patent Application 0220574 describes certain so-called interferons having an amino acid sequence related to BCDF of this invention. However, the protein disclosed in EP 0220574 is longer than mature human BCDF, and contains at least a signal peptide attached thereto. The structure of mature human BCDF was not appreciated before the present invention. Also in contrast to the polypeptide of EP 0220574, the present polypeptides do not have the anti-viral activity described in EP 0220574.

Mature B cells activated by stimulation with an antigen are caused to proliferate by the aid of T cells, but it is known that one or more T cell-derived differentiation-inducing substances are necessary to finally differentiate B cells to reach antibody-producing cells. The presence of such substances has been substantiated by R. W. Dutton et al., Transplant. Rev., 23, 66 (1975) and, A. Schimpl and E. Wecker et al., Nature N. Biol., 237, 15 (1972). They have found that the supernatant after culturing a mouse lymphocyte mixture or the supernatant after culturing mouse lymphocytes stimulated with an antigen or mitogen can amplify a primary immune response of mouse lymphocyte mass from which mouse T cells are removed or of nude mouse-derived lymphocytes to sheep red blood cells and have given the name of T cell replacing factor, namely TRF, to the active substance having such an activity. Since then, TRF has been defined to be a humoral factor which acts on B cells in such a manner that does not require any consistency in major histocompatibility gene complex (hereafter simply referred to as MHC) non-specifically to antigen, does not induce proliferation of B cells but induces differentiation of B cells to antibody-producing cells.

After that, functional evidence showing the presence of such a B cell differentiation factor has been accumulated and the presence of a human differentiation factor analogous to the one in mice has been suggested. At present, the factor defined as described above that differentiates B cells into antibody-producing cells has been collectively termed BCDF.

As such, BCDF plays an important role in the function of antibody production of B cells in vivo in humans.

Lymphokines, which are soluble proteins having biological and pharmacological activity, act to regulate immune response mechanisms of the body in vivo in a trace amount. The utility of lymphokines as anti-tumor agents, an anti-viral agents, anti-bacterial agents, immunodeficiency therapeutic agents and autoimmune disease therapeutic agents has been expected due to the nature of these immunoactive substances (Adv. in Immunopharm., 507, 1980). BCDF in accordance with the present invention is a lymphokine and, from this point of view, BCDF is expected to be applicable as a medical drug.

To obtain BCDF, there has been hitherto adopted a method which comprises separating normal T cells from human peripheral blood and stimulating the T cells with mitogen to produce BCDF. According to this method, many problems arise in that it is difficult to obtain T cells in a sufficient amount; toxic mitogens harmful to BCDF contaminate because mitogens are used and it is difficult to remove them; it is necessary to supplement serum components such as fetal bovine serum, etc. in culture of T cells and BCDF cannot be sufficiently separated from these supplemented proteins so that failure to give pure BCDF becomes an obstacle to medical use of BCDF;BCDF could not thus be produced industrially. There is also reported a method which comprises cell fusion of human T cells with human cancer cells to give human T cell hybridomas and producing BCDF using the hybridomas (Okada et al., J. Exp. Med., 157, 583 (1983)). However, human hybridomas often tend to reduce their lymphokine productivity during culture, so BCDF-producing human hybridomas that withstand practical use are still unknown.

SUMMARY OF THE INVENTION

Therefore, an object of the present invention is to provide a human BCDF, DNA coding for the BCDF, biotic cells having such DNA and a method for producing such BCDF. DNA coding for human BCDF is necessary and indispensable for production of human BCDF by cells of procaryotes or eucaryotes in large quantities.

BRIEF DESCRIPTION OF DRAWINGS

In the drawings attached

FIG. 5 shows the (nucleotide sequence) and amino acid sequence of BCDF.

FIG. 15 also illustrates antibody production by the addition of human BCDF in combination with human IL-2.

DETAILED DESCRIPTION OF THE PREFERRED EMBODIMENTS

Figure 1:
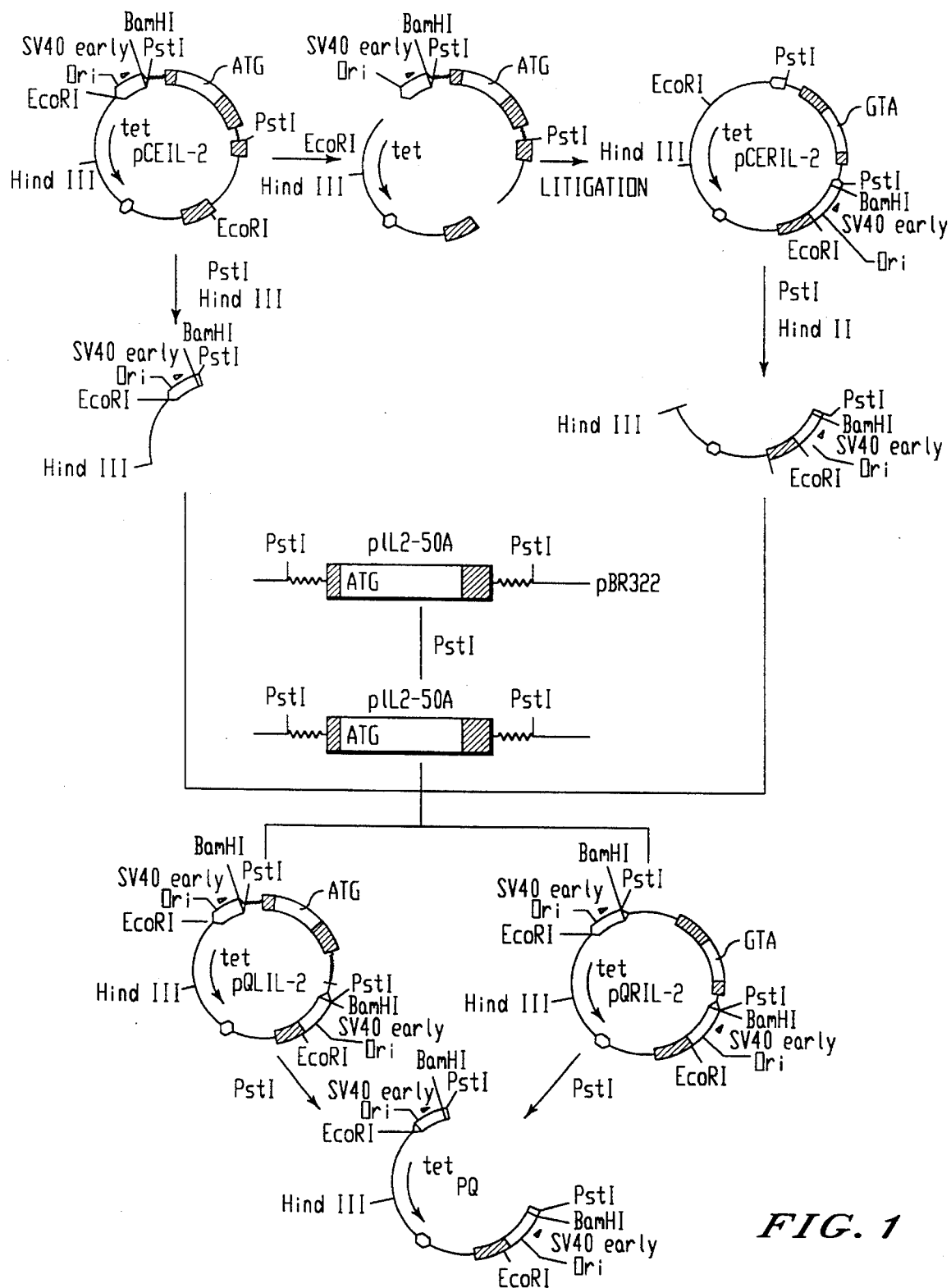
FIG. 1 shows the construction of expression recombinant DNA in monkey cells.

The present inventors have already discovered that human T cells transformed by human T cell leukemia virus (hereafter referred to as "HTLV") can produce BCDF with high efficiency and obtained an authentic protein having a B cell differentiation factor activity of $5 \times 10^6$ units/ml or more.

Production of a human BCDF-producing human T cell line can be carried out as follows. Lymphocytes are separated from human peripheral blood, tonsil, core blood, etc. according to the density gradient centrifugal method, etc. using Ficoll pack, etc. and, human T cells are transformed using HTLV in a manner similar to N. Yamamoto, Science, 217, 737 (1982).

For example, the following method can be used: $1 \times 10^7$/ml of virus-producing cell line MT-2, which is inactivated by irradiation of X rays (12000 to 14000 rads) and $1 \times 10^7$/ml human lymphocytes, which are separated by the above-mentioned method are mixed and inoculated on RPMI 1640 medium containing 20% FCS, 100 µg/ml of kanamycin, 2 µg/ml of $NaHCO_3$ and 25 mM N-2-hydroxyethylpiperazine-N'-2-ethanesulfonic acid (HEPES), in a plastic Petri's dish (Falcon #3003), followed by culturing at 37° C. in the presence of 5% $CO_2$. After culturing for 2 to 3 months while replenishing a fresh medium for half of the medium twice a week, the cell line is established by the limiting dilution method. A BCDF activity of the supernatant of the established cell is measured to obtain a cell line having the BCDF activity.

As the cells established by this method, for example, a human T cell line named VT-1(IFO 50096) can be used. There are no particular conditions for growing VT-1 but culture conditions conventionally used may be appropriately adopted. BCDF can also be produced in a conventional manner but it is preferred to perform the production in a protein-free medium.

As a medium most suited for enhancing the growth of VT-1, there is used a medium supplemented with, for example, 1 to 30%, preferably 20% of FCS. A medium most suited for the production of BCDF may be the aforesaid FCS-free medium. The survival rate of VT-1 is maintained 70% or more even after culturing 48 hours in a FCS-free complete synthetic medium.

In the case where BCDF is produced from T cells, it was essentially required in the prior art to supplement protein such as FCS or mitogen to media (cf., T. Teranishi et al., J. Immunol., 128, 1093 (1982), A. Muraguchi et al., J. Immunol., 127, 412 (1981)). To the contrary, in the case where human BCDF is produced using VT-1, it is .notable that it is neither necessary to supplement serum such as FCS, protein components in blood and other proteinaceous components to media nor necessary to supplement even mitogen to T cells or B cells. Therefore, not only can BCDF be produced at low costs without using expensive FCS but also safe BCDF free from heterogeneous proteins or mitogen harmful to the human body can easily be obtained.

The aforesaid method for producing BCDF using VT-1 can be performed under various environmental conditions. However, the VT-1 culture should be preferably maintained in moisture controlled air containing approximately 5 to 10% of carbon dioxide in a temperature range of approximately 35° to 38° C. Further, the pH of the medium should ideally be maintained under slightly alkaline conditions of approximately 7.0 to 7.4. VT-1 is inoculated on various types of incubators such as a round bottom microplate, etc. in various volumes such as 100 µl, etc. Tissue culture flasks such as Flask No. 3013 or No. 3024 marketed from Falcon Labware, Div. Becton, Dickinson and Co. can also be used. As another method, roller bottles such as Bottle No. 3027 marketed from the aforesaid Falcon Labware can also be used as incubators.

An initial density of the cells for the optimum conditions for culturing VT-1 and growing the cell count is $1 \times 10^4$ to $5 \times 10^5$ preferably $2 \times 10^5$. When VT-1 is cultured under the conditions described above, the cell density increases from approximately $5 \times 10^5$ to $2 \times 10^6$ per 1 ml of the medium, generally after 2 to 7 days and therefore, a fresh medium is again replenished to reduce the cell density to $1 \times 10^4$ to $5 \times 10^5$ per 1 ml of the medium and the incubation is again continued. After continuing the incubation of VT-1 to reach the desired cell number as above, the cells are separated by centrifugation, etc. After the cells are rinsed with a protein-free complete synthetic medium, they are inoculated on a fresh complete synthetic medium. In this case, it is preferred that the initial density of the cells is approximately $1 \times 10^4$ to $1 \times 10^7$ per 1 ml of the medium, ideally $1 \times 10^6$ cells per 1 ml of the medium.

The quantity of BCDF produced by culturing VT-1 varies with passage of time. When VT-1 is cultured in RPMI 1640 medium (containing 100 units/ml of penicillin, 100 µg/ml of streptomycin, 10 µg/ml of gentamycin and 16 mM of $NaHCO_3$), for example, in an initial cell density of $1 \times 10^6$/ml, the BCDF activity reaches its peak level after 48 hours. Further, the BCDF activity present for a subsequent 24 hours decreases slightly. As such, the optimum incubation time for producing BCDF by VT-1 in RPMI 1640 medium is approximately 24 to 78 hours.

BCDF can be concentrated and purified from the aforesaid culture supernatant by various methods such as salting out, lyophilization, ultrafiltration, gel filtration chromatography, ion exchange chromatography, affinity chromatography, chromatofocusing, reversed phase chromatography, focusing electrophoresis, gel electrophoresis, etc.

Turning next to measurement of the BCDF activity, the following methods may be mentioned.

BCDF activity is measured using human B cell line CL4 producing IgM in response to human BCDF (T. Hirano et al., Proc. Natl. Acad. Sci., 82, 5490 (1985)). A sample solution for assaying a BCDF activity and $6 \times 10^3$ cells of CL4 are added to 200 µl of 10% FCS-containing RPMI 1640 medium (containing 100 units/ml of penicillin, 100 µg/ml of streptomycin, 10 µg/ml of gentamycin and 16 mM of $NaHCO_3$). The mixture is cultured at 37° C. for 3 days in the presence of 5% $CO_2$ in a 96 well microplate, whereby the amount of IgM in the supernatant is measured by enzyme immunoassay. Under these conditions, the activity of BCDF showing 50% of the maximum IgM production amount (the highest CL4 reaction) is defined to be 1 U/ml.

The BCDF activity can also be measured by the reverse PFC method using human B cell line CL4 producing IgM in response to human BCDF (O. Saiki et al., Eur. J. Immunol., 13, 31 (1983)). A sample solution for assaying a BCDF activity and $1 \times 10^4$ cells of CL4 are added to 200 µl of 10% FCS-containing RPMI 1640 medium (additives are the same as described above). The mixture is cultured at 37° C. for 3 days in the presence of 5% $CO_2$ in a 96 well microplate. The culture cells, complement, anti-human IgM antibody and protein A-bound sheep red blood cells are mixed with agarose dissolved in Hanks' solution and the mixture is spread and solidified on a Petri's dish. After culturing overnight at 37° C. in the presence of 5% $CO_2$, the number of cells differentiated into IgM-producing cells by the action of BCDF is measured by the number of hemolytic plaques formed.

To identify and collect the gene coding for human BCDF, RNA is extracted and harvested from the VT-1 cells cultured under the optimum conditions for the production of BCDF described above to make a cDNA library and cDNA coding for BCDF is cloned from the library. Therefore, the present inventors have identified BCDF cDNA as will be later shown in the examples by completely purifying human BCDF produced by the VT-1 cells, determining the amino acid sequence of BCDF at the N-terminal thereof, and the amino acid partial sequence of the fragment peptides which are obtained by restricted fragmentation of lysyl endopeptidase, synthesizing oligonucleotides corresponding to the respective peptides, and screening clones complementarily hybridized with some synthetic probes from the aforesaid cDNA library using the thus synthesized oligonucleotide probes. The base sequence of the thus obtained cDNA has been determined in a conventional manner and the gene coding for BCDF has been established. From the sequence of this gene, it has been found that human BCDF is a polypeptide composed of 184 amino acids. At the same time, in order to express the thus obtained cDNA in eucaryotic cells, the cDNA has been connected with an expression vector and its gene has been introduced into the cells. BCDF is allowed to be produced in the supernatant by incubation of the cells, and pure human BCDF is obtained by purification operations. Recombinant human BCDF corresponding to the genetic structure of BCDF has also been produced, and it has been found that this BCDF has the same physicochemical and biological properties as those of the VT-1 cells or human BCDF obtained from human cells. From the foregoing, it has been finally proven that the identified gene does code for human BCDF protein.

On the other hand, human BCDF can also be produced in procaryotes. Namely, the gene coding for human BCDF is introduced into vector DNA to express the same, the thus obtained recombinant DNA is introduced in a procaryotic host and the obtained transformed microorganism is cultured.

The gene coding for BCDF has at least amino acid sequence (I) or (II) (see below) or the base sequence corresponding to its partially modified structure. Host cells of the procaryote in which the recombinant DNA is introduced may be *Escherichia coli, Bacillus subtilis* and other microorganisms, which are obvious to one skilled in the field of current genetic engineering.

Media and methods for culturing the transformed microorganisms (procaryotes) may be conventional media and methods.

In the case where human BCDF is accumulated in the transformed microorganism, BCDF can be recovered and purified by a method which one skilled in the art can readily perform. Simply stated, the cells are collected by centrifugation after incubation and suspended in a solution containing lysozyme or a solution containing a detergent; after completion of the reaction, freezing and thawing are repeated to obtain the cell extract and the extract can be purified by the aforesaid purification method and/or in a simple manner such as affinity chromatography using an anti-BCDF antibody-immobilized column.

At this time, however, there is no report on a method for producing BCDF by procaryotes such as *Escherichia coli,* etc. namely, a method for producing BCDF by procaryotes which comprises incorporating DNA corresponding to BCDF into a procaryotic vector, replicating, transcribing and translating in the procaryotic cells, and BCDF produced by such a method.

As a result of further extensive investigations to solve the foregoing problems, the present inventors have accomplished the present invention by culturing procaryotic cells transformed by recombinant DNA composed of vector DNA capable of replicating the gene coding for the polypeptide having human BCDF activity and procaryotic cells and harvesting the produced human BCDF. Hereafter this invention will be described in detail.

The present inventors have already identified a gene coding for human BCDF, paying attention to the fact that VT-1 cells (IFO 50096) or a human T cell transformed by HTLV (human T cells leukemia virus) produce human BCDF in large quantities (Japanese Patent Application No. 184858/86).

Details of the cloning procedure of the gene coding for human BCDF are described in the example given later.

Turning now to production of the procaryote producing human BCDF, the gene coding for human BCDF is incorporated into vector DNA capable of replicating in procaryotic cells. In this case, DNA coding for human BCDF may be inserted downstream from the promoter sequence of the expression vector; alternatively, a DNA fragment having the promoter sequence may be inserted before or after the insertion of cDNA of the expression vector and upstream from the DNA coding for human BCDF. In this case, cDNA coding for human BCDF codes for a polypeptide composed of 212 amino acids as shown in FIG. 5, but the hydrophobic N-terminal region corresponding to 28 amino acids of this polypeptide is a signal sequence, which is cleaved during the course of secretion. Accordingly, it is desired to express the cDNA portion coding for mature human BCDF polypeptide composed of 184 amino acids starting from the N-terminal Pro.

To construct the expression plasmid, the vector is cleaved with an appropriate restriction enzyme and if necessary and desired, inserted with an appropriate linker or an oligonucleotide adapter capable of annealing when combined. The thus finished double stranded DNA is mixed with vector DNA, and the mixture is ligated using ligase.

The thus obtained recombinant DNA is introduced in a procaryotic host and a human BCDF-producing strain can be selected from the obtained transformed microorganisms.

As the procaryote in the present invention, *Escherichia coli, Bacillus subtilis*, etc. can be employed; it is preferred to use *Escherichia coli*.

Examples of the vectors for *Escherichia coli* which can be used in the present invention include EK type plasmid vectors (stringent type; pSC101, pRK353, pRK646, pRK248, pDF41, etc.), EK type plasmid vectors (relaxed type: ColE1, pVH51, pAC105, RSF2124, pCR1, pMB9, pBR313, pBR322, pBR324, pBR325, pBR327, pBR328, pKY2289, pKY2700, pKN80, pKC7, pKB158, pMK 2004, pACYC1, pACYC184, dul, etc.), λgt type phase vectors: λgt.λc, λgt.λB, λWES, λC, λWES, λB, λZJvir., λB', λALO, λB, λWES.Ts622, λDam, etc.

Further as the promoters, all promoters that function in *Escherichia coli*, including trp, lac, tac, tufB, B-lactamase and lpp promoter, may be used.

For the transformation of host cells using recombinant DNA, the following method is conventionally used. In the case where a procaryote such as *Escherichia coli* is a host, competent cells capable of incorporating this DNA can be transformed by the well known $CaCl_2$ method, after recovering cells in exponential growth phase. Presence of $MgCl_2$ or RbCl in the transformation reaction solution improves the transformation efficiency. It is also possible to perform the transformation after preparation of protoplast of the host cell.

The thus obtained recombinant procaryote cell in which the human BCDF gene has been incorporated may be cultured in a conventional manner.

The thus obtained BCDF can be concentrated and purified from the aforesaid culture supernatant by various methods such as salting out, lyophilization, ultrafiltration, gel filtration chromatography, ion exchange chromatography, affinity chromatography, chromatofocusing, reverse phase chromatography, focusing electrophoresis, gel electrophoresis, etc.

In case the human BCDF is accumulated in the transformed microorganism, BCDF can be recovered and purified by conventional methods. Simply stated, the cells are collected by centrifugation after incubation and suspended in a solution containing lysozyme or a solution containing a detergent; after completion of the reaction, freezing and thawing are repeated to collect the cell extract and the extract can be purified by the aforesaid purification method and/or in a simple manner such as affinity chromatography using anti-BCDF antibody-immobilized column.

Turning next to measurement of the BCDF activity, the following methods may be mentioned.

The BCDF activity is measured using human B cell line CL4 producing IgM in response to human BCDF (T. Hirano et al., Proc. Natl. Acad. Sci., 82, 5490 (1985)). A sample solution for assaying a BCDF activity and $6×10^3$ cells of CL4 are added to 200 μl of 10% FCS-containing RPMI 1640 medium (containing 100 units/ml of penicillin, 100 μg/ml of streptomycin, 10 μg/ml of gentamycin and 16 mM of $NaHCO_3$). The mixture is cultured at 37° C. for 3 days in the presence of 5% $CO_2$ in a 96 well microplate, whereby the amount of IgM in the supernatant is measured by enzyme immunoassay. Under these conditions, the activity of BCDF showing 50% of the maximum IgM production amount (the highest CL4 reaction) is defined to be 1 U/ml.

The BCDF activity can also be measured by the reverse PFC method using human B cell line CL4 producing IgM in response to human BCDF (O. Saiki et al., Eur. J. Immunol., 13, 31 (1983)). A sample solution for assaying a BCDF activity and $1×10^4$ cells of CL4 are added to 200 μl of 10% FCS-containing 1640 medium (additives are the same as described above). The mixture is cultured at 37° C. for 3 days in the presence of 5% $CO_2$ in a 96 well microplate. The culture cells, complement, anti-human IgM antibody and protein A-bound sheep red blood cells are mixed with agarose dissolved in a Hanks' solution and the mixture is spread and solidified on a Petri's dish. After culturing overnight at 37° C. in the presence of 5% $CO_2$, the number of cells differentiated into IgM-producing cells by the action of BCDF is measured by the number of hemolytic plaques formed.

As is also known with human interferon genes, eucaryotic genes show polymorphism (Taniguchi et al., Gene, 10, 11–15 (1980), Ohno and Taniguchi, Proc. Natl. Acad. Sci., USA, 77, 5305–5309 (1981), Gray et al., Nature, 295, 501–508 (1981)). As a result of polymorphism, some amino acids of the protein product may be replaced in some cases and other cases, nothing changes even though base sequences may change. Accordingly, the present invention also includes polypeptide obtained by replacing one or more amino acids for one or more amino acids in the amino acid sequence of FIG. 5 and DNA coding for this polypeptide, as long as they possess the human BCDF activity. For example, a cysteine residue may be replaced by a neutral amino acid, if the cysteine residue which is replaced is not required for BCDF activity. Further as will be shown in the examples, the present invention also includes polypeptide having human BCDF activity deficient in one or more amino acids, polypeptides having added thereto one or more amino acids, polypeptides having combined sequences thereof (including replacement with amino acids) and DNAs having base sequences coding for these polypeptides. Even though there is a modified region having a supplemental amino acid sequence that inhibits the polypeptide function as human BCDF, such can be utilized as the polypeptide and gene of the present invention insofar as the newly added region can be readily removed. Namely, any polypeptide having human BCDF activity is as described in this application human BCDF in accordance with the present invention.

Application of the thus produced BCDF to the clinical field is roughly classified into three areas. First, anti-BCDF antibody is produced by BCDF; the antibody can be used for analysis of immunological state using the immunoassay system of BCDF with BCDF and anti-BCDF antibody and at the same time, can be used for repair of functional abnormality of B cells sometimes noted in autoimmune diseases. Second, another application is to therapy for various diseases. For example, the antibody-producing function can be made normal by administrating BCDF alone or together with other lymphokines or immunotherapeutic agents, in patients with immunodeficiency due to reduced antibody producing activity of B cells accompanied by reduced helper function of T cells.

Further noting the differentiation activity of BCDF, BCDF can also be used as an anti-malignant tumor agent by differentiating malignant tumor cell lines by BCDF and causing growth inhibition.

As still a further application of BCDF, the following is considered. It is reported that normal B cells can be cultured over a long period of time by supplementing B cell growth factor (BCGF) (K. Yoshizaki et al., J. Immunol., 130, 1241 (1983)) and other T cell factors including lymphokines to media (cf. B. Sredni et al., J. Exp. Med., 154, 1500 (1981)). By allowing BCDF to act on these normal B cells cultured or B cells transformed by EB virus in an appropriate period of time, antibody can be produced in vitro. By cloning B cells producing antibody which recognizes a specific antigen present on the surface of, for example, pathogenic bacteria, pathogenic virus, pathogenic protozoa, cancer cells, etc. to monoclone and culturing the cloned normal B cells or the cells transformed by EB virus in combination with BCDF and other lymphokines, useful monoclonal antibodies can be produced. These antibodies can be utilized for therapy and diagnosis of infectious diseases and cancers.

As described above, BCDF is a substance effective over an extremely wide range.

The present invention also relates to an immunotherapeutic composition effective for therapy of primary and secondary immunodeficiencies, infectious diseases with bacteria, fungi, viruses, protozoa, etc., cancers and for augmentation of haemopoietic function. More particularly, the present invention relates to an immunotherapeutic composition comprising human BCDF as an effective component.

As such, BCDF plays an important role in the function of antibody production of B cells in vivo in humans. With respect to human BCDF playing such an important role, the present inventors have made extensive investigations and succeeded in determination of its DNA sequence and amino acid sequence (Japanese Patent Application Nos. 184858/86 and 200433/86) and in production of human BCDF using *Escherichia coli* (Japanese Patent Application No. 302699/86).

However, no report has been hitherto made on pharmacological effects of this human BCDF against cancer, infectious diseases, primary immunodeficiency or secondary immunodeficiency, for example, reduction in the number of leucocytes observed upon chemotherapy, and radiation treatment of patients with malignant tumors.

Now, cancers, immunodeficiency and infectious diseases in association therewith for which the immunotherapeutic composition comprising human BCDF is effective, will be briefly described and at the same time, current therapy will be described briefly.

In recent years, it has been proposed to call human BCDF BSF-2 (Nature, 324, 73 (1986)) but the term BCDF is used in this specification.

Immunodeficiency syndromes collectively refer to a state in which any aspect of the immune system is deficient and host defense ability of the body is reduced.

Immunodeficiency syndromes are roughly classified into two classes: primary immunodeficiency which is considered to be based on a congenital cause, and secondary immunodeficiency which is considered to be caused by any external cause or in association with other diseases.

In most cases, causes for primary immunodeficiency diseases are genetic defects of T cells and/or B cells. On the other hand, causes for secondary immunodeficiency diseases are various, but one of the major causes is infection with bacteria, viruses, etc. In particular, AIDS, which is caused by a certain virus, is a secondary immunodeficiency disease which has recently become a social problem.

Further, secondary immunodeficiency diseases are sometimes caused because the number of leucocytes is markedly reduced due to use of anti-cancer agents, radio-therapy, etc. When one suffers from immunodeficiency diseases, host defense ability of the living body decreases so that infectious diseases are frequently induced. Most pathogens of the infectious diseases are those that have been harmless heretofore but exhibit pathogenicity based on a change in the living body; such infectious diseases are called opportunistic infections. Such infectious diseases are noted with high frequency upon administration of anti-cancer agents, in particular, upon chemotherapy of acute leukemia and transplantation of bone marrow and, a lethal rate is also high. One opportunistic infection is carinii pneumonia induced by carinii protozoa, which is found in the terminal stage of AIDS.

These primary and secondary immunodeficient diseases are treated by the following 3 methods.

(1) Administration of chemotherapeutic agents such as antibiotics, antiviral agents (for example, AZT in the case of AIDS)

(2) Administration of human immunoglobulin or vaccine (3) Use of both in combination However, when the immune function is decreased, the above treatments do not exhibit pronounced effects. In addition, the therapeutic agents described above involve serious drawbacks shown below.

Firstly, antibiotics and antiviral agents are accompanied by serious side effects. In the case of antibiotics, resistant bacteria appear or microbial substitution occurs so that the effectiveness is restricted. Further in the case of immunoglobulin preparations, the amount of antibody to the objective infectious bacteria is only a trace so that the effect is poor. Further, with vaccines, the effect is hardly noted in an immunodeficient state.

Further as an example of secondary immunodeficiency diseases, when chemotherapeutic agents are administered to the patient with cancer and hematopoietic function is reduced to lead to a readily infectious state, the aforesaid therapeutic agents do not have any action of recovering the reduced hematopoietic function or differentiating and inducing the cancer cells themselves into normal cells. Accordingly, fundamental treatment is impossible.

Therefore an object of the present invention is to provide therapeutic compositions for treatment of cancers, primary and secondary immunodeficiency diseases as well as various infectious diseases induced by immunodeficiency diseases which are presently unknown and have actions in combination that (1) side effects are minimized, (2) there is no problem of appearance of resistant bacteria or microbial substitution, (3) antibody production specific to the objective antigen is induced and strengthened, (4) hematopoietic function is recovered, and (5) differentiation and induction of cancer cells is obtained, and the like.

As a result of extensive investigations to solve the foregoing problems, the present inventors have found that immunotherapeutic compositions comprising human BCDF as an effective component are effective for cancers, primary and secondary immunodeficiency diseases and various infectious diseases induced thereby and have accomplished the present invention.

Namely, the present invention relates to an immunotherapeutic composition comprising human BCDF as an effective component. The human BCDF in accordance with the present invention has, for example, amino acid sequence (I) or (II) described below:

Amino acid sequence (I):

```
PRO VAL PRO PRO GLY GLU ASP SER LYS ASP VAL
ALA ALA PRO HIS ARG GLN PRO LEU THR SER SER
GLU ARG ILE ASP LYS GLN ILE ARG TYR ILE LEU
ASP GLY ILE SER ALA LEU ARG LYS GLU THR CYS
ASN LYS SER ASN MET CYS GLU SER SER LYS GLU
ALA LEU ALA GLU ASN ASN LEU ASN LEU PRO LYS
MET ALA GLU LYS ASP GLY CYS PHE GLN SER GLY
PHE ASN GLU GLU THR CYS LEU VAL LYS ILE ILE
THR GLY LEU LEU GLU PHE GLU VAL TYR LEU GLU
TYR LEU GLN ASN ARG PHE GLU SER SER GLU GLU
GLN ALA ARG ALA VAL GLN MET SER THR LYS VAL
LEU ILE GLN PHE LEU GLN LYS LYS ALA LYS ASN
LEU ASP ALA ILE THR THR PRO ASP PRO THR THR
ASN ALA SER LEU LEU THR LYS LEU GLN ALA GLN
ASN GLN TRP LEU GLN ASP MET THR THR HIS LEU
ILE LEU ARG SER PHE LYS GLU PHE LEU GLN SER
SER LEU ARG ALA LEU ARG GLN MET
```

Amino acid sequence (II):

```
ALA PRO VAL PRO PRO GLY GLU ASP SER LYS ASP
VAL ALA ALA PRO HIS ARG GLN PRO LEU THR SER
SER GLU ARG ILE ASP LYS GLN ILE ARG TYR ILE
LEU ASP GLY ILE SER ALA LEU ARG LYS GLU THR
CYS ASN LYS SER ASN MET CYS GLU SER SER LYS
GLU ALA LEU ALA GLU ASN ASN LEU ASN LEU PRO
LYS MET ALA GLU LYS ASP GLY CYS PHE GLN SER
GLY PHE ASN GLU GLU THR CYS LEU VAL LYS ILE
ILE THR GLY LEU LEU GLU PHE GLU VAL TYR LEU
GLU TYR LEU GLN ASN ARG PHE GLU SER SER GLU
GLU GLN ALA ARG ALA VAL GLN MET SER THR LYS
VAL LEU ILE GLN PHE LEU GLN LYS LYS ALA LYS
ASN LEU ASP ALA ILE THR THR PRO ASP PRO THR
THR ASN ALA SER LEU LEU THR LYS LEU GLN ALA
GLN ASN GLN TRP LEU GLN ASP MET THR THR HIS
LEU ILE LEU ARG SER PHE LYS GLU PHE LEU GLN
SER SER LEU ARG ALA LEU ARG GLN MET
```

Amino acid sequence (I) is natural human BCDF and amino acid sequence (II) is a polypeptide having one Ala added to the N-terminal of natural human BCDF (hereafter referred to as Ala-BCDF). However, it is not always necessary that human BCDF used in the present invention takes the structure shown by amino acid sequence (I) or amino acid sequence (II) described above.

Namely, that having a structure in which one or more amino acids are added from the N terminal and/or C terminal of natural human BCDF and that having a structure in which one or more amino acids in the structure of natural human BCDF are replaced with other amino acids can also be used as human BCDF of the present invention as far as they have human BCDF activity. Natural human BCDF or human Ala-BCDF is preferably employed. The content of human BCDF in accordance with the present invention is 0.0001 to 100 wt %, preferably 0.1 to 1.0 wt %, based on the immunotherapeutic composition.

The immunotherapeutic composition comprising human BCDF as an effective component of the present invention may also contain a stabilizer such as serum albumin, etc., an excipient such as mannitol, etc. In addition to human BCDF, the immunotherapeutic composition of the present invention may further contain at least one of human IL-2, human IL-3, lentinan and mouse IL-3 as an aid.

When such an aid is incorporated, the effect of the immunotherapeutic composition increases synergistically. While there is no particular limitation to the amount of these aids to be incorporated, it is preferred to incorporate 0.0001 to 200,000 wt %, based on human BCDF being 100. The amount of these aids to be added is not limited to the range described above but may be approximately determined depending upon condition, age of the patient, etc.

Aids such as human IL-2, human IL-3, mouse IL-3 and lentinan are not always given simultaneously with human BCDF as the same composition. Namely, these aids may also be administered in an appropriate period prior to or after administration of the immunotherapeutic composition comprising human BCDF as the effective component.

Of course, the immunotherapeutic compositions of the present invention may also be used in combination with other chemotherapeutic agents, anti-cancer agents, anti-viral agents, antibiotics, etc. The immunotherapeutic composition may also be used in combination with vaccine therapy to strengthen the effect. The immunotherapeutic composition may be given by intravenous injection, intramuscular injection or subcutaneous injection. That is, the composition may be given in any form of injection.

Human BCDF used in the present invention may be produced from human T cells, B cells, fibroblasts, etc. and purified in a known manner (Proc. Natl. Acad. Sci., USA, 82, 5490 (1985)) or produced by culturing a strain obtained by transformation of a gene encoding human BCDF to an appropriate host such as *Escherichia coli*, yeast, monkey cells (COS cells), hamster cells, etc. using an appropriate vector and further purified. With respect to the production of human BCDF, its process will be explained in the examples again.

It is clear that the immunotherapeutic composition of the present invention is effective for treatment and prophylaxis of various infectious diseases (carinii pneumonia, etc. induced from AIDS) derived by immunodeficient diseases. For example, in case that pathogens such as bacteria, fungi, protozoa, viruses, etc. are infected, an antibody thereto is produced and then the antibody protects the living body from the pathogens by 1) direct neutralization and precipitation, 2) augmentation of phagocytosis of phagocytes by opsonification, 3) lysis by activation of the complement system, 4) antibody-dependent cell mediated cytotoxicity, etc.

Namely, the immunotherapeutic composition of the present invention can enhance production of specific antibody by the patient with primary immunodeficiency diseases due to genetic factors, etc. and secondary immunodeficiency diseases in which immune function is reduced due to administration of chemotherapeutic agents or administration of immunosuppressive agents and viral infections, etc., whereby a readily infectious state can be improved and treated.

The present inventors have found that human BCDFs not only enhance antibody production but also effect growth of bone marrow cells, as well as induction of differentiation of tumor cells. From these actions, it has been noted that BCDF is not only effective for treatment of infectious diseases due to enhanced antibody production to the patient with primary immunodeficiency diseases or with secondary immunodeficiency diseases but can also accelerate hematopoietic function in the patient with immunodeficiency diseases and exhibit therapeutic effects in the patient with cancer.

It is already known that 1) IL-2 is capable of enhancing antibody production, 2) colony stimulating factor (CSF) causes growth of bone marrow cells and 3) γ-interferon (γ-IFN) has an action of induction of differentiation of tumor cells, but there is currently unknown a substance having three functions of (1) enhancement of antibody production, (2) growth of bone marrow cells and (3) induction of differentiation of tumor cells in combination. Accordingly, human BCDF in accordance with the present invention is an important drug which was unknown until now.

The immunotherapeutic composition comprising human BCDF as the effective component of the present invention has three functions of (1) enhancement of antibody production (2) growth of bone marrow cells and (3) induction of differentiation of tumor cells in combination so that the immunotherapeutic composition is effective for treatment of primary immunodeficiency diseases, secondary immunodeficiency diseases accompanied by viral infections or administration of anti-cancer agents or immunosuppressive agents, as well as the cancer patient.

Further in the patient with immunodeficiency diseases, antibody production is decreased as a matter of course and various infectious diseases have been caused or are ready to be caused due to decreased hematopoietic function. The immuno-therapeutic composition comprising human BCDF as the effective component of the present invention is also effective for treatment and prophylaxis of these infectious diseases.

The present inventors described the synergistic effect of IL-2 or IL-3 with BCDF in antibody production and hematopoiesis, especially. But cytokines, having synergistic effect with BCDF, are not limited only to IL-2 and IL-3. Accordingly, it is supposed that BCDF will act synergistically with other cytokines, such as IL-1, IL-4, IL-5, BCGF, GM-CSF, G-CSF, M-CSF, TNF, MAF, etc., in many biological function assays. For example, results have been obtained by the present inventors which show that IL-1 exhibits a synergistic effect in differentiation of tumor cells with BCDF. Other cases are shown below.

1) IL-4, IL-5 or BCGF for synergistic augmentation of antibody production.
2) IL-1 or TNF for synergistic augmentation of differentiation of tumor cells.
3) CSFs, as well as IL-3, for synergistic augmentation of cell proliferation.
4) MAF, as well as LNT (lentinan), for partial augmentation of host defense mechanisms.

Thus, immunotherapeutic compositions containing BCDF and one or more cytokines are also useful for treatment of infection, etc., by augmentation of host defense mechanisms.

The invention now being generally described, the same will be better understood by reference to certain specific examples which are included herein for purposes of illustration only and are not intended to be limiting of the invention or any embodiment thereof, unless specified.

EXAMPLE 1

RPMI 1640 medium (1 l) (glutamine (2 mM), 2ME ($5 \times 10^{-5}$M), penicillin (100 units/ml), streptomycin (100 μg/ml), gentamycin (20 μg/ml), NaHCO$_3$ (16 mM)) which further contains 20% FCS was placed in a 2 l plastic roller type fermentor (roller culture bottles) (Falcon #3027) (hereinafter referred to as "roller"). Cells ($2 \times 10^5$/ml) of VT-1 were inoculated in the medium in the roller and cultured at 37° C. at 8 rpm for 3 days. After the cultivation, the cultured mixture was centrifuged to collect the cells which were then washed twice with RPMI 1640 medium. The VT-1 cells thus prepared were suspended at a cell concentration of $1 \times 10^6$/ml in RPMI 1640 medium (1 l) in a 2 liter-roller. The suspension thus obtained was cultured at 37° C. at 8 rpm for 2 days. After the cultivation, the mixture was centrifuged to obtain a supernatant solution.

The supernatant containing BCDF, prepared as above from the culture of VT-1, was treated in a manner described below, so that BCDF was isolated in a purified form. Thus, the supernatant, freed from the cells (10 l), was filtered under a pressure of 4 Kg/cm$^2$ in a nitrogen atmosphere through an ultrafiltration device (Amicon cell Type No. 2000 for a large scale treatment (a mass treatment): a product of Amicon Corporation; Massachusetts, USA) furnished with an ultrafiltration membrane (Amicon YM-10, Amicon Corporation, a product of Amicon Corporation; Massachusetts, USA). A residual concentrate (100 ml) remaining over the ultrafiltration membrane was again filtered under a pressure of 4 kg/cm$^2$ in a nitrogen atmosphere through an ultrafiltration equipment (Amicon standard cell Type No. 52) furnished with an ultrafiltration membrane Amicon YM-10. The residual concentrate (5 ml) over the ultrafiltration membrane was collected.

The concentrated supernatant was subjected to gel-filtration on a column (LKB producer, Sweden, 2.6×90 cm) filled with AcA-34 gel which had previously been equilibrated in PBS ((0.01M) phosphate buffer (pH 7.0) containing sodium chloride (0.15M)). The AcA-34 gel in the column was eluted with PBS, the eluate being fractionated into 5 ml fractions. BCDF activity of these fractions was examined. The fractions having BCDF activity were found to be in the fractions corresponding to molecular weight of $3.5+0.5 \times 10^4$ Dalton. The gel-filtration column was assayed by the use of a molecular weight marker (product of Pharmacia Fine Chemicals; Sweden) in the following manner.

The fractions containing blue-dextran 200 ($2 \times 10^6$), ferritin ($4.5 \times 10^5$), aldolase ($1.58 \times 10^5$), ovalbumin ($4.5 \times 10^4$), chymotrypsinogen ($2.5 \times 10^4$) and cytochrome C ($1.17 \times 10^4$) or BCDF were collected and combined, and the buffer solution of the combined fractions was converted into a 25 mM piperazine-HCl buffer solution (pH 6.3) on ultrafiltration equipment furnished with an ultrafiltration membrane (Amicon YM-10). The BCDF fractions, as obtained in AcA-34 gel column chromatography, were passed through a column, filled with Mono P (Pharmacia Fine Chemicals, Sweden) which had previously been equilibrated in 25 mM piperazine-HCl buffer solution (pH 6.3). The column filled with the Mono P, was washed with 25 mM piperazine-HCl buffer solution, followed by elution with 40 ml) of polybuffer 74 (Pharmacia Fine Chemicals, Sweden) which had been diluted 10 times and adjusted to pH 4.5 with aqueous HCl. The elution was performed at a flow rate of the eluent as 0.5 ml/minute by means of First protein Liquid Chromatography (FPLC) (Pharmacia Fine Chemicals, Sweden). The eluate was fractionated into 1 ml portions, on which BCDF activity and pH value were examined. The BCDF activity was detected in the fractions of eluate at the pH value 4.9 to 5.1.

The BCDF active fraction obtained in the chromatography on the column of Mono P was subjected to high performance liquid chromatography on a reverse phase chromatography column; Synchropak RPP (C18) (250×4.1 mm, Synchrom) which had been buffered with 0.1% aqueous TFA (trifluoroacetic acid). The column was eluted by gradient elution while increasing acetonitrile concentration from 0 to 60% in 0.1% aqueous TFA solution (eluting solution). The fraction of eluate which was eluted out at the concentration of acetonitrile 50 to 55% indicated a peak of absorption (O.D. 280) as separated distinctly from the other peaks of absorption (O.D. 280). The BCDF activity was detected correspondingly to and coincidently with this peak. This fraction was then lyophilized to obtain a BCDF preparate.

The BCDF preparate was subjected to electrophoresis on SDS-polyacrylic amide gel (12%) under a reducing condition. After the electrophoresis, the gel fractions corresponding to molecular weight of 21000 was separated from other gel fractions by cutting. The fractions isolated was admixed with SDS (0.05%) and $NH_4HCO_3$ in an Eppendorf tube and the mixture was stirred at 37° C. over-night so that BCDF was extracted. The extract thus obtained was again subjected to HPLC on reverse phase chromatography column; Synchropak RP-P (C18) (250×4.1 mm, Synchrom) which was eluted by gradient elution while increasing acetonitrile concentration from 0 to 60% in 0.1% aqueous TFA solution. The fraction of eluate which was eluted at a concentration of acetonitrile of 50 to 55% indicated a peak of absorption (O.D. 280) as separated distinctly from the other peaks (O.D. 280). It was found that the peak corresponded to the BCDF activity. This fraction was lyophilized to obtain a purified BCDF preparate.

In determination of amino acid sequence in BCDF protein, the purified BCDF (6 µg) obtained as above was introduced into a protein sequencer (See: Applied Biosystem Co., Calif, Model 470 A). The determination of amino acid sequence was performed according to the method described in *J. Biol. Chem.*, 193, 265~275 (1951). The sequence of amino acids starting from the N-terminal was as follows;

| Pro | Val | Pro | Pro | Gly | Glu |
| Asp | Ser | Lys | Asp | Val | Ala |
| Ala | | | | | |

EXAMPLE 2

A purified BCDF preparation (20 µg), prepared in the same manner as in Example 1, was dissolved in 5 mM Tris-HCl buffer solution (pH 9.5), to which was added Lysyl endopeptidase (Wako), (mol. ratio of Lysyl endopeptidase to the BCDF preparate was 1:200). The mixture was allowed to react at 37° C. for 6 hours so that the BCDF was decomposed into fragments. The reaction solution was subjected to HPLC on a reverse phase chromatography column, µ Bondo Pack (0.21×30 cm), which was eluted by gradient elution, while increasing the acetonitrile concentration from 0 to 60% in 0.06% aqueous TFA (eluant) solution so that the fragments were eluted separately from each other. Elution peaks as numbered 1 to 9 in the HPLC were recovered. Each of the eluates which corresponded respectively to the peak No. 1 to 9 was lyophilized, and the lyophilization product was introduced (incorporated) into protein sequencer (See; Applied Biosystem Co., Calif, Model 4704). Amino acid sequence was determined according to the method as described in *J. Biol. Chem.*, 193, 265~275 (1951).

Of the fragments mentioned above, the amino acid sequence could be determined for fragment Nos. 3, 8, 2 and 6. The amino acid sequences were as follows;

Fragments No. 3
Lys-Glu-Ala-Leu-Ala-Glu
Fragments No. 8
Lys-Leu-X-Ala-Gln-Asn-Gln-Trp-Leu-Gln-Y-Met
Fragment No. 2
Pro-Val-Pro-Pro-Gly-Glu-X-Y-Lys
Fragment No. 6
Asp-Val-Ala-Ala-Pro-X In the above, X and Y are amino acids which could not be determined. The fragments Nos. 2 and 6 correspond to the N-terminal amino acid sequences as described in the Example 1.

EXAMPLE 3

This example describes a method for synthesis of an oligonucleotide encoding the amino acid sequence of the BCDF as obtained in Examples 1 and 2.

The oligonucleotide was synthesized by a binding reaction of nucleotides in a phosphorous acid triester method, with silica gel as solid carrier, using DNA synthesizer model 380 A (Applied Biosystem Co., Calif.). After removal of protecting groups in a conventional manner, the deprotection product was subjected to HPLC on a reverse phase chromatography column, Synchropak RP-P (C18) which was eluted by gradient elution while increasing acetonitrile concentration, so that the desired oligonucleotides were obtained in a purified form.

|  | Probe No. |
|---|---|

Fragment No. 3

Lys—Glu—Ala—Leu—Ala—Glu

```
            A
AAA—GAA—GCA—TTA—GCG—GA...     3-1
 G    G    G    G    C
                     T

A
AAA—GAA—GCA—CTA—GCG—GA...     3-2
 G    G    G    G    C
                     T

A
AAA—GAA—GCA—CTC—GCG—GA...     3-3
 G    G    G    T    C
                     T

A
AAA—GAA—GCC—TTA—GCG—GA...     3-4
 G    G    T    G    C
                     T

A
AAA—GAA—GCC—CTA—GCG—GA...     3-5
 G    G    T    G    C
                     T

A
AAA—GAA—GCC—CTC—GCG—GA...     3-6
 G    G    T    T    C
                     T
```

(each of 64 types of mixtures)

Fragment No. 8

Lys—Leu—X—Ala—Gln—Asn—Gln—Trp—Leu—Gln—Y—Met

```
GCA—CAA—AAT—CAA—TGG—TT        8-1
 G    G    C    G    C

GCT—CAA—AAT—CAA—TGG—TT        8-2
 C    G    C    G    C
```

(each of 32 types of mixtures)

N-terminal amino acid sequence

```
 1    2    3    4    5    6    7    8    9   10   11   12   13
Pro—Val—Pro—Pro—Gly—Glu—Asp—Ser—Lys—Asp—Val—Ala—Ala

GAA—GAT—TCA—AAA—GAT—GT...     N-1
 G    C    G    G    C

GAA—GAT—TCT—AAA—GAT—GT...     N-2
 G    C    C    G    C

GAA—GAT—AGT—AAA—GAT—GT...     N-3
 G    C    C    G    C
```

(each of 32 types of mixtures)

```
            T
AAA—GAT—GTA—GCA—GCA—CC...     N-4
 G    C    G    G    G
                     C

T
AAA—GAT—GTA—GCT—GCA—CC...     N-5
 G    C    G    C    G
                     C

AAA—GAT—GTT—GCA—GCA—CC...     N-6
 G    C    C    G    G
                     C
```

```
         T
AAA—GAT—GTT—GCT—GCA—CC...           N-7
  G    C    C    C    G
                      C
```

(each of 64 types of mixtures)

EXAMPLE 4

(1) RPMI 1640 medium (1 l) (glutamine (2 mM), 2ME ($5\times10^{-5}$M), penicillin (100 units/ml), streptomycin (100 μg/ml), gentamycin (20 μg/ml), NaHCO₃ (16 mM)) which further contains 20% FCS was placed in a 2l-plastic roller type fermentor (roller culture bottles) (Falcon #3027) (hereinafter referred to as roller). Cells ($2\times10^5$/ml) of VT-1 were inoculated in the medium in the roller and cultured at 8 rpm and at 37° C. for 3 days. After the cultivation, the cultured mixture was centrifuged to collect the cells which were washed twice with PBS. The cells ($1.8\times10^9$/ml) were then suspended in PBS solution (800 ml) and washed by centrifugation. This procedure was repeated twice to wash the cells. The cells were suspended in RSB solution (Tris-HCl (pH 7.5) (10 mM), NaCl (10 mM), MgCl₂ (1.5 mM)) (800 ml) which further contained a nuclease inhibitor; ribonucleosides-vanadyl complex (10 mM). The suspension thus obtained was admixed with NP-40 (0.05%) and stirred slowly. The mixture was centrifuged at 3000 rpm for 5 minutes to precipitate cell debris, containing nuclei, which was then removed. The resultant supernatant was admixed with SDS (final concentration: 0.5%) and EDTA (final concentration: 5 mM), followed by treatment with equal volume of phenol so that cytoplasmic RNA was recovered by extraction. The extraction with phenol was repeated three times and the extracts thus obtained were combined and admixed with a two-fold volume of ethanol to deposit a precipitate of RNA which was recovered by centrifugation and was dissolved in Tris-HCl (10 mM) (pH 7.5). RNA was recovered from VT-1 cells in a yield of 30 mg.

mRNA was obtained from the RNA in the following manner.

The RNA obtained was subjected to chromatography on a column filled with oligo (dT)-cellulose (P.L. Biochemicals, Type 7). The RNA dissolved in a solution containing Tris-HCl (20 mM) (pH 7.5), NaCl (0.5M), EDTA (1 mM), and SDS solution (0.5%) was passed through the column, prepared as above to effect the absorption, and which was washed with a buffer solution (Tris-HCl (20 mM) (pH 7.5), NaCl (0.5M) EDTA (1 mM)) and then eluted alternately with water and Tris-HCl (10 mM) (pH 7.5), so that mRNA was eluted out. The yield of mRNA thus eluted was 576 μg.

(2) From the mRNA (5 μg) as prepared in the step (1) above, double-stranded cDNA was prepared as follows:

Double-stranded cDNA was prepared according to the Amersham protocol using a cDNA-synthetizing kit (Amersham) according to the method described in GUBLER, U and HOFFMAN, B, J., (Gene 25, 263, 1983). Thus, reverse transcriptase was reacted on mRNA to synthetize single-stranded cDNA. Escherichia coli ribonuclease H was made to act on hybrid of mRNA and cDNA as substrate to form nicks and gaps in the RPMI linkage. mRNA was replaced by the DNA by nick-translation type of reaction using Escherichia coli DNA polymerase I so that double-stranded DNA was prepared. The double-stranded DNA was modified by removing the small over-hang at the 3'-terminal sequence by the use of T4 DNA polymerase.

The double-stranded cDNA was finally obtained in a yield of 1.08 μg.

(3) The double-stranded cDNA (1.08 μg) thus obtained was fractionated by sucrose density gradient centrifugation (from 5 to 25% sucrose density gradient in a solution (pH 7.5) containing Tris-HCl (50 mM) EDTA (1 mM), as centrifuged at 40000 rpm for 13 hours at 4° C.). Some fractions thus fractionated were analyzed on autoradiogram prepared by agarose gel electrophoresis. The fractions corresponding to the double-stranded cDNA having a size of above 500 bp were combined and admixed with ethanol to recover the double-stranded cDNA (about 0.6 μg) as a precipitate.

(4) A mixture of 0.1M potassium cacodylate (adjusted to pH 7.2 with Tris-base), DTT (10 mM), CoCl₂ (2 mM), $^{32}$P-dCTP (0.5 mM) (specific activity: $1\times10^6$ cpm/n mole), double-stranded cDNA (0.6 μg) and deoxynucleotidyl terminal transferase (BRL) was incubated at 24° C. for 20 minutes, follows by treatment with phenol. The mixture was passed through a column filled with Sephadex G-50 thereby fractions of cDNA were collected. The fractions of cDNA thus collected were combined and was admixed with ethanol to deposit the dC-tailed cDNA (0.24 μg). In a molecule of the cDNA, about 13 of dCMP residues are combined to the 3'-terminal sequences of the both sides.

(5) cDNA expressing vector pQ which functions in monkey cells (COS cells) was constructed from pCEIL-2 (See: Nature, 302, 305 (1983)) as shown in FIG. 1. pQ vector can insert cDNA to the promoters from either side to express peptide protein to be encoded by the cDNA in COS cells. The pQ vector can also be replicated in the cells of Escherichia coli, and can be selected as resistant cells against tetracycline.

The pQ vector was cleaved with Pst I, to which was combined about 13 dG tails in the same manner that dC tails were combined to the 3'-terminal on both sides of a ds-cDNA.

The dG-tailed pQ (100 ng) was mixed with dC-tailed ds-cDNA (20 ng) in an aqueous solution containing Tris-HCl (50 mM) (pH 7.5), NaCl (0.1M), EDTA (1 mM) and the mixture was incubated successively at 65° C. for 2 minutes, at 45° C. for 60 minutes, at 37° C. for 60 minutes and finally at room temperature for 60 minutes. The annealed DNA products thus obtained were introduced into competent cells of E. coli MC 1061. Preparation of competent cells of E. coli MC 1061 and introduction of the annealed DNA into the cells prepared were performed in the following manner.

Cells of E. coli MC 1061 were inoculated into medium (100 ml) (2% trypton, 0.5% yeast extract, 0.5% MgSO₄.7H₂O, pH 7.6) and cultured at 37° C. under stirring until the absorbance (optical density) at 550 nm of the culture solution became around 0.3 to 0.5. After the completion of the cultivation, the cultured solution was allowed to stand at 0° C. for 5 minutes, followed by centrifugation to harvest the cells which were then suspended in the TfbI (40 m l) (potassium acetate (30 mM), RbCl) (100 mM), CaCl₂ (10 mM), MnCl₂ (50 mM), glycerine (15%), pH 5.8) and the suspension was allowed to stand at 0° C. for 5 minutes.

The suspension was again centrifuged to harvest the cells which were then suspended in the TfbII (40 ml) (10 mM MOPS or PIPES, CaCl₂ (75 mM), RbCl (10 mM), glycerine (10%), pH 6.5), followed by standing at 0° C. for 15 minutes. The suspension thus treated was divided into portions, which were allowed to stand at −70° C.

Competent cells of *E. coli* MC 1061 (100 l), prepared as described above, were allowed to stand at 0° C. for 15 minutes, to which were added the annealed product (10 μl) of dG-tailed pQ vector with dC-tailed cDNA and an aqueous solution (90 μl) containing $MgCl_2$ (50 mM) and $CaCl_2$ (10 mM), and the resultant mixture was allowed to stand at 0° C. for 20 minutes. The mixture solution was heated to 37° C. for 60 seconds and then kept at 0° C. for 1–2 minutes, to which was added Ψ medium (1 ml). The mixture solution was cultured at 37° C. under stirring for 60 minutes.

The cultured solution thus obtained was spread on an agar plate of L broth (1% trypton, 0.5% yeast extract, 0.5% NaCl, 0.1% glucose) which further contains tetracycline (15 μg/ml) and streptomycin (25 μg/ml) and incubated at 37° C. overnight, to form colonies thereon.

(6) The cloned transformant strains (about 150,000 strains) were subjected to colony hybridization using probes 8-1 and 8-2, according to the method described in "Grunstein, M. et al; Methods in Enzymology, 68, 379 (1979)". As the result, there were detected 10 cloned strains which hybridize with probe 8-1. The cloned strains thus obtained were again subjected to colony hybrization using probes from 3-1 to 3-6, in the same manner as described above, so that one cloned strain was found to hybridize with the probe 3-2. Plasmid DNA, which the cloned strain contained, was isolated and purified in a conventional manner. The plasmid DNA was cleaved with restriction enzyme Pst I and the cleavage product was subjected to agarose electrophoresis; thereby the cDNA insert was separated from pQ vector.

The plasmid DNA was subjected to Southern hybridization using probes 8-1, 8-2, 3-1→3-6 and N-1→N-7. As the result, it was found that the plasmid DNA hybridizes with 8-1, 3-2, N-2 and N-5, but does not hybridize with any other probes. This plasmid DNA was named pBSF 2-38. It is also apparent that the cDNA insert, which the plasmid DNA (pBSF 2-38) contains therein has nucleotide sequences corresponding to some of the partial amino acid sequences detected in Example 2. The cDNA has thus been identified as a gene encoding BCDF.

EXAMPLE 5

(1) Preparation in a large quantity of plasmid DNA (pBSF 2-38):

Cells of *E. coli* MC 1061 strain (FERMBP-1402) containing the pBSF 2-38 were inoculated into Ψ medium containing tetracycline (20 μg/ml) and streptomycin (25 μg/ml) and cultured at 37° C. with shaking for 5 to 7 hours. To the cultured solution was further added freshly prepared Ψ medium (100 ml) containing chloramphenicol at 170 μg/ml as the final concentration, and cultured, with shaking, overnight.

Plasmid DNA thus amplified was purified as follows. The cultured solution obtained as above was centrifuged to harvest the cells which were suspended in a buffer solution (5 ml) (50 mM Tris-HCl, pH 7.5). The suspension was frozen at −80° C., followed by thawing. The suspension, after thawing, was admixed with lysozyme added (1 mg/l as final concentration) and the mixture was allowed to stand at 0° C. for 10 minutes. To the mixture was further added EDTA at 0.1 M as final concentration, and allowed to stand at 0° C. for 10 minutes. The mixture was then admixed with Triton X-100 at 0.1% as final concentration, and allowed to stand at 0° C. for 60 minutes. The mixture was centrifuged at 30,000 rpm for 30 minutes to obtain a supernatant solution. The supernatant was admixed with an equal volume of phenol saturated with water and the aqueous layer separated was again admixed with an equal volume of chloroform. To the aqueous layer separated was added RNase solution at 20 μg/ml as final concentration and the mixture solution was incubated at 37° C. for 60 minutes. The incubated solution was admixed with 0.2 volume of 5M NaCl and ⅓ volume of polyethylene glycol and the mixture solution was then allowed to stand at 0° C. for 60 minutes, followed by centrifugation at 10,000 rpm for 20 minutes to recover DNA as precipitate.

The precipitate recovered was dissolved into water (3.8 ml), to which was added CsCl (4 g) and the resultant solution was admixed with EtBr 200 μl of 10 mg/ml. The mixture was ultracentrifuged at 40,000 rpm for 16 hours at 20° C.

Plasmid DNA fraction recovered, after the ultracentrifugation was extracted 4 times with 1 to 2 volumes of n-butanol saturated with water to remove EtBr therefrom. Solution of plasmid DNA was dialyzed against $H_2O$ to remove CsCl, and the solution was admixed with ¹/₁₀ volume of 3M aqueous solution of sodium acetate (pH 5.6) and then with 2 volume of cold ethanol, and the mixture was allowed to stand at −20° C. overnight, thereby a precipitate was deposited. The mixture was centrifuged to recover the precipitate which was washed with 80% aqueous ethanol solution and thoroughly dried. The solid matter thus obtained was dissolved in a buffer solution (10 mM Tris-HCl, pH 7.5) (50 μl) which was served as the sample for transfection in monkey cells.

(2) Transfection of plasmid into COS-7 cells of monkey; COS-7 cells ($1 \times 10^5$/ml) were suspended in RPMI containing FBS (fetal bovine serum) (10%). 3 ml portion of the suspension was placed in a shale (6 cm in diameter) and cultured at 37° C. overnight in a $CO_2$ gas (5%) incubator. Next morning, the culture supernatant was removed, and, to the residue, was again poured a freshly prepared RPMI (3 ml) containing FBS (10%), and then cultured at 37° C. for 2 hours in a $CO_2$ gas (5%) incubator. After the cultivation, the supernatant was removed and the cell was washed once with 2.5 ml of TBS (Tris-HCl (25 mM), pH 7.5, NaCl (130 mM), KCl (5 mM), $Na_2HPO_4$ (0.6 mM)). The adherent COS-7 cells was admixed with a mixture of plasmid [TBS (+), namely TBS mixed with 0.7 mM $CaCl_2$ and 0.5 mM $MgCl_2$ (10 ml); plasmid DNA (2 γ), DEAE-dextran (10 mg/ml) (50 μ)] and the mixture was cultured at 37° C. for 4 hours in a $CO_2$ gas (5%) incubator. After removal of the supernatant which appeared during the cultivation, the culture was washed with TBS (2.5 ml), to which was added RPMI (2.5 ml) containing FBS (10%) and further chloroquine (150 M). The mixture was cultured at 37° C. for 5 hours in a $CO_2$ gas (5%) incubator. After the removal of the supernatant appeared during the cultivation, the culture was washed with TBS (2.5 ml), to which was poured RPMI (2.5 ml) containing FBS (10%) and further chloroguine (150 μM). The mixture was cultured at 37° C. for 5 hours in a $CO_2$ gas (5%) incubator. After the removal of the supernatant the culture was washed twice (each of 2.5 ml) with TBS. The culture was again admixed with the RPMI (3 ml) containing FBS (10%) and cultured at 37° C. overnight in a $CO_2$ gas (5%) incubator. After the removal of the supernatant, the culture was again admixed with the RPMI (3 ml) containing FBS (10%) and cultured at 37° C. for 2 days in a $CO_2$ gas (5%) incubator. The culture mixture was centrifuged to recover the supernatant which was used as the sample for the assay of BCDF activity.

Figure 2:
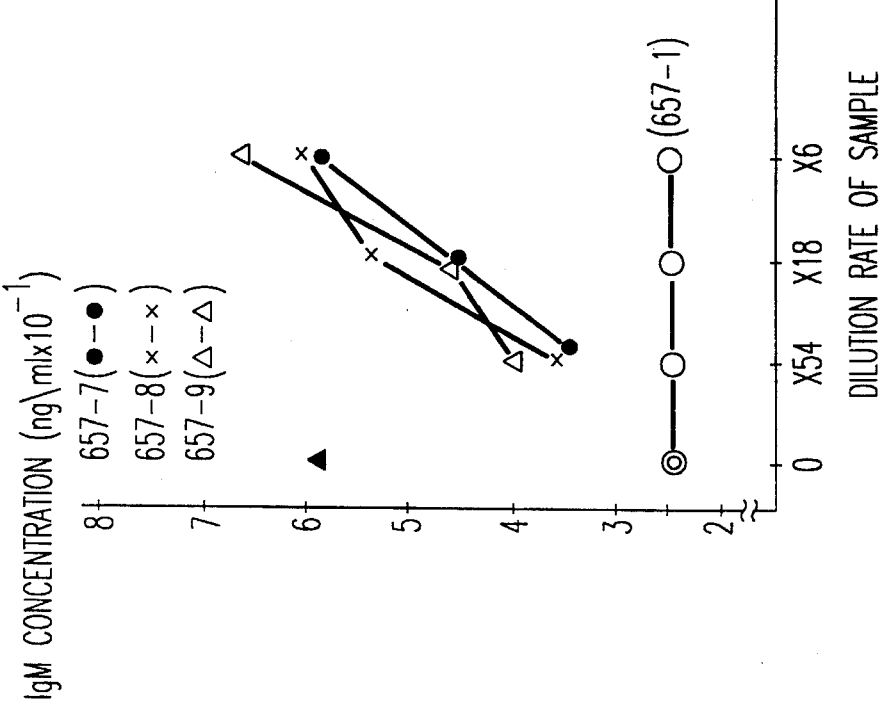
FIG. 2 shows the BCDF activity of the culture supernatant of monkey cells (COS-7) to which PBSF 2-38 cDNA was introduced.

The supernatant of COS culture was assayed for BCDF activity by the use of CL4. The results obtained are shown in FIGS. 2 and 3.

As apparent from the data, COS-7 cells to which pBSF 2-38 plasmid DNA was transfected exhibit BCDF activity higher than the control. FIG. 2 shows activity, based on IgM assayed by an ELISA of the supernatant of monkey cells (COS-7) to which was transfected pBSF 2-38 cDNA. FIG. 2 shows the activity of purified BCDF (1 U/ml) obtained from VT-1, 657-7, 8, 9 in the supernatant of the culture cells (COS-7) to which was introduced BCDF-cDNA, and 657-1 is the supernatant of culture cells (COS-7) to which was introduced lymphokine cDNA.

Figure 3:
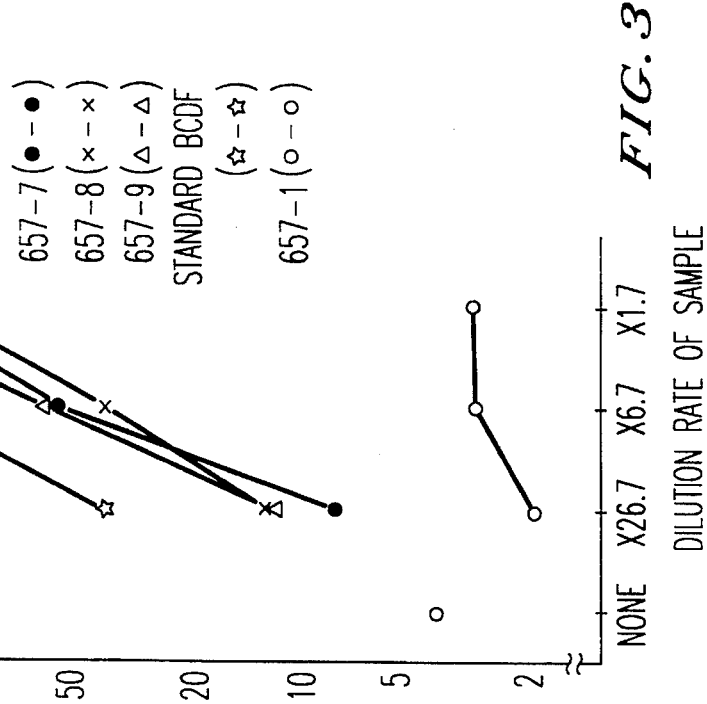
FIG. 3 shows the BCDF activity, as assayed by reverse plaque method, of the culture supernatant of monkey cells (COS-7) in which PBSF 2-38 cDNA were introduced.

FIG. 3 shows BCDF activity, as determined by reverse-plaque method, of the supernatant of monkey culture cells (COS-7) to which was introduced pBSF 2-38 cDNA. In the FIG. 3, o is the BCDF activity of the supernatant of monkey culture cells (COS-7) cultured without any additives. 657-1, 657-7, 8, 9 are the same as defined in FIG. 2. BCDF having a potency of 50 U/ml is used as standard.

Recombinant human BCDF produced in the cells of eukaryote (COS-7) as described above was purified by passing the culture solution through a column for immobilizing antibody of BCDF and by subjecting the eluate to reverse phase HPLC (Synchropak (C18)). The BCDF was found to contain a saccharide moiety which may be attributable to the existence of an N-glycosylation site, from the amino acid sequence encoded in the cDNA.

The BCDF now obtained coincides in its physicochemical properties as shown below with the purified BCDF obtained from the supernatant of the VT-1, culture by the method described in the Example 1:
(i) Molecular weight:

3.5±0.5×10$^4$ dalton (assayed by gel-filtration)

2.2±0.2×10$^4$ dalton (assayed by SDS-polyacrylic amide electrophoresis)

(ii) Isoelectric point: pH 4.9–5.1

EXAMPLE 6 pBSF 2-38 prepared in Example 5, step (1) was cleaved with restriction enzyme Bam HI, thereby BCDF cDNA insert was obtained. The BCDF cDNA insert thus obtained was used as probe for the assessment of BCDF mRNA. mRNA to be used was prepared from various origins such as VT-1 cells capable of the BCDF concerned; CESS, RPMI 1788 which are estimated to produce BCDF; tonsilar cells stimulated with TPA; CL4, Jurkat and CEM in which BCDF activity is not detected, and human tonsilar cells which was not stimulated, in the same manner as in the Example 4, step (1).

A mixture of each mRNA (10 μg/3.6 μl), 5×MOPS buffer solution (0.1M MOPS (pH 7.0), 75 mM NaOAc, 5 mM EDTA) (6.0 μl), formaldehyde (5.4 μl) and formamide (15.0 μl) was incubated at 60° C. for 15 minutes. To the mixture was added 3 μl of a coloring solution (80% aqueous glycerol containing 0.5% bromophenol blue and 0.05% xylene cyanol), which was used as the sample to be tested. The sample thus prepared was subjected to electrophoresis in agarose gel (1.6%) containing 1.8% formaldehyde using 1×MOPS buffer solution. Blotting onto nitrocellulose filter was performed in a conventional manner. The filter was baked at 80° C. for 3 hours. The filter thus prepared was dipped in 3×SSC containing 0.1% SDS and prehybridized in a 50 mM sodium phosphate buffer (pH 6.5) containing 1×Denhardt solution, 50% formamide, 5×SSC and 250 μg/ml herring DNA, at 42° C. overnight. Hybridization was conducted in a 50 mM sodium phosphate buffer (pH 6.5) containing 1×Denhardt solution, formamide (50%), 5×SSC and herring DNA (250 μg/ml) using $^{32}$P-labelled pBSF 2-38 Bam HI cDNA insert as probe at 42° C. overnight.

The filter thus hybridized was washed 4 times for 5 minutes with 2×SSC containing 0.2% SDS at room temperature, and twice for 30 minutes with 0.1×SSC containing 0.2% SDS at 50° C. The filter was air-dried and then was subjected to autoradiography. Autoradiograms were thus prepared. The results obtained show that mRNA derived from VT-1, CESS (BCDF-producing strain), RPMI 1788 was hybridized with pBSF 2-38 cDNA probe, but mRNA derived from CL-4, Jurkat, CEM and CESS which are not capable of producing BCDF was not hybridized with pBSF 2-38 cDNA probe.

mRNA capable of hybridizing with pBSF 2-38 cDNA probe was calculated to be 15→16S in size.

Figures 4A, 4B, 4C:
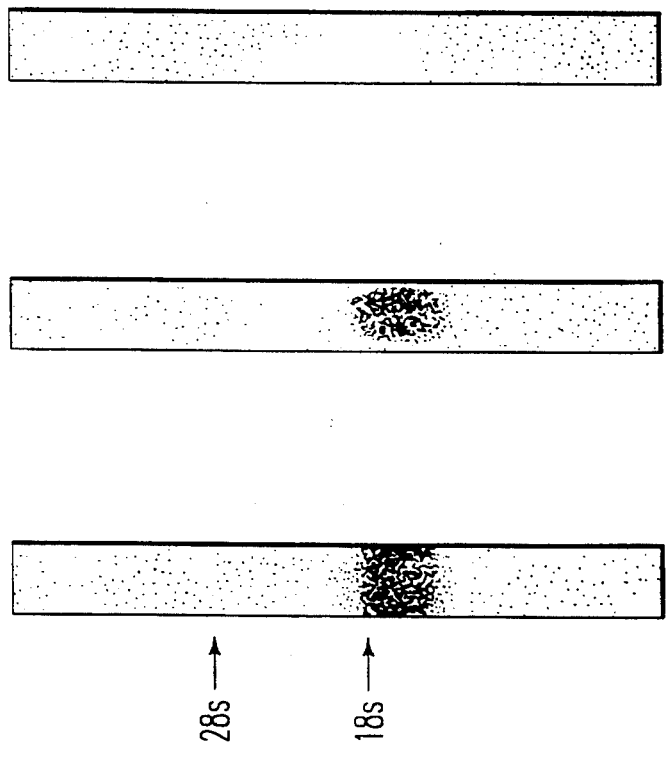
FIG. 4 illustrates the analysis of pBSF 2-38 CDNA insert b7 northern blot technique.

FIG. 4 shows a part of the same.

Thus, FIG. 4 is an autoradiogram taken by Northern blotting technique, wherein (a) is mRNA of VT-1 cells, (b) is mRNA of T-lymphocytes which were prepared by activating human tonsil cells (5×10$^6$ ml) with PHA 0.1%, TPA 5 ng for 40 hours, and (c) is mRNA of human tonsil cells which were not subjected to stimulation treatment.

EXAMPLE 7

Figure 6:
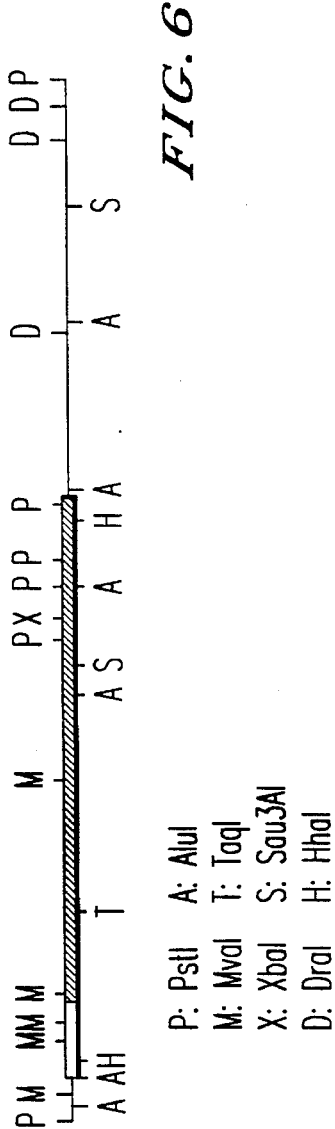
FIG. 6 shows a restriction enzyme cleavage map.

MC1061 containing pBSF 2-38 was treated in the same manner as in the Example 5, step (1) to obtain plasmid DNA which was cleaved with restriction enzyme Bam HI. BCDF cDNA was thus prepared. Restriction enzyme cleavage map and nucleotide sequence of the BCDF cDNA were examined. The nucleotide sequence was determined by the chemical method of Maxam-Gilbert (See; Meth. Enzym. 65, 499 (1980)) and by dideoxynucleotide chain terminating method (See; F. Sanger et al., Proc. Natl. Acad. Sci. U.S.A. 74, 5463 (1977)) using M13 phage (See; J. Messing et. al., Gene, 19, 269 (1982)). The nucleotide sequence and amino acid sequence thus determined are as shown in FIG. 5. The restriction enzyme cleavage map is as shown in FIG. 6.

The nucleotide sequence of human BCDF now determined, contains the same partial structure of the amino acid sequence as disclosed in Examples 1 and 2.

EXAMPLE 8

Figure 7:
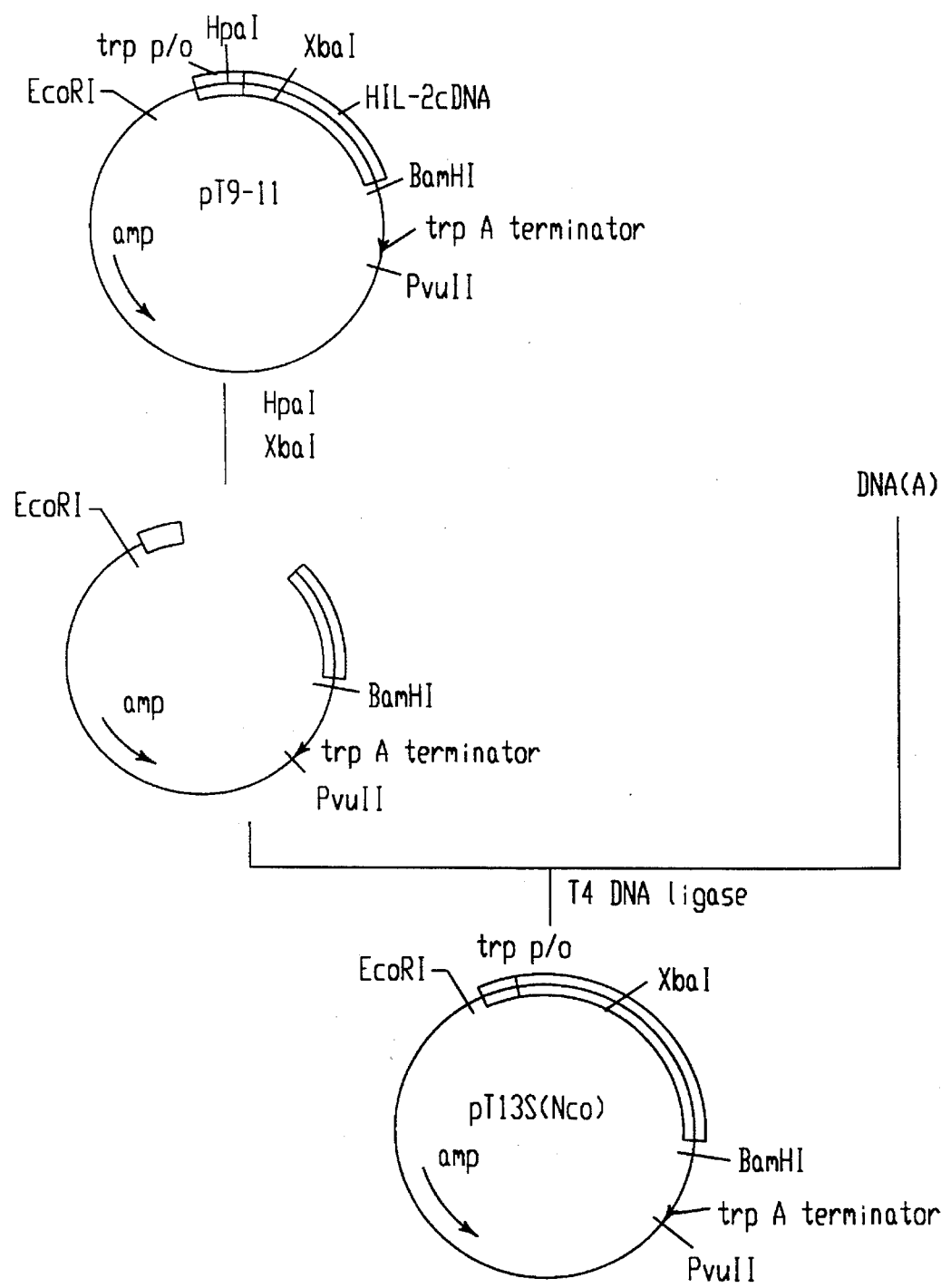
FIG. 7 illustrates the construction of plasmid pT13S(Nco).

(1) Vector to be used for expressing human BCDF genes was constructucted as follows: (See: FIG. 7)

Figure 8B:
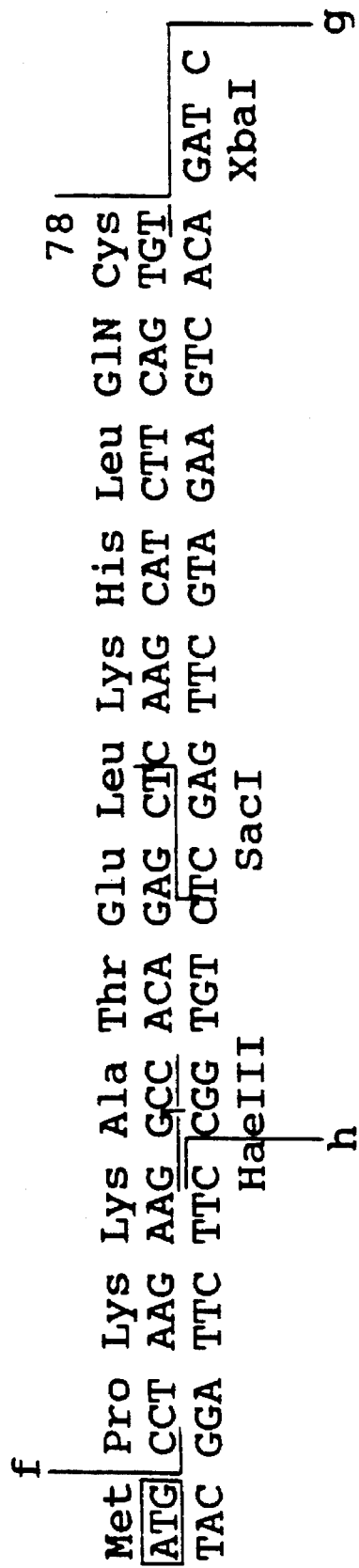
FIG. 8 shows the nucleotide sequence and restriction enzyme cleavage map of synthetic human interleukin-2 (HIL-2).

DNA fragments (a)→(l) containing the nucleotide sequence shown in FIG. 8 were synthesized by the solid phase phosphoric acid triester method. The DNA fragments, except (a) and (g), were treated with T4 polynucleotide kinase and ATP to phosphorylate the 5'-terminal.

DNA fragments (a)→(l) were combined and annealed, followed by treatment with T4 DNA ligase, so that double-stranded synthetic DNA (A) was formed. pT 9-11 (T. Sato et al, J. Biochem. 101, 525 (1987)) was cleaved with restriction enzymes HpaI and XbaI and the cleavage product was subjected to agarose gel electrophoresis, so that large DNA fragment was isolated. pT 9-11 fragment thus obtained was mixed with synthetic DNA (A) (See; FIG. 8) and ligated by the use of T4 DNA ligase. Recombinant DNA thus obtained ws introduced into the cells of *Escherichia coli* HB 101 strain, from which was selected ampicillin resistant strain. Plasmid obtained from the selected strain was cleaved with restriction enzymes, and the restriction enzyme map was examined. As the result, a strain which has pT13S(Nco) involving synthetic HIL-2cDNA was selected.

Figure 9:
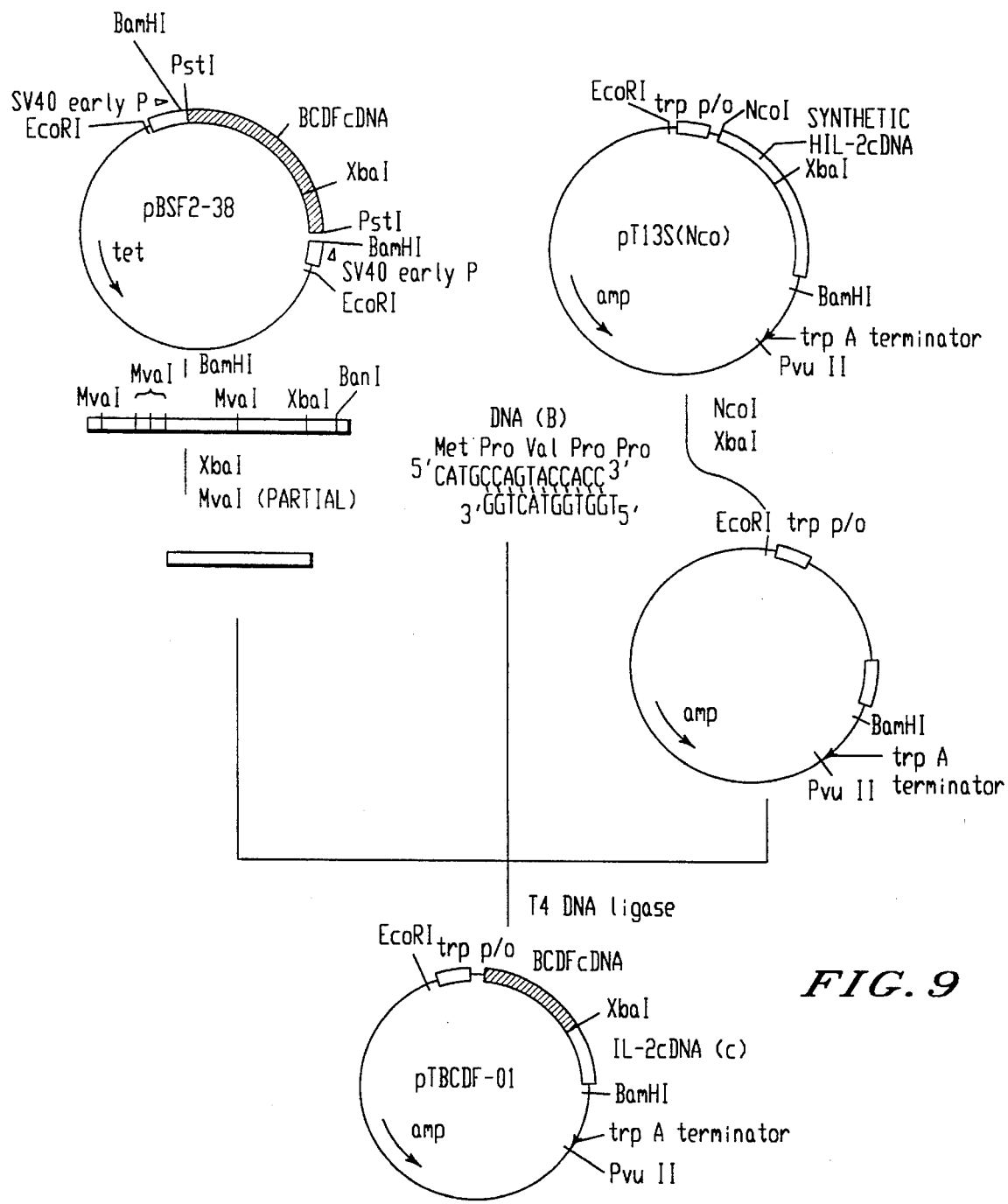
FIG. 9 shows the construction of plasmid pTBCDF-01.
Figure 10:
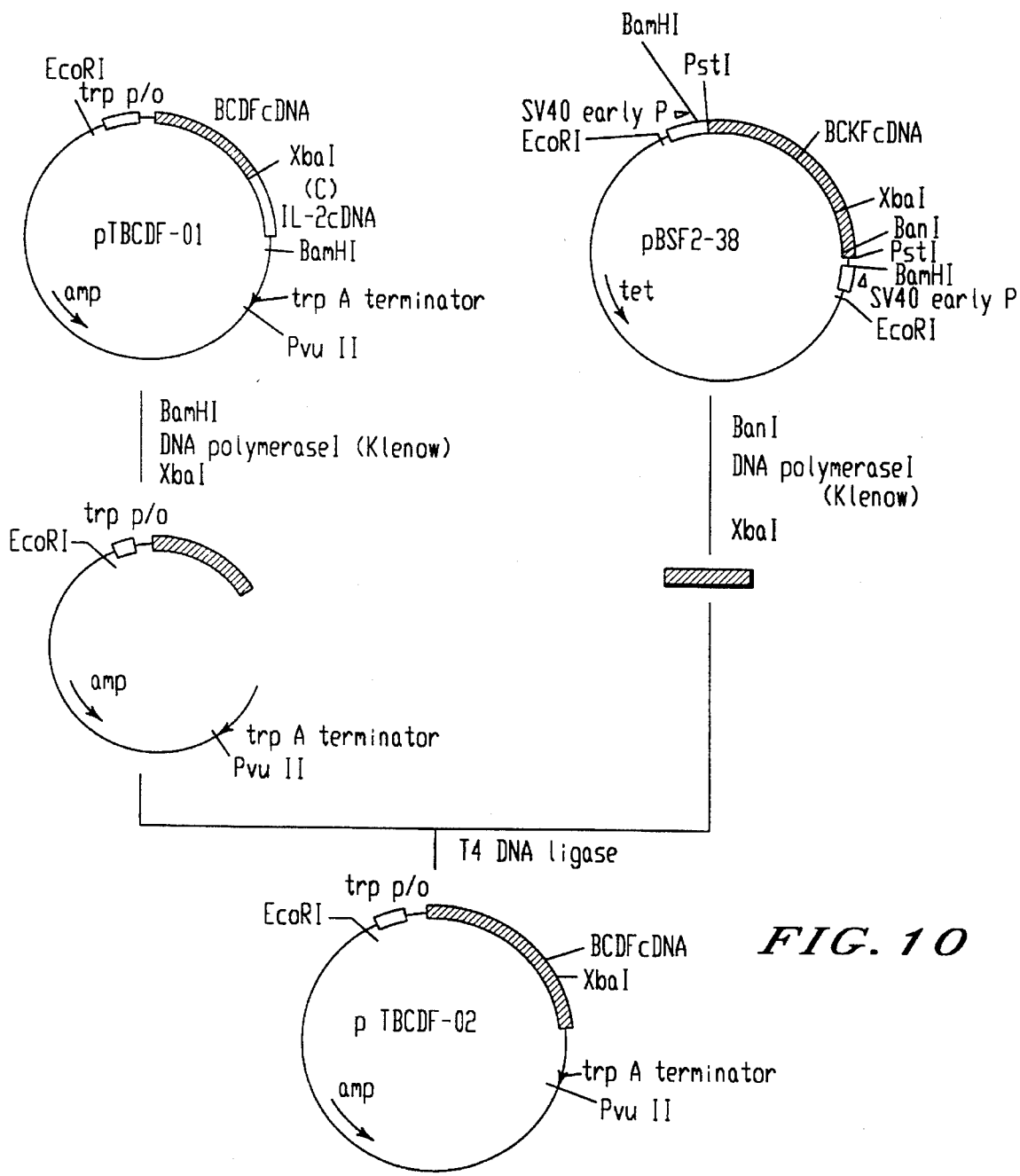
FIG. 10 shows the construction of plasmid pTBCDF-02.

(2) Recombinant DNA which-expresses human BCDF was constructed by the use of plasmid pT13S(Nco) and pBSF 2-38 (See FIG. 9 and 10):

(i) Plasmid pT13S(Nco) was cleaved with restriction enzymes NcoI and XbaI, and the cleavage products were subjected to agarose gel electrophoresis, so that larger DNA fragments were isolated in a purified form. Plasmid pBSF 2-38 was cleaved with restriction enzyme BamHI and the cleavage products were subjected to agarose gel electrophoresis, thereby smaller DNA fragments containing human BCDF cDNA insert were recovered. The human BCDF cDNA insert obtained through cleavage by the use of restriction enzyme BamHI as above was then cleaved completely by restriction enzyme Xba I, followed by partial cleavage by the use of restriction enzyme MvaI.

Next, a DNA mixture consisting of pT13S(Nco) fragment containing tryptophan promoter and operator (trp p/o) and MvaI-XbaI fragment from human BCDF cDNA was further combined with synthetic DNA(B) [$5'$CATGCCAGTAC-CACC$^{3'}$ and 5'-terminal phosphorylated $5''$TGGTGG-TACTGG$^{3'}$]. The resultant mixture was ligated by the use of T4 DNA ligase. The recombinant DNA thus obtained was introduced into the cells of *Escherichia coli* HB101, from which strains resistant against ampicillin were selected. The strains thus selected were screened by colony hybridization to select the strains having the DNA hybridizing with synthetic DNA (B). From the strains thus finally selected, was isolated plasmid DNA. The plasmid DNA was subjected to cleavage test with restriction enzymes and examined for the nucleotide sequence at the binding site. As the result, the strain containing pTBCDF-01 was selected. This strain was named pTBCDF-01/HB101.

(ii) Plasmid pBSF 2-38 was subjected to cleavage with restriction enzyme Ban I, treatment with DNA polymerase I (Klenow), cleavage with restriction enzyme XbaI and agarose gel electrophoresis, so that DNA fragments having about 150 base pairs were isolated.

(iii) pTBCDF-01 obtained in (i) above was subjected to cleavage with restriction enzyme Bam HI, treatment with DNA polymerase I (Klenow), cleavage with restriction enzyme XbaI and agarose gel electrophoresis, so that larger DNA fragments were recovered.

(iv) Two DNA fragments obtained (ii) and (iii) respectively were ligated by the use of T4 DNA ligase. The resultant recombinant DNA was introduced into the cells of Escherichia coli HB101, which were screened to select the strains resistant against ampicillin. From the strains thus selected, was isolated plasmid DNA which was subjected to cleavage test with restriction enzymes, to obtain the strain containing pTBCDF-2. This strain was named pTBCDF02/HB101, (FERM P-9061, FERM SP-1403).

(v) *Escherichia coli* HB101 strain containing plasmid pTBCDF-01 or pTBCDF-02 was cultured in L-broth (1% bactotrypton, 0.5% yeast extract, 0.5% NaCl, 0.1% glucose, pH 7.5) (10 ml) which further contains streptomycin (25 µg/ml) and ampicillin (25 µg/ml), at 37° C. overnight. 5 ml portion of the cultured suspension was inoculated in M9-casamino acid medium (0.6% $Na_2HPO_4.12H_2O$, 0.3% $KH_2PO_4$, 0.05% NaCl, 0.1% $NH_4Cl$, 0.05% $MgSO_4.7H_2O$, 0.00147% $CaC_2$, 0.2% glucose, 0.2% casamino acid, 0.02% L-leucine, 0.02% L-proline, 0.0002% thiamine hydrochloride, 100 µg/ml ampicillin, 25 µg/ml streptomycin, pH 7.4) and cultured at 28° C. for 3 hours. Thereafter, to the cultured mixture was added 3-indole acetate (IAA) (25 µg/ml), and the culture mixture was further cultured at 23° C. for 21 hours. The culture mixture was centrifuged to harvest the cells which was washed with 20 mM Tris-HCl buffer (pH 7.5) and NaCl (30 mM) and then was suspended in the buffer of the same composition (8 ml). The cells thus obtained was digested with (1%) sodium dodecyl sulfate (SDS) or (1 mg/ml) lysozyme in the presence of EDTA (50 mM), followed by sonication (50 W, 30 seconds), so that the proteins in the cells were isolated.

As shown in Table 1, both the isolated solution as prepared from the culture of the strain which has pTBCDF-01/HB101, which has a partial defect on the side of the 3'-terminus and to this defect is linked a part of human IL-2 cDNA, and the culture of the strain which has pTBCDF-02/HB101 containing BCDF cDNA coding whole human mature BCDF protein, showed BCDF activity as shown below:

TABLE 1

| BCDF activity (as determined by Reverse-Plaque method) of the extract prepared from the culture of the strain containing recombinant DNA | |
|---|---|
| Recombinant DNA (strain) | BCDF activity (U/ml) |
| pTBCDF-01/HB101 | 800 |
| pTBCDF-02/HB101 | 28,000 |

The recombinant BCDF was purified in the same manner as in the Example 1, and then was subjected to HPLC using Synchropak RP-P (C18). A single protein was eluted out at the acetonitrile concentration of 50→55%. On the protein thus isolated was examined the amino acid sequence in the same manner as in Example 1, thereby confirming the structure of the N-terminal sequence.

Thus, the polypeptide produced by pTBCDF-02/HB101 has the following amino acid sequence:

PRO VAL PRO PRO GLY GLU ASP SER LYS ASP VAL
ALA ALA PRO HIS ARG GLN PRO LEU THR SER SER
GLU ARG ILE ASP LYS GLN ILE ARG TYR ILE LEU
ASP GLY ILE SER ALA LEU ARG LYS GLU THR CYS
ASN LYS SER ASN MET CYS GLU SER SER LYS GLU
ALA LEU ALA GLU ASN ASN LEU ASN LEU PRO LYS
MET ALA GLU LYS ASP GLY CYS PHE GLN SER GLY
PHE ASN GLU GLU THR CYS LEU VAL LYS ILE ILE
THR GLY LEU LEU GLU PHE GLU VAL TYR LEU GLU
TYR LEU GLN ASN ARG PHE GLU SER SER GLU GLU
GLN ALA ARG ALA VAL GLN MET SER THR LYS VAL
LEU ILE GLN PHE LEU GLN LYS LYS ALA LYS ASN
LEU ASP ALA ILE THR THR PRO ASP PRO THR THR
ASN ALA SER LEU LEU THR LYS LEU GLN ALA GLN
ASN GLN TRP LEU GLN ASP MET THR THR HIS LEU
ILE LEU ARG SER PHE LYS GLU PHE LEU GLN SER
SER LEU ARG ALA LEU ARG GLN MET

EXAMPLE 9

Figure 11:
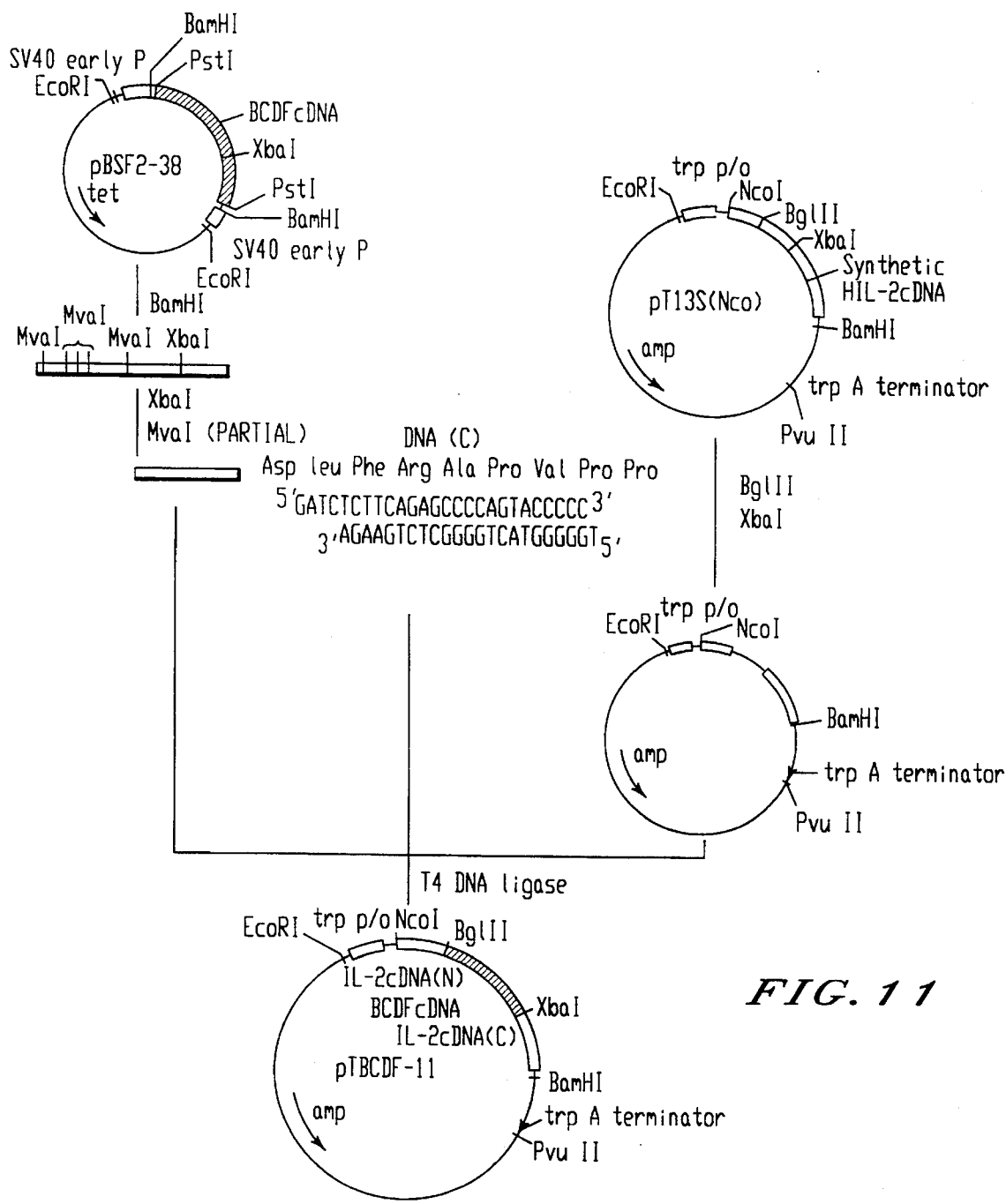
FIG. 11 shows the construction of plasmid pTBCDF11.
Figure 12:
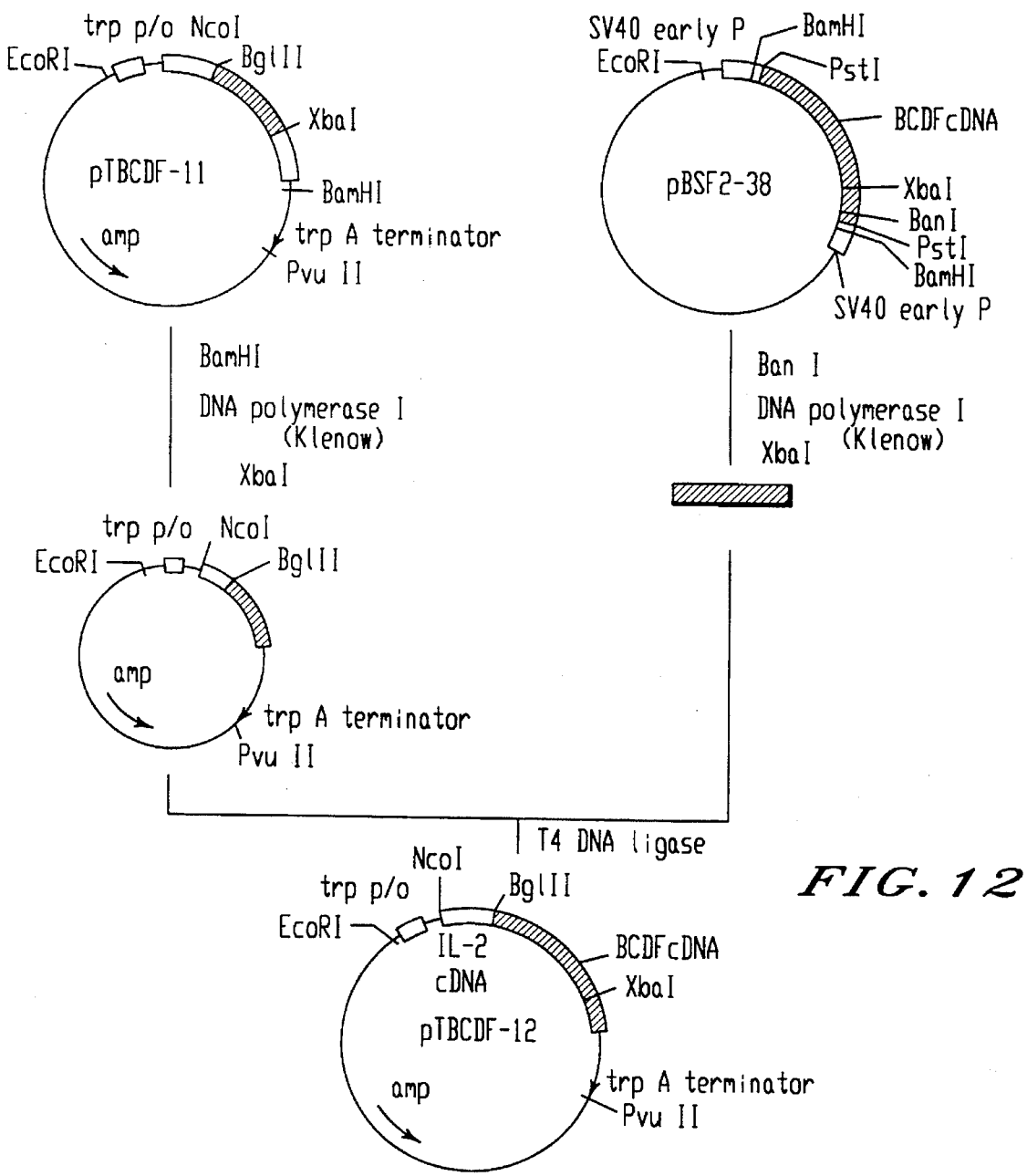
FIG. 12 shows the construction of plasmid pTBCDF12.

Construction of recombinant DNA capable of producing conjugated protein (ΔHIL-2-BCDF) of human BCDF with human interleukin-2 (HIL-2) by the use of plasmid pT13S(Nco) (as described in Example 8) and pBSF 2-38. (See FIG. 11 and 12): (i) Plasmid pT13S(Nco) was cleaved with restriction enzyme BglII and XbaI, and the cleavage product was subjected to agarose gel electrophoresis, so that larger DNA fragment was isolated. Plasmid pBSF 2-38 was cleaved with restriction enzyme BamHI, and the cleavage product was subjected to agarose gel electrophoresis, so that smaller DNA fragment containing human BCDF cDNA insert was isolated. The human BCDF cDNA insert obtained from BamHI cleaved was further treated with restriction enzyme XbaI, followed by partial cleavage with MvaI. A DNA mixture composed of pT13S(Nco) fragment containing the promoter mentioned above and MVaI - XbaI fragment containing human BCDF cDNA was combined with synthetic DNA(C)[5'GATCTCTTCAGAGCCCCAGTAC-CCCC3']. The mixture was ligated by the use of T4 DNA ligase.

The recombinant DNA thus obtained was introduced into the cells of *Escherichia coli* HB101, so that the strains resistant against ampicillin were selected. The strains were screened by colony hybridization to select the strain having DNA capably of hybridizing with synthetic DNA(C). Plasmid obtained from the strains selected as above was cleaved with restriction enzyme. On the plasmid, the nucleotide sequence of joining sites was examined. The strain containing pTBCDF-11 was thus obtained, which was named pTBCDF11/HB101.

(ii) Plasmid pBSF 2-38 was cleaved with restriction enzyme Ban I, and t-he cleavage product was subjected to treatment with DNA polymerase I (Klenow), cleavage with XbaI, and agarose gel electrophoresis, so that the DNA fragment of about 150 base pairs was isolated.

(iii) pTBCDF-11 obtained in (i) above was cleaved with restriction enzyme BamHI, and the cleavage product was subjected to treatment with DNA polymerase I (Klenow), cleavage with XbaI and agarose gel electrophoresis, so that larger DNA fragment was recovered.

(iv) The two DNA fragments obtained in (ii) and (iii) respectively were ligated by the use of T4 DNA ligase. The recombinant DNA thus obtained was introduced into the cells of *Escherichia coli* HB101, from which the strains resistant against ampicillin were selected. From the strains thus selected was isolated plasmid DNA which was subjected to cleavage test with restriction enzymes. The strain containing pTBCDF-12 was thus selected, which was named pTBCDF- 2/HB101/(FERM-P9062, FERM BP-1404).

(v) The strains of HB101, namely the HB101 containing plasmid pTBCDF-11 wherein the 5'-terminal of the BCDF cDNA is linked to a part of human IL-2 cDNA and a defect on the side of the 3'-terminus is linked to human IL-2 cDNA; and the HB101 containing plasmid pTBCDF-12 where the 5'-terminus of the whole BCDF cDNA covering mature BCDF protein is linked to DNA responsible to N-terminus amino acid protein in human IL-2 cDNA were cultured in the same manner as in Example 8. The culture was isolated in a conventional manner. The culture solution isolated from the two kinds of HB101 strains exhibit BCDF activity as demonstrated in Table 2 below.

TABLE 2

BCDF activity (as determined by Reverse-Plaque method) of the culture solution isolated from the culture of the strains containing recombinant DNA

| Recombinant DNA (Strain) | BCDF activity (U/ml) |
|---|---|
| pTBCDF-11/HB101 | 500 |
| pTBCDF-12/HB101 | >25,600 |

EXAMPLE 10

Cells of pTBCDF-12/HB101 (See Example 9) were cultured according to Example 8. The culture was processed in the following manner to isolate inclusion bodies formed in the cells.

Thus, the culture was centrifuged to collect the cells which were suspended at a 10-fold density of cells (as compared with the culture) in 20 mM Tris-HCl buffer (pH 7.5) containing 30 mM NaCl, to which were added lysozyme (1 mg/ml) and EDTA (0.05M), followed by stirring. The suspension was allowed to stand under ice-cooling for 1 hour, and was subjected to sonication to break (degrade) the cells. The suspension thus treated was centrifuged at 10000 rpm for 5 minutes, thereby the inclusion bodies were recovered.

The inclusion bodies were solubilized with the addition of 6M guanidine hydrochloride and the solution was adjusted to the final concentration of 100 μg/ml of ΔHIL-2-BCDF and 2M of guanidine hydrochloride. The suspension was admixed with oxidized glutathione (1 mM) and reduced glutathione (10 mM), adjusted to pH 8.0 and allowed to stand at room temperature for 10 to 16 hours. The suspension was then subjected to gel filtration (Sephadex G-25), so that guanidine hydrochloride was removed, and the fraction corresponding to ΔHIL-2-BCDF as a buffer solution for Kallikrein reaction. The fraction was subjected to SDS-polyacrylamide gel electrophoresis.

Molecular weight now determined by the electrophoresis nearly coincided with the value calculated based on its amino acid composition.

Examination of the N-terminal amino acid sequence by means of a protein sequencer showed that it corresponds to that of HIL-2.

The polypeptide having the BCDF activity is represented by the following amino acid sequence:

| | | | | | | | | | | |
|---|---|---|---|---|---|---|---|---|---|---|
| ALA | PRO | THR | SER | SER | SER | THR | LYS | LYS | THR | GLN |
| LEU | GLN | LEU | GLU | HIS | LEU | LEU | LEU | ASP | LEU | PHE |
| ARG | ALA | PRO | VAL | PRO | PRO | GLY | GLU | ASP | SER | LYS |
| ASP | VAL | ALA | ALA | PRO | HIS | ARG | GLN | PRO | LEU | THR |
| SER | SER | GLU | ARG | ILE | ASP | LYS | GLN | ILE | ARG | TYR |
| ILE | LEU | ASP | GLY | ILE | SER | ALA | LEU | ARG | LYS | GLU |
| THR | CYS | ASN | LYS | SER | ASN | MET | CYS | GLU | SER | SER |
| LYS | GLU | ALA | LEU | ALA | GLU | ASN | ASN | LEU | ASN | LEU |
| PRO | LYS | MET | ALA | GLU | LYS | ASP | GLY | CYS | PHE | GLN |

-continued

| SER | GLY | PHE | ASN | GLU | GLU | THR | CYS | LEU | VAL | LYS |
|-----|-----|-----|-----|-----|-----|-----|-----|-----|-----|-----|
| ILE | ILE | THR | GLY | LEU | LEU | GLU | PHE | GLU | VAL | TYR |
| LEU | GLU | TYR | LEU | GLN | ASN | ARG | PHE | GLU | SER | SER |
| GLU | GLU | GLN | ALA | ARG | ALA | VAL | GLN | MET | SER | THR |
| LYS | VAL | LEU | ILE | GLN | PHE | LEU | GLN | LYS | LYS | ALA |
| LYS | ASN | LEU | ASP | ALA | ILE | THR | THR | PRO | ASP | PRO |
| THR | THR | ASN | ALA | SER | LEU | LEU | THR | LYS | LEU | GLN |
| ALA | GLN | ASN | GLN | TRP | LEU | GLN | ASP | MET | THR | THR |
| HIS | LEU | ILE | LEU | ARG | SER | PHE | LYS | GLU | PHE | LEU |
| GLN | SER | SER | LEU | ARG | ALA | LEU | ARG | GLN | MET |     |

(2) Cleavage with Kallikrein

ΔHIL-2-BCDF (80 μg) as obtained above was reacted with human plasma kallikrein (73.5 μg) in 50 mM Tris-HCl buffer solution (pH 7.8) containing NaCl (113 mM) at 37° C. for 16 hours. The reaction mixture was subjected to reverse phase HPLC, thereby the fractions corresponding to human Ala-BCDF as eluted at the concentration of about 55% with respect to acetonitrile and 0.1% with respect to TFA were collected. On the fraction thus obtained the amino acid sequence at the N-terminal was examined by the use of a protein sequencer. As the result, it was confirmed that ΔHIL-2-BCDF had been transferred (converted) quantitatively into human Ala-BCDF protein. Human Ala-BCDF was recovered in a yield of 18.03 mg (recovery: 84%). "Human Ala-BCDF" is referred to as a natural human BCDF in which the N-terminal is linked to one alanine molecule and which has the following amino acid sequence:

| ALA | PRO | VAL | PRO | PRO | GLY | GLU | ASP | SER | LYS | ASP |
|-----|-----|-----|-----|-----|-----|-----|-----|-----|-----|-----|
| VAL | ALA | ALA | PRO | HIS | ARG | GLN | PRO | LEU | THR | SER |
| SER | GLU | ARG | ILE | ASP | LYS | GLN | ILE | ARG | TYR | ILE |
| LEU | ASP | GLY | ILE | SER | ALA | LEU | ARG | LYS | GLU | THR |
| CYS | ASN | LYS | SER | ASN | MET | CYS | GLU | SER | SER | LYS |
| GLU | ALA | LEU | ALA | GLU | ASN | ASN | LEU | ASN | LEU | PRO |
| LYS | MET | ALA | GLU | LYS | ASP | GLY | CYS | PHE | GLN | SER |
| GLY | PHE | ASN | GLU | GLU | THR | CYS | LEU | VAL | LYS | ILE |
| ILE | THR | GLY | LEU | LEU | GLU | PHE | GLU | VAL | TYR | LEU |
| GLU | TYR | LEU | GLN | ASN | ARG | PHE | GLU | SER | SER | GLU |
| GLU | GLN | ALA | ARG | ALA | VAL | GLN | MET | SER | THR | LYS |
| VAL | LEU | ILE | GLN | PHE | LEU | GLN | LYS | LYS | ALA | LYS |
| ASN | LEU | ASP | ALA | ILE | THR | THR | PRO | ASP | PRO | THR |
| THR | ASN | ALA | SER | LEU | LEU | THR | LYS | LEU | GLN | ALA |
| GLN | ASN | GLN | TRP | LEU | GLN | ASP | MET | THR | THR | HIS |
| LEU | ILE | LEU | ARG | SER | PHE | LYS | GLU | PHE | LEU | GLN |
| SER | SER | LEU | ARG | ALA | LEU | ARG | GLN | MET |     |     |

(3) Removal of the N-terminal Ala by the use of amino peptidase P

Amino peptidase P to be used for this purpose was purified according to the method as described in "Methods Enzymol. 19, 521 (1970)".

A solution of human Ala-BCDF as obtained in (2) above was subjected to gel filtration on a column of Sephadex G-25 which had been equilibrated with (50 mM) Tris-HCl buffer solution (pH 8.0) containing MnCl₂ (0.4 mM), so that Ala-BCDF fractions were obtained. The fraction of Ala-BCDF (50 μg) was admixed with amino peptidase P, and the mixture was allowed to react at 37° C. for 16 hours. After the reaction, the reaction mixture was subjected to reverse phase HPLC, so that the fractions corresponding to BCDF were collected. The N-terminal amino sequence of the fraction thus obtained was examined by the use of a protein sequencer. As a result, it was confirmed that the Ala-BCDF had been converted quantitatively into BCDF. Table 3 below shows the activity of Ala-BCDF and BCDF.

TABLE 3

| BCDF activity as exhibited by pTBCDF-12/HB101 (Reverse-plaque method) | |
|---|---|
| Protein produced | BCDF activity (U/μg protein) |
| Ala-BCDF | 20,000 |
| BCDF | 20,000 |

EXAMPLE 11

Figure 13:
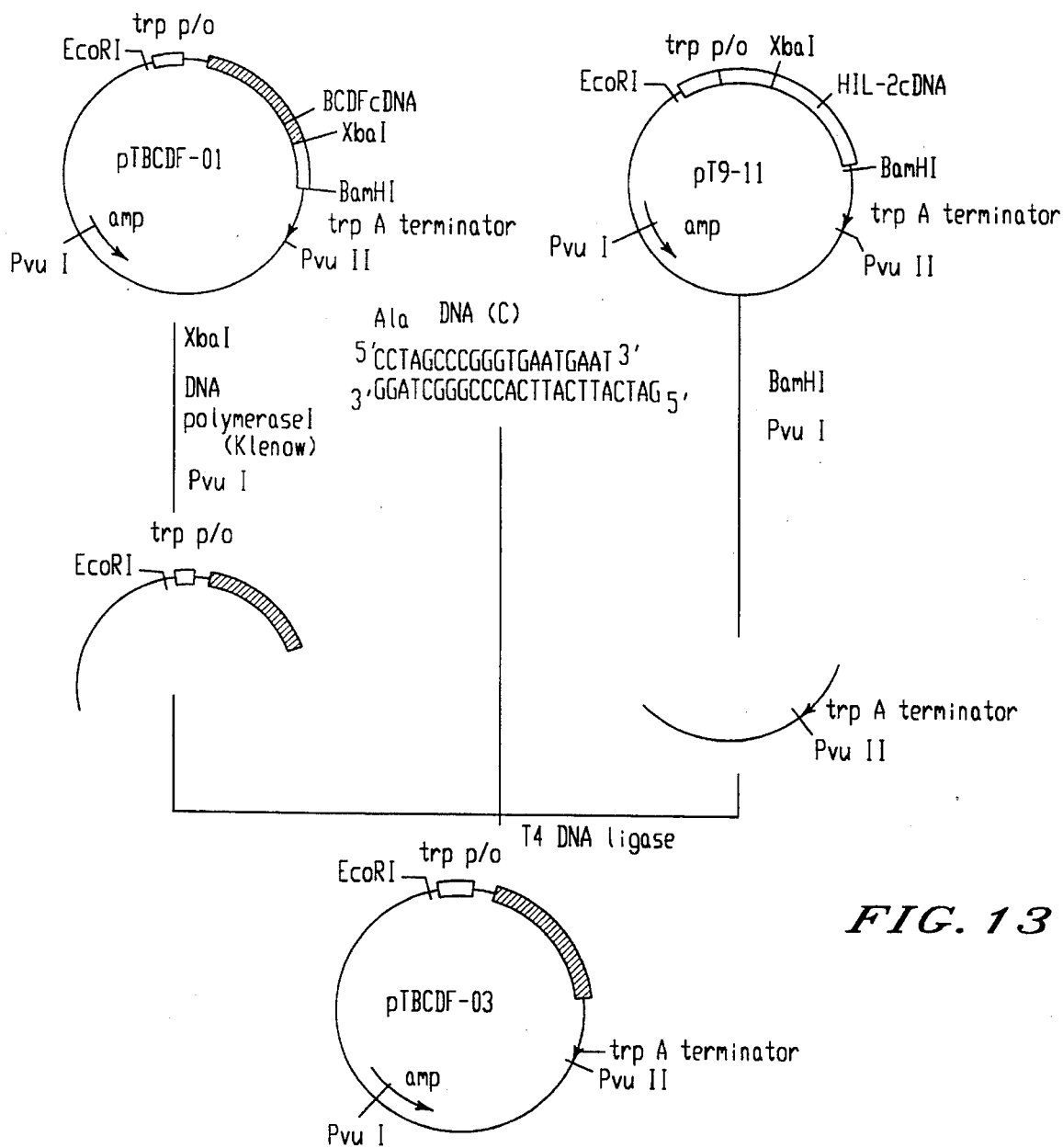
FIG. 13 shows the construction of plasmid pTBCDF03.

Construction of the recombinant DNA, capable of expressing human BCDF, lacking the C-terminus was prepared by the use of plasmids pTBCDF-1 and pT9-11. (See; FIG. 13):

(i) Plasmid pTBCDF-01 was cleaved with restriction enzyme XbaI, the cleavage product being subjected to DNA polymerase I (Klenow) treatment, cleavage with PvuI, and agarose gel electrophoresis, so that smaller DNA fragment containing trp P/O and human BCDF cDNA lacking the 3'-terminus. Plasmid pT9-11 was cleaved with restriction enzyme Bam HI and PvuI, and the cleavage product was subjected to agarose gel electrophoresis, so that larger DNA fragment containing trpA terminator was recovered.

The two kinds of DNA fragments thus prepared were mixed together with synthetic DNA (c) [5'CCTAGC-CCGGGTGAATGAAT3' and 5'GATCATTCATTCAC-CCGGGCTAGG3'], and the mixture was ligated by the use of T4 DNA ligase. The recombinant DNA thus prepared was introduced into the ampicillin cells of Escherichia coli HB101, so that ampicillin resistant strain was selected. From the strain was isolated plasmid DNA which was then cleaved with restriction enzyme. On the cleavage product was examined the nucleotide sequence around the linking site, so that the strain containing pTBCDF-03 was selected. The strain was named pTBCDF-03/HB101. The plasmid pTBCDF-03 contains a gene which lacks a part of the 3'-terminal of BCDF cDNA. The polypeptide as isolated from pTBCDF-03/HB101 has the following amino acid sequence;

| PRO | VAL | PRO | PRO | GLY | GLU | ASP | SER | LYS | ASP | VAL |
|-----|-----|-----|-----|-----|-----|-----|-----|-----|-----|-----|
| ALA | ALA | PRO | HIS | ARG | GLN | PRO | LEU | THR | SER | SER |
| GLU | ARG | ILE | ASP | LYS | GLN | ILE | ARG | TYR | ILE | LEU |
| ASP | GLY | ILE | SER | ALA | LEU | ARG | LYS | GLU | THR | CYS |
| ASN | LYS | SER | ASN | MET | CYS | GLU | SER | SER | LYS | GLU |
| ALA | LEU | ALA | GLU | ASN | ASN | LEU | ASN | LEU | PRO | LYS |
| MET | ALA | GLU | LYS | ASP | GLY | CYS | PHE | GLN | SER | GLY |
| PHE | ASN | GLU | GLU | THR | CYS | LEU | VAL | LYS | ILE | ILE |
| THR | GLY | LEU | LEU | GLU | PHE | GLU | VAL | TYR | LEU | GLU |
| TYR | LEU | GLN | ASN | ARG | PHE | GLU | SER | SER | GLU | GLU |
| GLN | ALA | ARG | ALA | VAL | GLN | MET | SER | THR | LYS | VAL |
| LEU | ILE | GLN | PHE | LEU | GLN | LYS | LYS | ALA | LYS | ASN |
| LEU | ALA | | | | | | | | | |

(ii) The pTBCDF-03/HB101 was treated in the same manner as in Example 8 to prepare an isolated culture solution. As shown in Table 4, the culture solution of the pTBCDF-03/HB101 shows BCDF activity.

TABLE 4

| BCDF activity of the culture solution isolated from the strain containing recombinant DNA (Reverse-plaque method) | |
|---|---|
| Strain | BCDF activity (U/ml) |
| pTBCDF-03/HB101 | 400 |

EXAMPLE 12

The same procedures were applied as in Example 10, step (1) to (3), except that in step (3) Ala-BCDF was used in the quantity of 2.02 mg.

The human BCDF was recovered in a yield of 2.0 mg. Table 5 shows the activity of human BCDF and of human Ala-BCDF. The activity is represented by the unit value as defined according to the method of Proc. Natl. Acad, Sci. USA, 82, 5490 (1985).

TABLE 5

| | BCDF activity (U/ml) | Specific activity (U/µg) |
|---|---|---|
| Human Ala-BCDF | 3,500,000 | 5,000 |
| Human BCDF | 1,500,000 | 2,500 |

(4) Formulation of human BCDF

The solution of the fractions containing human BCDF or human Ala-BCDF obtained by HPLC was allowed to stand at −20° C. overnight. The lower layer of the solution separated from the upper layer (acetonitrile) was subjected to gel filtration on Sephadex G-25 or dialysis, the remaining acetonitrile and TFA in the lower layer being removed, so that the solution was converted into a PBS solution. The solution thus prepared was diluted and was optionally admixed with (10%) fetal bovine serum (FBS) or with (0.1%) human serum albumin. The для mixture was filtered for sterile conditions, and finally was fomulated into pharmaceutically suitable forms.

EXAMPLE 13

The effect of human BCDF or human Ala-BCDF on the production of specific antibody was examined as follows:

The cells ($1 \times 10^4$) of human B cell line SKW6-CL4 were suspended in RPMI 1640 medium (100 µl) containing (10%) FBS, to which was added serial dilutions (2-fold) (100 µl) of human BCDF (79 ng/ml) or human Ala-BCDF (57 ng/ml). The suspension was cultured on a plate (96 well) (Corning Corp. 25860) at 37° C. in 5% $CO_2$ for 3 days. IgM in the supernatant was assayed according to the ELISA method (See; Proc. Natl. Acad. Sci. USA, 82, 5490 (1985).

Figure 14:
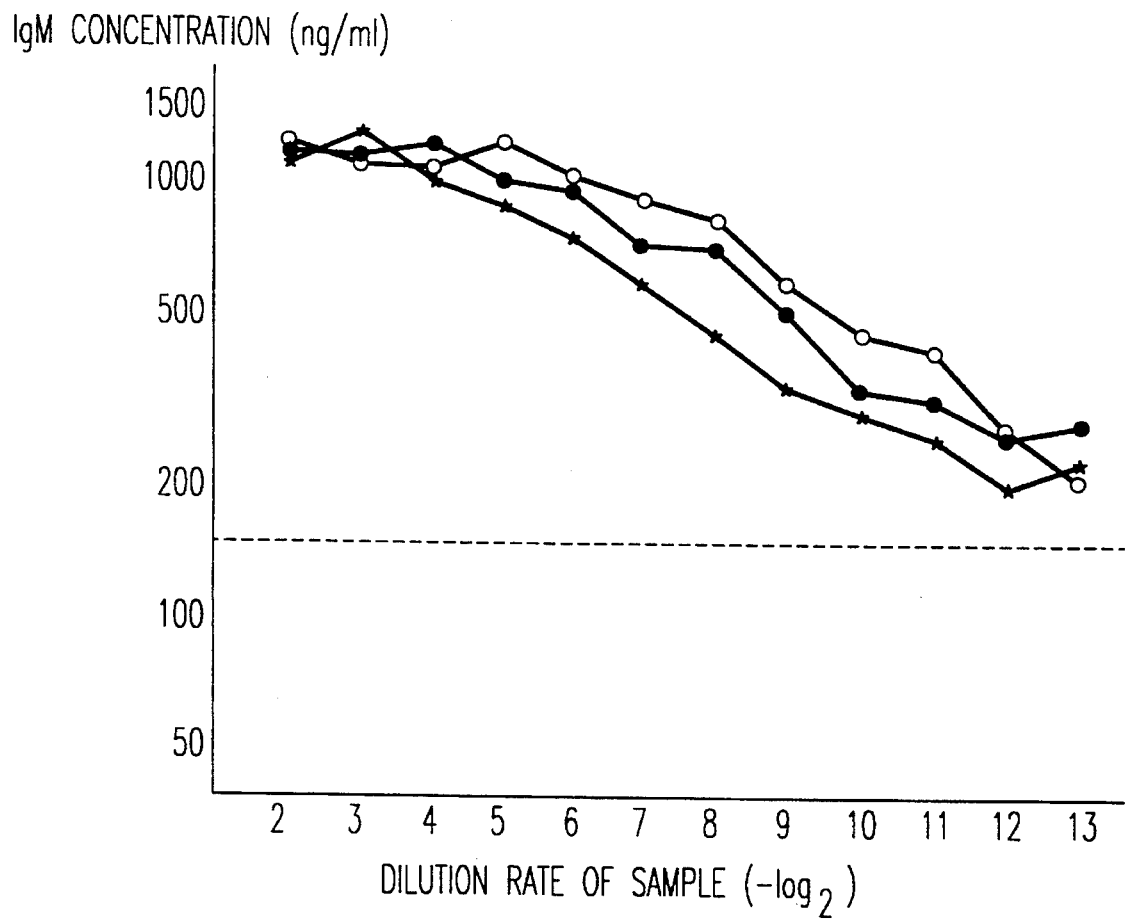
FIG. 14 illustrates the antibody production in human B cell line SKW6-CL4, enhanced by the introduction of human Ala-BCDF or human BCDF.

As shown in the FIG. 14, SKW6-CL4 cells cultured together with human BCDF or human Ala-BCDF exhibit a significantly elevated production of antibody (IgM), as compared with the control. There was not observed a statistically significant difference in the antibody production between human BCDF and human Ala-BCDF.

Human Ala-BCDF of known activity which was prepared by IL-2 fusion protein method was diluted into the portions (each 100 U/ml) which was used as BCDF standard.

EXAMPLE 14

Cells of SKW6-CL4 were cultured with human BCDF (1 U/ml) (200 pg/ml) and human recombinant IL-2 (50,000 U/ml) 1 µg/ml to 0.32 pg/ml) under the same condition as in the Example 13, for 3 days.

Figure 15:
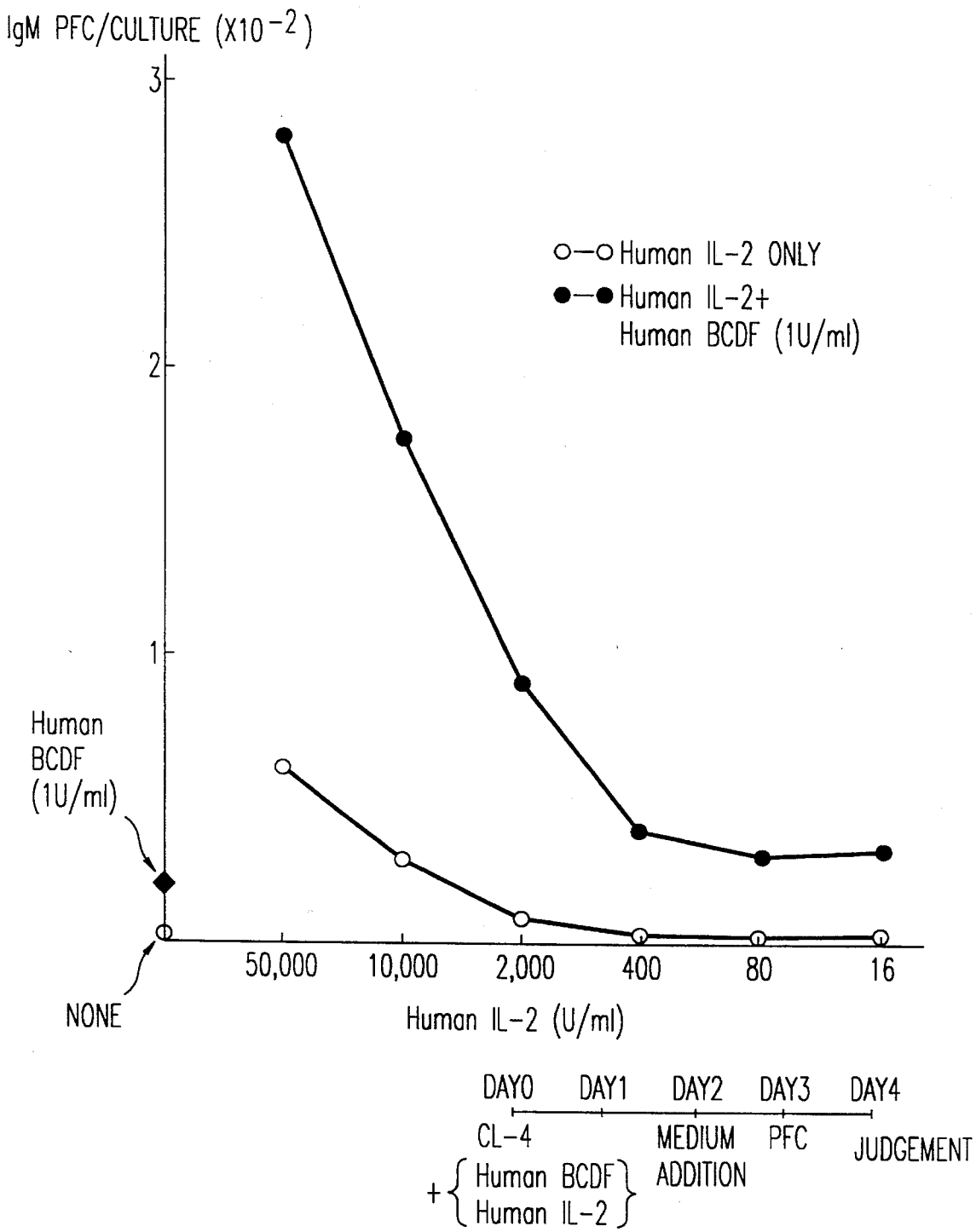
FIG. 15 illustrates that antibody production in human B cell line SKW6-CL4 is induced by the addition of human BCDF.

The number of cells which were differentiated into the cells to produce antibody were enumerated by Reverse PFC method (Eur. J. Immunol, 13, 31 (1983)). As shown in FIG. 15, the cells of SKW6-CL4 when cultured in the presence of human BCDF and human IL-2 added simultaneously exhibit an enhanced production of the antibody, as compared with the cells cultured in the presence of human BCDF or human IL-2 each added singly. The same result was also observed in ELISA method.

EXAMPLE 15

Spleen cells of DBA/2 mouse (female, 8 weeks old) were treated with 0.9% $NH_4$ Cl in a conventional manner to remove erythrocytes therefrom. The cells were then treated with anti-Thy 1 antibody and guinea pig complement to remove T-cells, so that B cells fraction obtained in a purified form.

The B cells fraction thus obtained ($7.5 \times 10^5$) and sheep red blood cell (SRBC) ($1 \times 10^5$) were suspended in RPMI 1640 medium (200 µl) containing (5%) FBS. The suspension was cultured on a plate (96 well) (Corning Corp. 25860) at 37° C. in 5% $CO_2$ for 4 to 5 days. During the cultivation, human BCDF (125 U/ml: 50 ng/ml) and human IL-2 (400 U/ml: 8 ng/ml) were added suitably to the culture at different intervals.

After the cultivation, the cells capable of producing anti-SRBC antibody were enumerated by PFC method (The Method of Immunological Experiment, P.479; Jap. Soc. Immunology).

Figure 16:
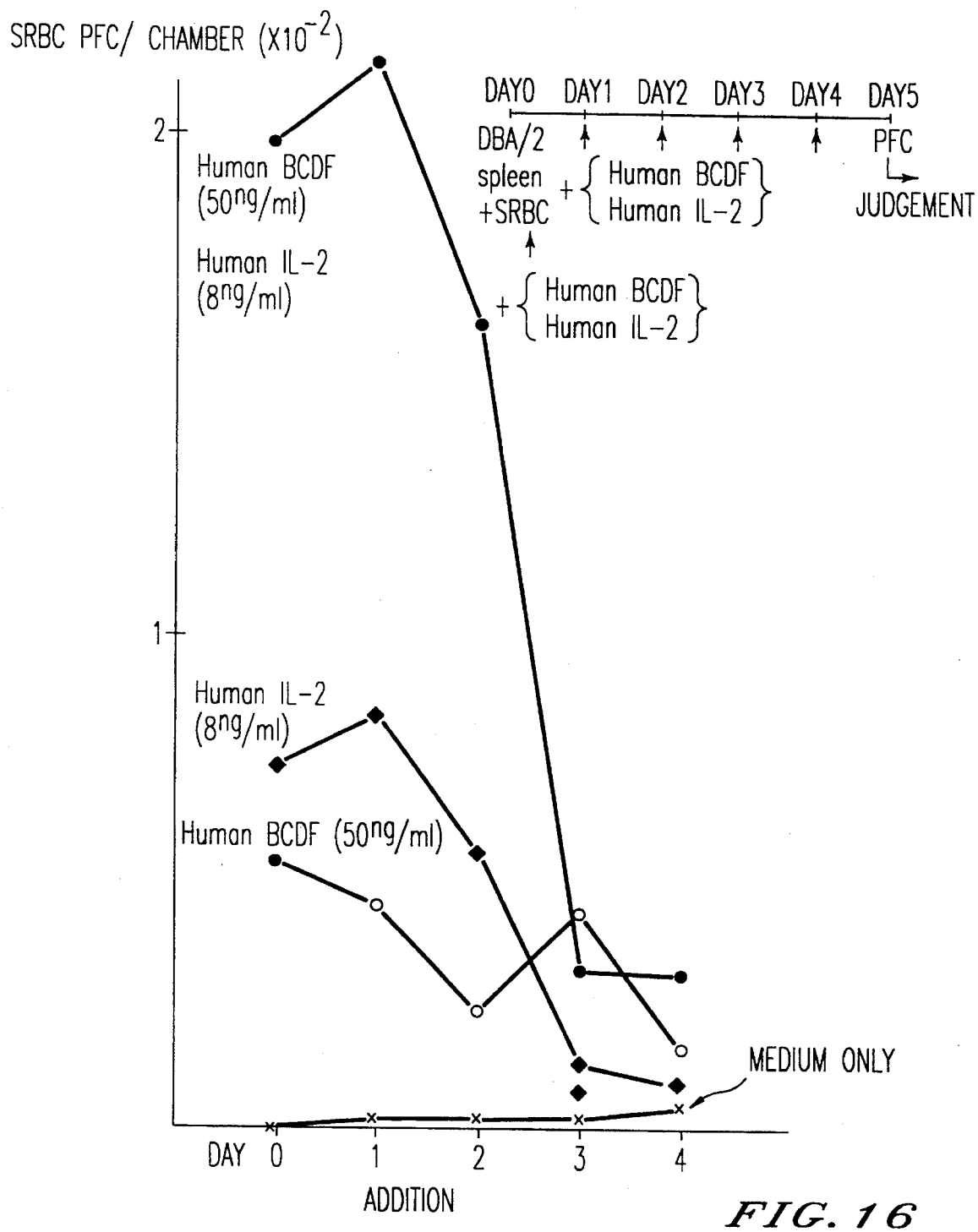
FIG. 16 illustrates that antibody production in DBA/2 mouse spleen cells is enhanced by the combined addition of human BCDF and human IL-2.
Figure 17:
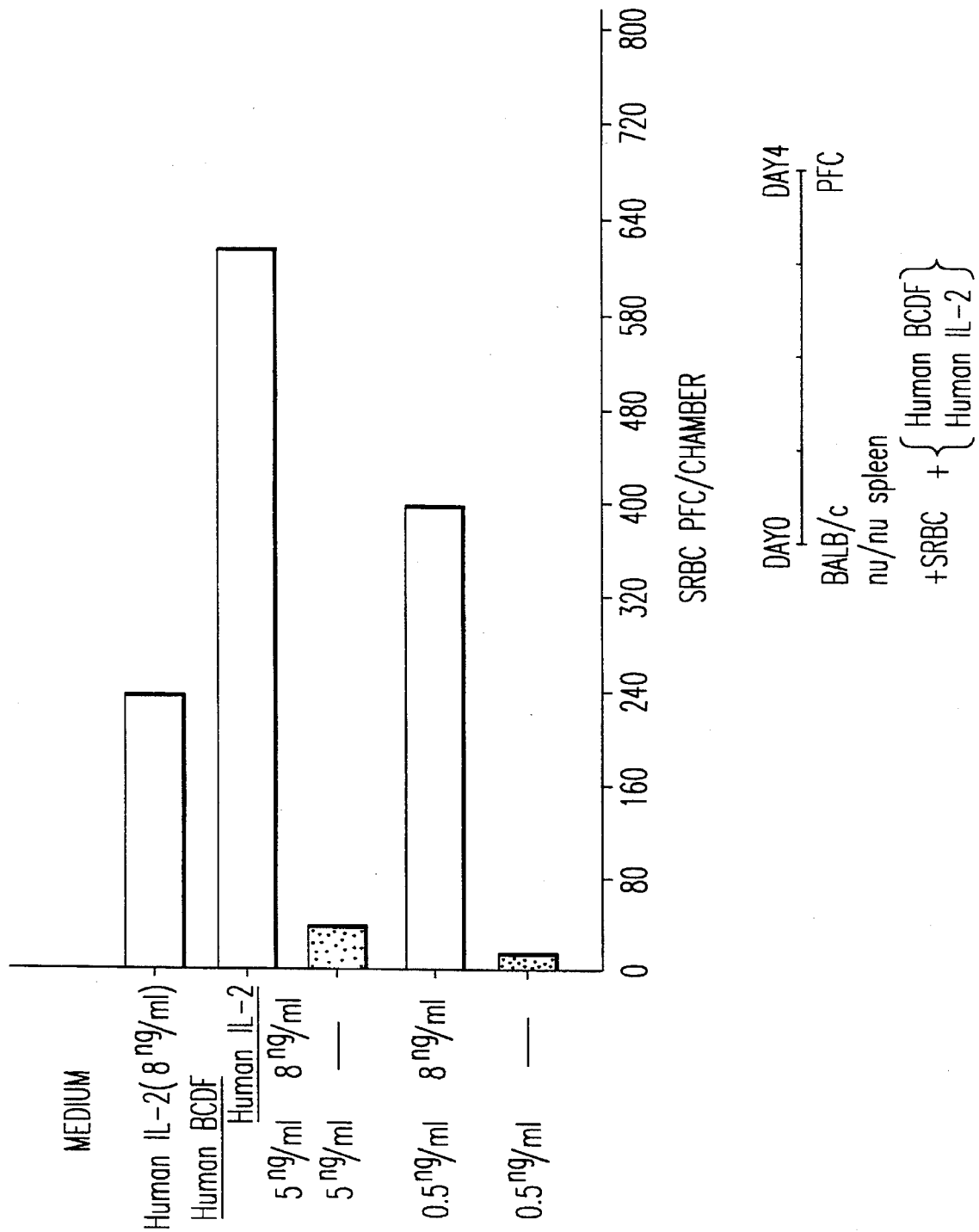
FIG. 17 illustrates that antibody production in the spleen cells of Balb/c nude mouse is enhanced by the combined addition of human BCDF and human IL-2.

As shown in FIG. 16, human BCDF stimulates the production of specific antibody in spleen cells of the normal mouse. The effect was further strengthened by the combined application of human BCDF and human Il-2. The same effect was observed in other strains of mouse, for example in Balb/c mouse. The test for the spleen cells derived from Balb/c nu/nu mouse which had lost T-cell function because of the lack of the thymus, gave also the same result as shown in the FIG. 17.

EXAMPLE 16

SRBC ($1\times10^8$) as antigen was injected intravenously to the tail of DBA/2 mouse (female, 8 weeks old), so that the DBA/2 mouse was sensitized. Four days after, the spleen was removed out from the sensitized mouse. The spleen was treated according to the method described in Example 15 to prepare sensitized B cells fractions in a purified form. The sensitized B cells ($7.5\times10^5$) and antigen SRBC ($1\times10^5$) as antigen were suspended in RPMI 1640 medium (200 ml) containing FBS (5%) and the suspension was cultured at 37° C. in the presence of human BCDF (50 ng/ml) and human IL-2 (8 ng/ml to 80 pg/ml) in 5% $CO_2$ for 4 days. The cells capable of producing anti-SRBC antibody were enumerated directly according to PFC method.

Figure 18:
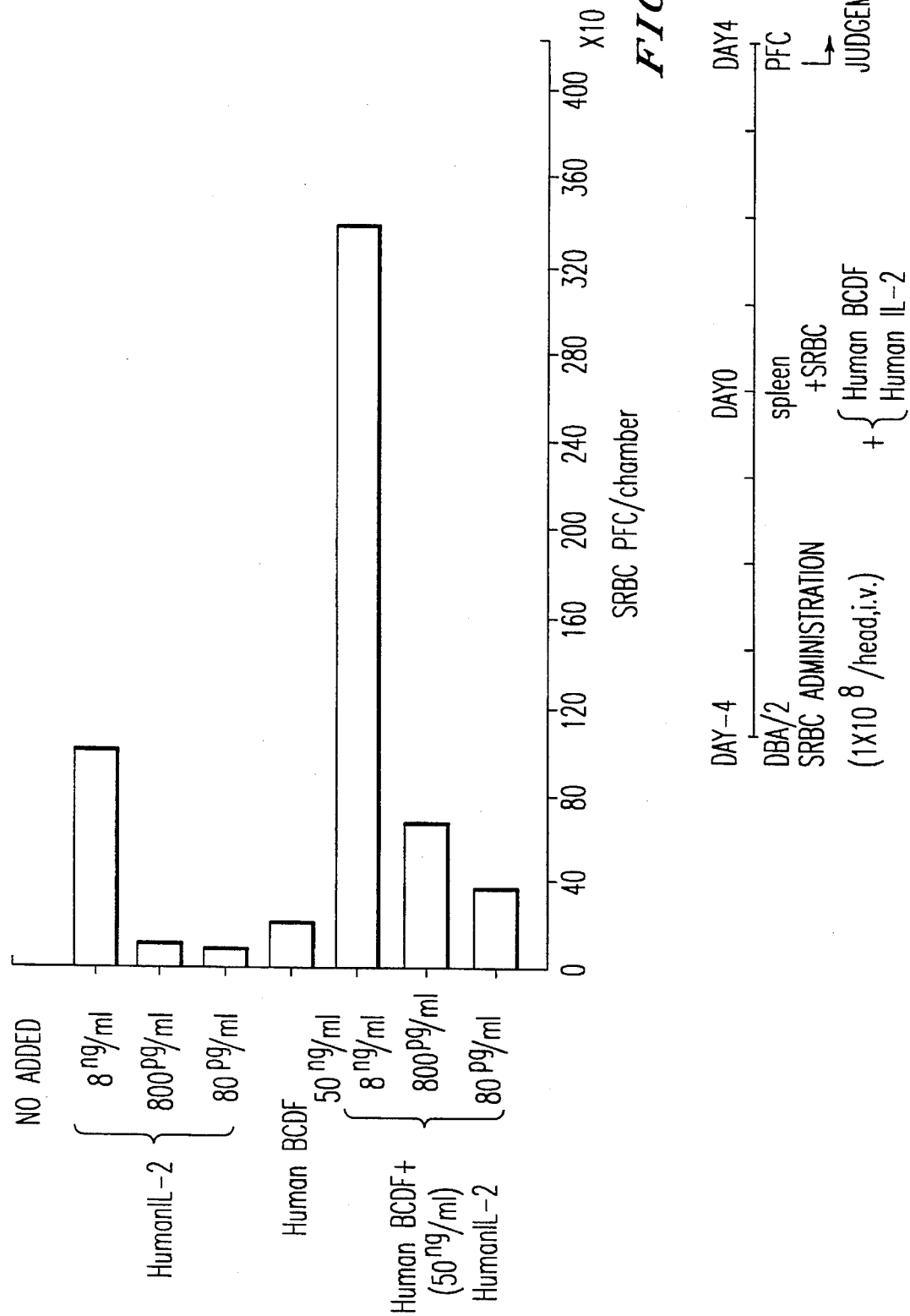
FIG. 18 illustrates that antibody production against the immunized antigen in vivo is enhanced by the combined addition of human BCDF and human IL-2.

As shown in FIG. 18, addition of human BCDF causes a statistically significant increase in the production of the specific antibody, as compared with the control (without the addition of human BCDF). The effect of the human BCDF on the productivity of the specific antibody was further strengthened when the human BCDF was applied together with human Il-2.

EXAMPLE 17

(1) Enhancement of production of the antibody against the antigen sensitized in vitro Immuno-suppresive drug, hydrocortisone (HC) (Trade mark of aqueous suspension of hydrocortisone acetate, Shuroson F, Japan Shering) (5 mg) was injected subcutaneously to Balb/c mouse (female, 6 weeks old), so that the mouse was immunosuppressed.

1, 2 and 7 days after, the spleen was removed from the immunosuppressed mouse. The spleen was treated with (0.9%) $NH_4$ Cl to remove red blood cells, so that purified spleen cells were prepared.

The spleen cells thus prepared ($5\times10^5$) and SRBC ($1\times10^5$) were suspended in RPMI 1640 medium (200 µl) containing FBS (5%), and the suspension was cultured on a plate (96 well) (Corning Corp. 25860) at 37° C. in 5% $CO_2$. To the culture medium were added human Ala-BCDF (25 U/ml; 4 ng/ml), human IL-2 (400 U/ml; 8 ng/ml) or T cell factor (TF; culture supernatant of hybridoma prepared from T cell stimulated with concanavalin A) (10%) as a positive control. On the 5th day of the cultivation, the cells were recovered in a conventional manner. The cells producing anti-SRBC antibody were enumerated directly according to PFC method.

As shown in the Table 6, the productivity of the specific antibody in the mouse where the formation of PFC at the addition of TF had been reduced by the hydrocortisone applied, as compared with the control, was enhanced by the addition of human Ala-BCDR and also in combination with human Il-2.

TABLE 6

| Treatment | SRBC | Lymphokine | PFC/$1 \times 10^6$ Spleen cells |
|---|---|---|---|
| HC untreated mouse | (−) | (−) | 0 |
|  | (+) | (−) | 2 |
|  | (+) | TF | 325 |
|  | (+) | human IL-2 | 26 |
|  | (+) | human Ala-BCDF | 14 |
|  | (+) | human IL-2 + human Ala-BCDF | 35 |
| One day after HC treatment | (+) | (−) | 0 |
|  | (+) | TF | 250 |
|  | (+) | human IL-2 | 6 |
|  | (+) | human Ala-BCDF | 38 |
|  | (+) | human IL-2 + human Ala-BCDF | 23 |
| 4 days after HC treatment | (+) | (−) | 5 |
|  | (+) | TF | 111 |
|  | (+) | human IL-2 | 18 |
|  | (+) | human Ala-BCDF | 54 |
|  | (+) | human IL-2 + human Ala-BCDF | 83 |
| 7 days after HC treatment | (+) | (−) | 14 |
|  | (+) | TF | 152 |
|  | (+) | human IL-2 | 6 |
|  | (+) | human Ala-BCDF | 2 |
|  | (+) | human IL-2 + human Ala-BCDF | 38 |

(2) Enhancement of production of the antibody against the antigen sensitized in vivo Hydrocortisone (0.5 mg) was injected subcutaneously to Balb/c mouse (female, 6 weeks old), and 7 days after, SRBC ($1\times10^8$) was injected intravenously to the tail of the mouse. On the 3 days after the injection, spleen was removed from the mouse, and the spleen was treated in the same manner as in (1) above to prepare the spleen cells. The cells producing specific anti-SRBC antibody were enumerated directly according to the PFC method.

The spleen cells ($5\times10^5$) was cultured together with SRBC ($1\times10^5$) in the same manner as in (1) above. To the culture medium were added human (100 U/ml, 20 ng/ml), human IL-2 (400 U/ml, 8 ng/ml) or T-cell factor (10%). On the 4th day of the cultivation, the cells were recovered and the cells producing anti-SRBC antibody were enumerated directly according to the PFC method.

As shown in the Table 7, by the treatment with hydrocortisone the production of antibody against the antigen sensitized in vivo was suppressed about 60%. The spleen cells thus treated were cultured in the presence of lymphokine and SRBC for 4 days. The comparison of the spleen cells of the mouse treated with hydrocortisone and the spleen cells of the mouse without treatment with hydrocortisone shows that the suppressing effect of hydrocortisone is remarkably reduced (by about 20%) in the spleen cells of the mouse treated with human Ala-BCDF. There was not observed statistically significant effect of the hydrocortisone in the spleen cells treated either with TF or with human IL-2, as compared with the control.

The enhanced productivity of the antibody by the use of BCDF in the mouse administered with hydrocortisone demonstrates that immunity and host defense mechanism are effectively activated by the BCDF, under immunosuppresive condition.

TABLE 7

| Treatment | PFC/1 × 10⁶ spleen cells | Suppression by HC treatment |
|---|---|---|
| Balb/c SRBC(−) | 1 | |
| SRBC(+) | 104 | 0% |
| SRBC(+) HC treatment | 42 | 60% |

[Lymphokine treatment in vitro PFC]

| Treatment | in vitro SRBC | lymphokine | PFC/1 × 10⁶ spleen cells | Suppression by HC treatment |
|---|---|---|---|---|
| HC untreated | − | − | 27 | |
| SRBC administration | + | − | 290 | 0 |
| | + | TF | 750 | 0 |
| | + | human IL-2 | 133 | 0 |
| | + | human Ala-BCDF | 573 | 0 |
| | + | human IL-2 + human Ala-BCDF | 506 | 0 |
| HC 0.5 mg treatment | − | − | | 0 |
| SRBC administration | + | − | 83 | 71 |
| | + | TF | 276 | 63 |
| SRBC administration | + | human IL-2 | 43 | 67 |
| | + | human Ala-BCDF | 443 | 22 |
| | + | human IL-2 + human Ala-BCDF | 200 | 60 |

EXAMPLE 18

(Growth of bone marrow cells stimulated by human Ala-BCDF) Hematopoietic stimulating effect of human BCDF and of human Ala-BCDF was examined in the following procedures;

The thigh bone was removed from DBA/2 mouse (female, 8 weeks old), from which was prepared bone marrow cells under sterile condition in a conventional manner as described in "The Method of Immunological Experiment, P. 1305, Jap. Soc. Immunology". The bone marrow cells ($5 \times 10^4$) thus obtained were suspended in RPMI 1640 medium (100 µl) containing 10% FBS, to which was added 100 µl solution composed of serial dilutions (2 fold) of human Ala-BCDF (500 U/ml: 100 ng/ml), and of mouse IL-3 (5 U/ml, 1.25 U/ml). The suspension was cultured on a plate (96 well) (Corning 25860) at 37° C. in 5,% $CO_2$, and the effect on the (growth) of bone marrow cells was examined.

The mouse IL-3 was prepared in the following manner. Thus, plasmid in which mouse IL-3 cDNA (See Nature 307, 233 (1984)) had been integrated into pQ vector (See: Japanese Patent Application No. 184858/1986) was transfected into COS cells in a conventional manner as described in Proc. Natl. Acad. Sci, USA 81, 1070 (1984)) and the COS cells were cultured for 3 days. The supernatant separated from the culture (IL-3 activity; about 50 U/ml) was dialyzed against RPMI 1640 medium, which was served for the subsequent procedure. On the 4th day of cultivation, the culture of bone marrow cells was admixed with tritium labeled thymidine (3H-TdR) (1 µCi/well) and allowed to stand for 18 hours. The culture was filtered to collect the cells on which the 3H-TdR incorporated was assayed by means of a β-scintillation counter.

Figure 19:
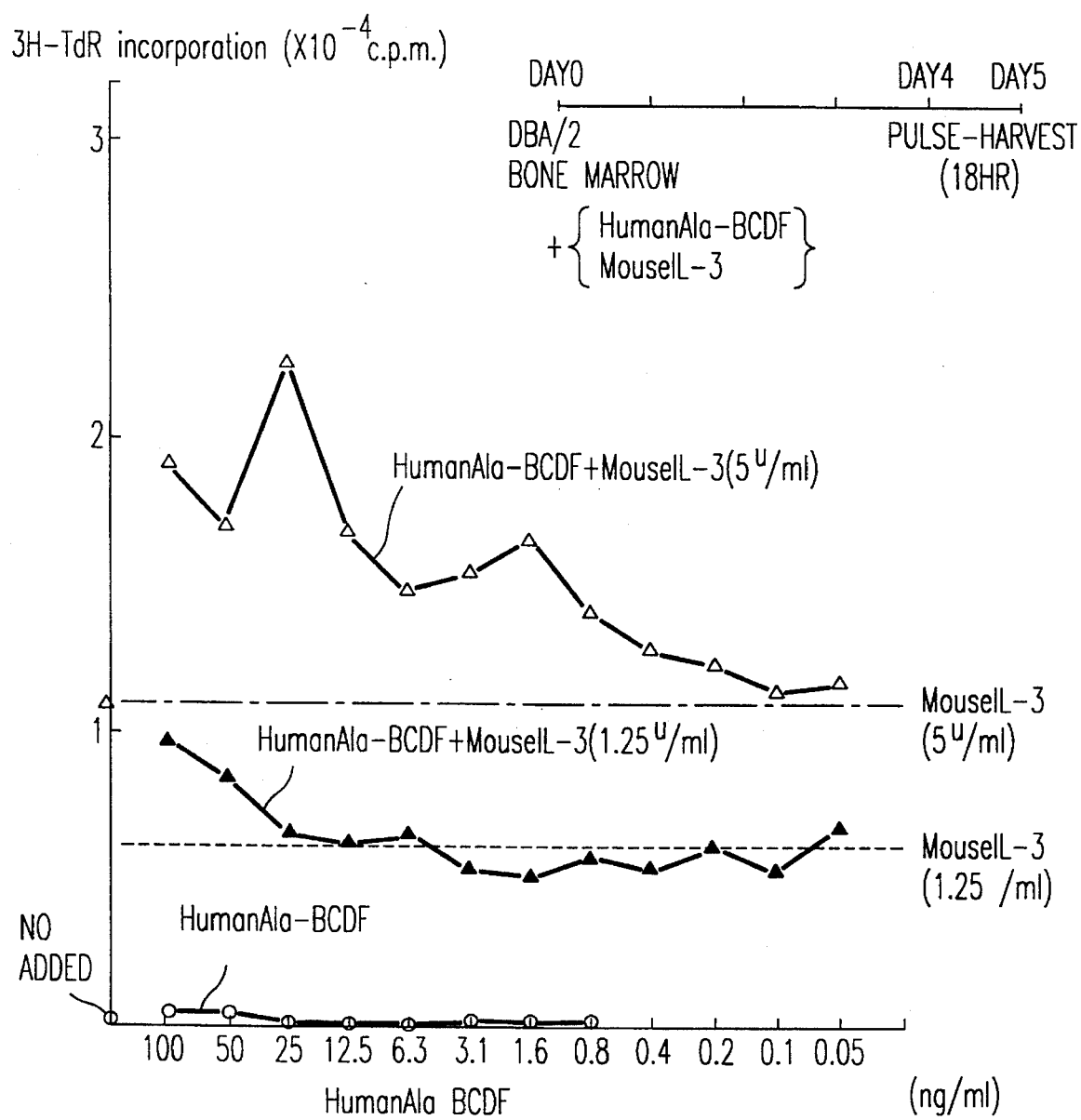
FIG. 19 illustrates that growth of DBA/2 mouse bone marrow cells is enhanced by the combined addition of human Ala-BCDF and mouse IL-3.

As shown in FIG. 19, the culture of bone marrow cells cultured with human Ala-BCDF exhibits an enhanced ³H-TdR incorporation of the bone marrow cells, as compared with the control. When human Ala-BCDF was added in combination with bone marrow cell growth factor (mouse IL-3), the growth of the bone marrow cells was further enhanced.

The same phenomenon was also observed for other strains of mice, such as Balb/c, c57B1/6 and C3H/HeN.

EXAMPLE 19

Lentinan (10 mg/kg) was injected intravenously into the tail of DAB/2 mouse (female, 8 weeks old). 10, 7 and 5 days after the injection, bone marrow was removed from the mouse, and the bone marrow cells were prepared according to the method as described in example 18 above.

Bone marrow cells were cultured in the presence of human Ala-BCDF(50 U/ml; 10 ng/ml) and mouse IL-3 (5 U/ml). The effect of BCDF on the growth of the cells was examined in the culture. Thus, on 3, 4 and 5 the days of the cultivation, the culture was admixed with 3H-TdR (1 µCi/well). The growth of the bone marrow cells were assessed based on the incorporation of 3H-TdR into the cells according to the method described in example 18 above.

Thus, lentinan was administered to a female DBA/2 mouse. 10, 7 and 5 days after the administration, the DBA/2 mouse treated and the one which was not administered with lentinan were treated in the same manner to prepare bone marrow cells. To the bone marrow cells was added BCDF (50 ng/ml) and IL-3 (5 U/ml). The rate of growth was assessed on the basis of the incorporation of 3H-TdR on the 3, 4 and 5 day after the addition of BCDF and IL-3. LNT means lentinan.

Figure 20:
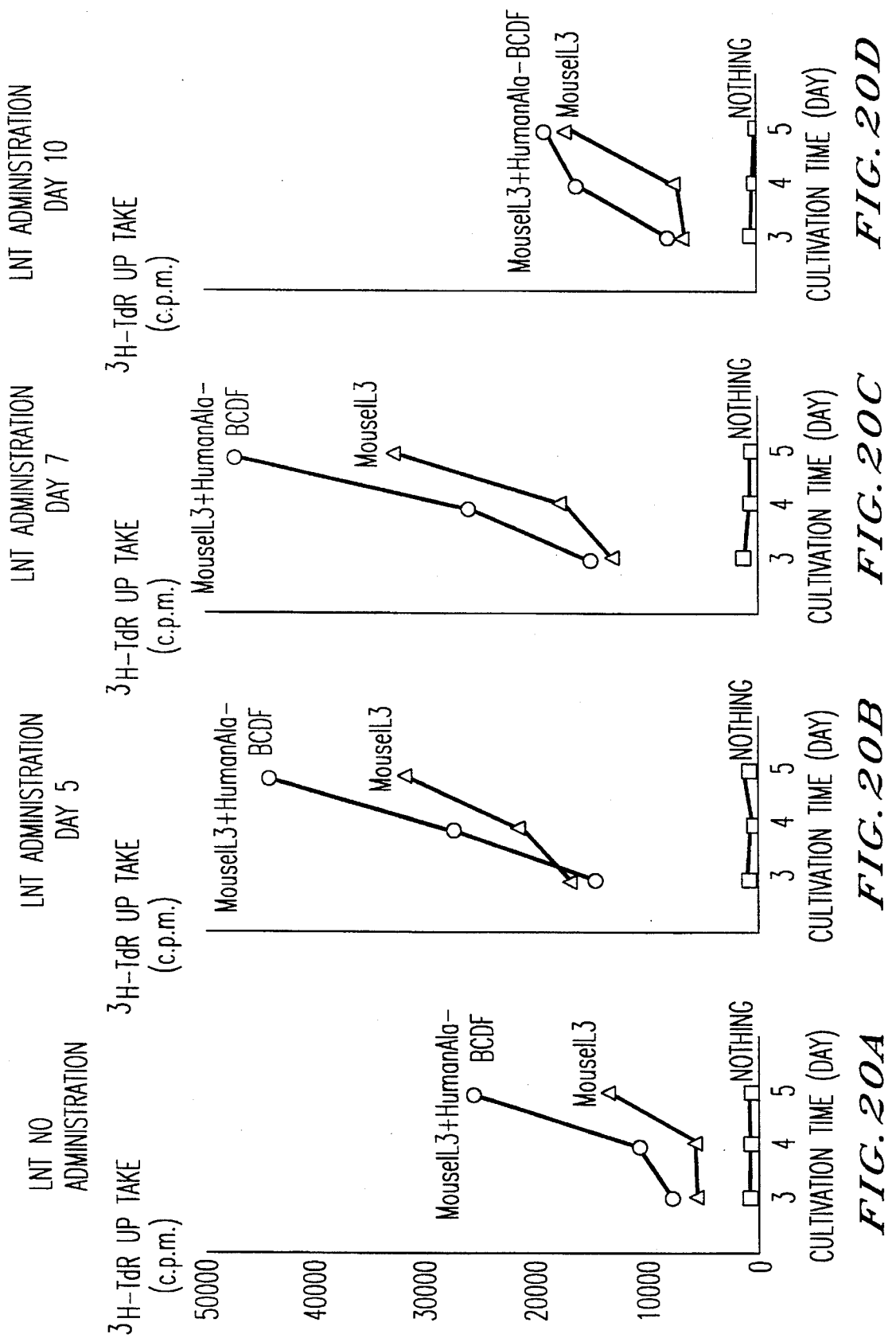
FIG. 20 illustrates that growth of bone marrow cells which have been induced by the combined addition of human Ala-BCDF and mouse IL-3 is further enhanced by the previous administration of lentinan.

As shown in FIG. 20, in the bone marrow cells of the mouse administered with lentinan 5 or 7 days before the removal of the bone marrow, the growth was enhanced by the combined application of human Ala-BCDF and mouse IL-3, as compared with control.

EXAMPLE 20

Bone marrow cells were prepared from DBA/2 mouse (female, 8 weeks old) according to the method as described in example 18 above. Colony forming activity was determined by the use of the assay system as described below. Thus, DMEM medium as concentrated 2 folds) containing (20%) FBS, ($5 \times 10^5$) 2-mercaptoethanol was admixed with (1%) agar solution, heated to melt agar in the water-bath in a ratio of 7:3. The bone marrow cells ($7.5 \times 10^4$) mentioned above was suspended in the aqueous agar medium as prepared above, and the suspension was semi-solidified in a 3.5 cm schale (Falcon 1008). The agar suspension was cultured at 37° C. in 5% $CO_2$ for 7 days to develop colonies (more than 50 cells) cells and clusters (consisting of 8 to 50 cells). The number of colonies and clusters were enumerated microscopically.

The agar suspension medium was admixed with human Ala-BCDF (50 to 500 U/ml; 10 to 100 ng/ml) and mouse IL-3 (1.25 U/ml) and cultured. For this culture, was examined the formation of colonies and clusters.

Figure 21:
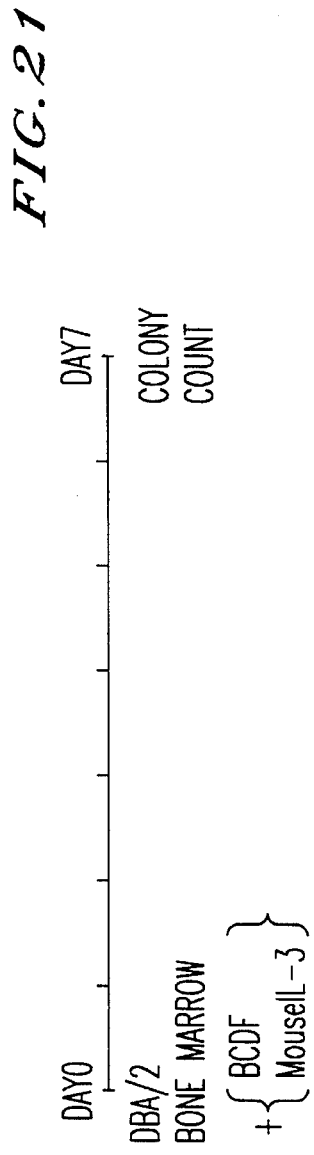
FIG. 21 illustrates that human Ala-BCDF and mouse IL-3 stimulate the formation of colonies and clusters of DBA/2 mouse bone marrow cells.

As shown in FIG. 21, the agar suspension medium added with human Ala-BCDF exhibits a statistically significant increase in the number of clusters, as compared with the control. FIG. 21 also shows that the colony formation induced by mouse IL-3 is further enhanced by the addition of BCDF.

The same phenomenon was observed in the immunosuppressed mouse induced by the application of immunosuppressing agent, hydrocortisone. Thus, hydrocortisone (1 mg to 5 mg) was injected subcutaneously to DBA/2 mouse marrow (female, 6 weeks old). 5 days after, bone marrow cells were prepared in the same manner as described above.

Figure 22:
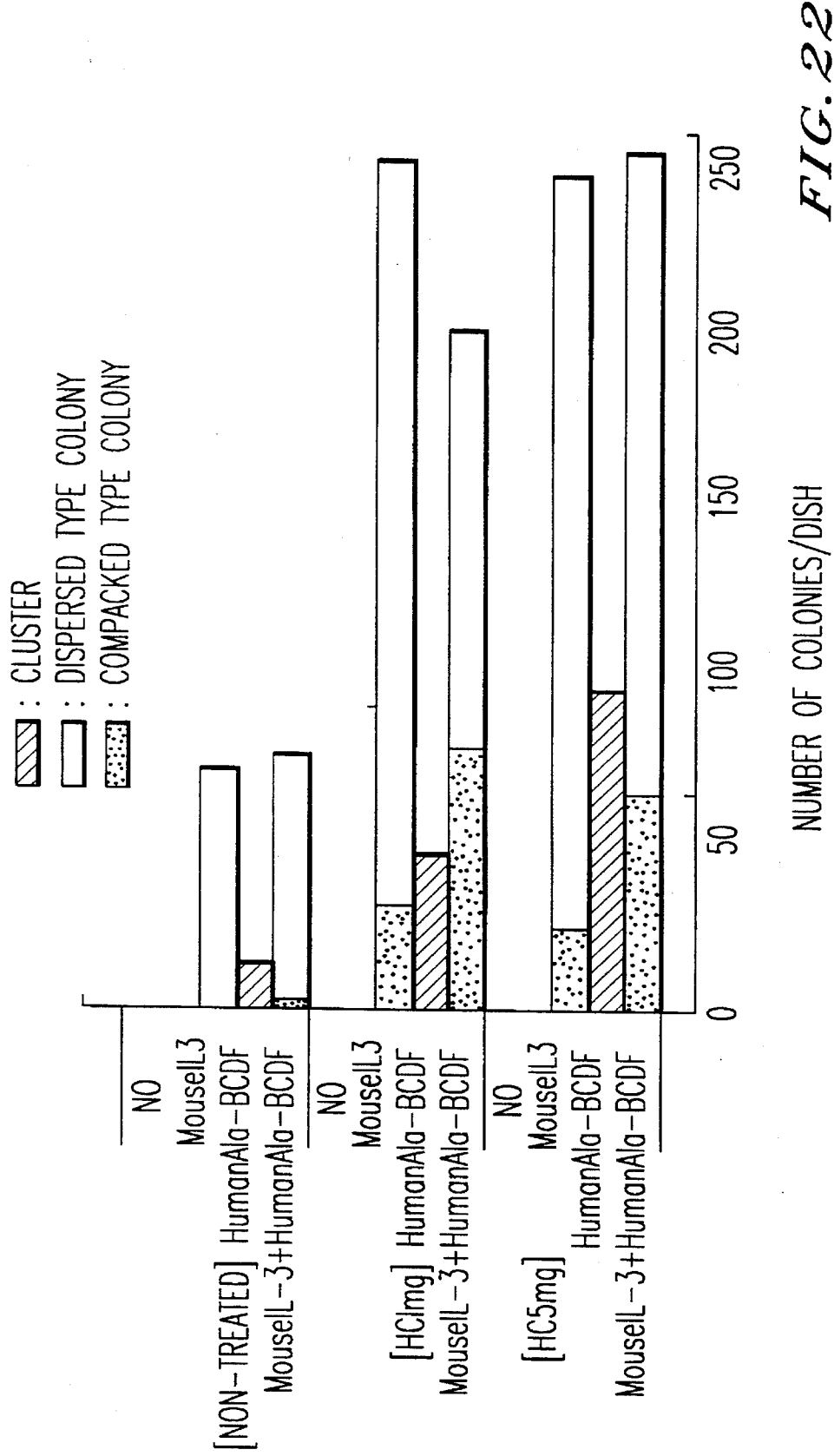
FIG. 22 illustrates that the formation of colonies and clusters of bone marrow cells from an immuno-deficient mouse (induced by administration of immuno-suppressive agent) are enhanced by the combined addition of human Ala-BCDF and mouse IL-3.

Human Ala-BCDF (200 ng/ml, 1000 U/ml), mouse IL-3 (0.6 U/ml) were added to DMEM medium containing (1%) methylcellulose (20%) FBS and ($5 \times 10^5$ M) 2-methylmercaptoethanol. To the medium thus prepared was added bone marrow cells ($2 \times 10^4$), and cultured for 7 days to develop colonies. As shown in FIG. 22, the formation of clusters was enhanced significantly by the addition of human Ala-BCDF. By the administration of hydrocortisone, the colony-forming ability itself was increased, and the formation of macrophage lymphocyte like colonies was remarkably enhanced by the addition of human Ala-BCDF in combination with mouse IL-3.

Therefore, it was confirmed that BCDF applied either singly or in combination with IL-3 stimulates hematopoietic function in immunosuppressed mice.

EXAMPLE 21

It was examined whether human BCDF or human Ala-BCDF can differentiate tumor cells and exhibit an antitumor activity.

Figure 23:
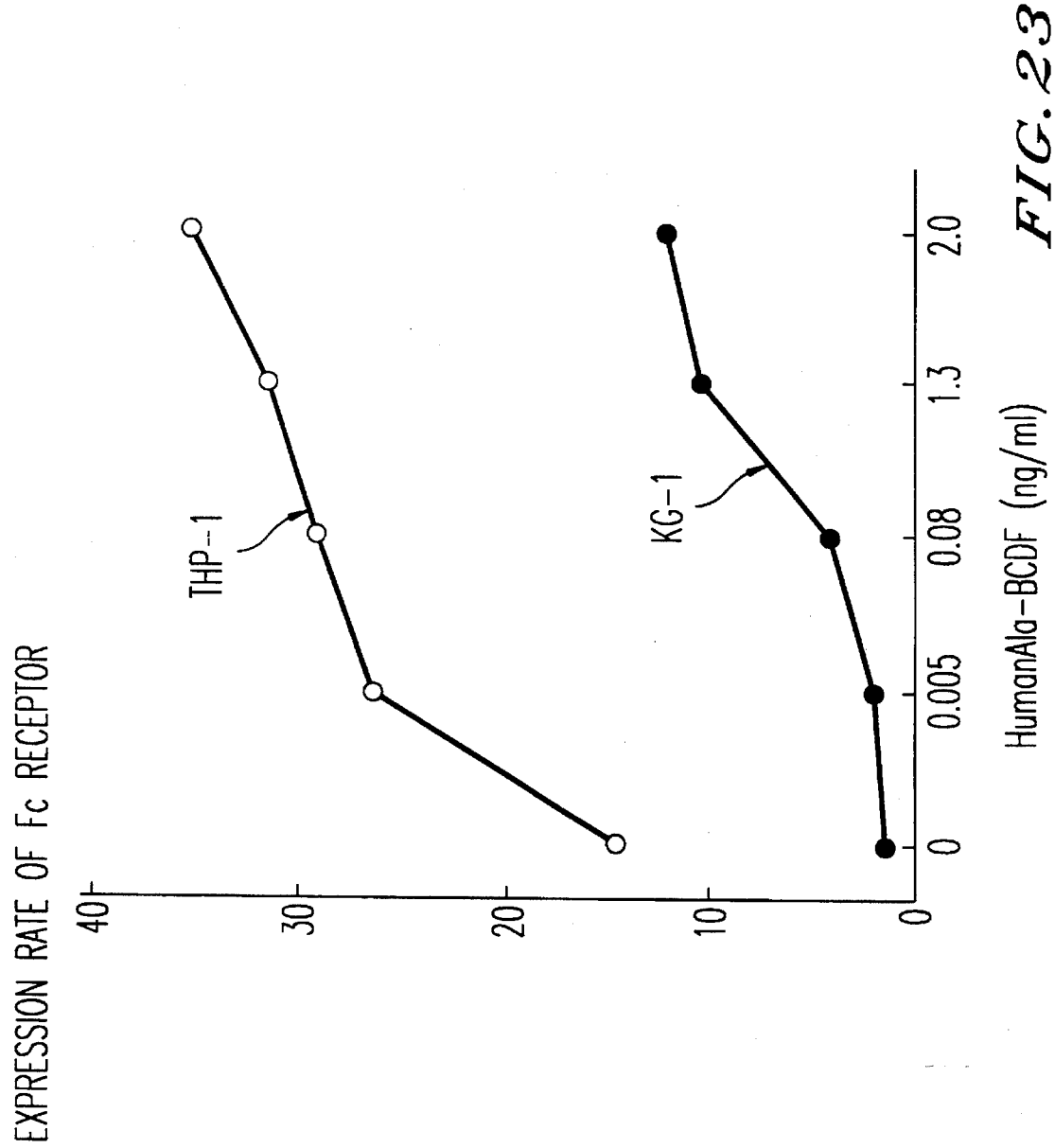
FIG. 23 illustrates that human Ala-BCDF induces the differentiation of human myelomonocytic leukemia cell lines.

The test was conducted as follows:

Human myelomonocitic leukemia cell line THP-1 and KG-1 (each $2 \times 10^5$/ml) was suspended in RPMI 1640 medium containing (10%) FBS. The suspension of cell were added in an amount of 1 ml/well onto a plate (Corning Co., 25820), and cultured at 37° C. in $CO_2$ (5%) for 2 days. To the culture was added human Ala-BCDF (20 ng/ml to 5 pg/ml) and the effect of the addition of the human Ala-BCDF on the differentiation of the tumor cells was examined. Thus, the frequency of occurrence of FC receptors in tumor cells on the 2nd day of the culture was determined by rosette formation method (See: Cancer Research, 44, 5127 (1984)) using sensitized ox red blood cells. The value of the frequency of occurrence was used as the index of differentiation. FIG. 23 shows frequency of occurrence of Fc receptors as measured for the culture of THP-1, KG-1 which were cultured in a medium containing RPMI 1640 (2 $10^5$/ml) and FBS (10%) for 2 days. The frequency of occurrence was determined by rosette formation method using sensitized ox red blood cells. As shown in FIG. 23, human Ala-BCDF enhanced significantly the frequency of occurrence of Fc receptors in myelomonocytic leukemia cell lines, THP-1 and KG-1. Therefore it is apparent that BCDF can stimulate the differentiation of tumor cells into normal cells and BCDF exhibits anti-tumor activity.

EXAMPLE 22

Tonsils were obtained from patients who had undergone tonsillectomy. Tonsils were teased in RPMI-1640, after removal of the debris and mononuclear cells were separated by centrifugation on LSM (Ficoll-sodium diatrizoate) solution at 400×G for 30 min.

Tonsil mononuclear cells ($1 \rightarrow 2 \times 10^5$/200 μl RPMI 1640+ 10% FBS/well) were stimulated with several concentrations of PWM (pokeweed mitogen) and various concentration of BCDF. After day 7 incubation, the concentration of IgM, IgG and IgA in culture supernatants were quantitated by a sandwich enzyme-linked immunosorbent assay(ELISA).

Figure 24:
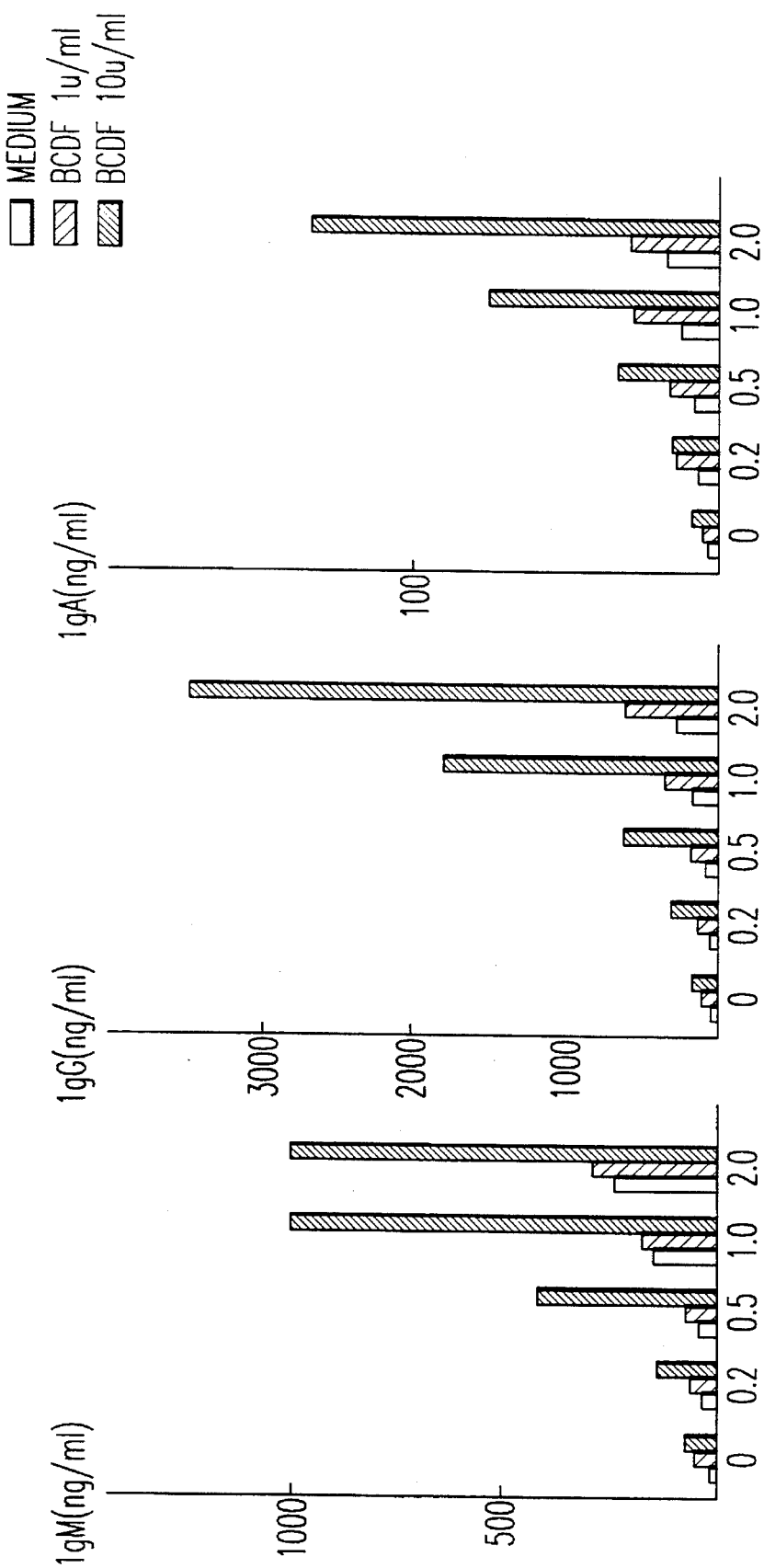
FIG. 24 indicates that recombinant BCDF induces Ig secretion of PWM-stimulated mononuclear cells.

The result showed that BCDF increased the production of various antibodies (FIG. 24).

EXAMPLE 23

Tonsils were obtained from patients who had undergone tonsillectomy. Tonsils were teased in RPMI-1640, after removal of the debris, and mononuclear cells were separated by centrifugation on LSM (Ficoll-sodium diatrizoate) solution at 400×G for 30 min.

T and B cells were separated by rosette method with neuramidase-treated sheep red blood cell.

The E-rosette-negative fraction was treated with appropriately diluted anti-Leu-1 for 30 min. on ice. Treated cells were incubated with newborn rabbits sera used as a complement. B cell blasts activated with PWM at 0.25% plus irradiated T cells were used.

B cell blasts ($5 \times 10^4 \rightarrow 1 \times 10^5$/200 μl RPMI 1640+ 10% FBS/well) were cultured with various concentrations of BCDF for 5 days.

The concentrations of IgG in culture supernatants were quantitated by a sandwich enzyme-linked immunosorbent assay (ELISA).

Figure 25:
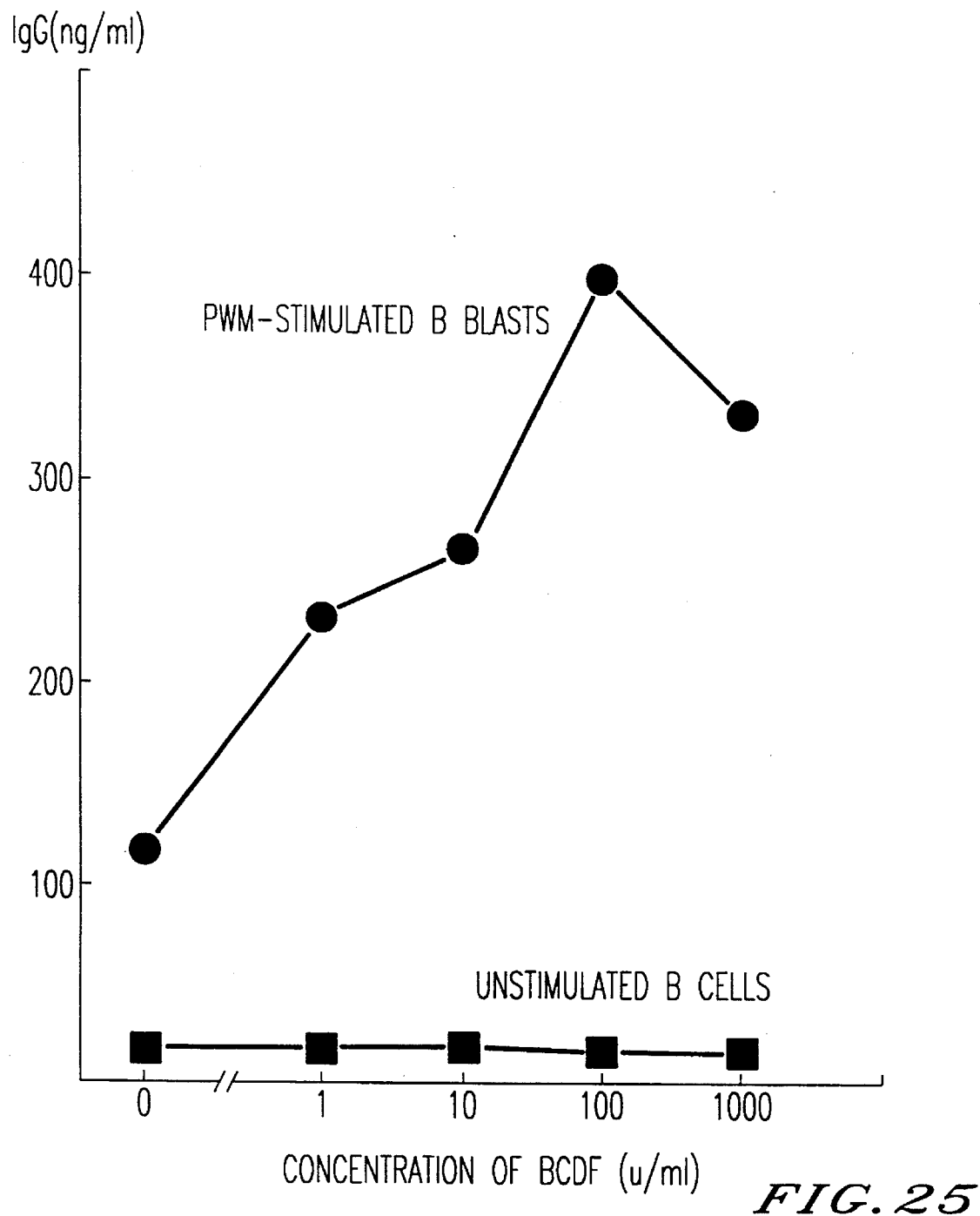
FIG. 25 indicates that recombinant BCDF induces Ig secretion of PWM-stimulated B blast cells.

The result showed that recombinant BSF-2 induced Ig secretion in PWM-stimulated B blast cells (FIG. 25).

EXAMPLE 24

SRBC was administered intravenously in vivo to C3H/Hej mice of 6 week age in a dose of $1 \times 10^8$/head and the spleen cells were isolated 5 days after. The spleen cells ($5 \times 10^5$/well) and SRBC ($1 \times 10^5$/well) were incubated for 4 days together with BCDF in the aforesaid concentration. After completion of the incubation, the cells were recovered and the count of SRBC-specified antibody-producing cells was measured by PFC method using a Cunningham chamber.

Figure 26:
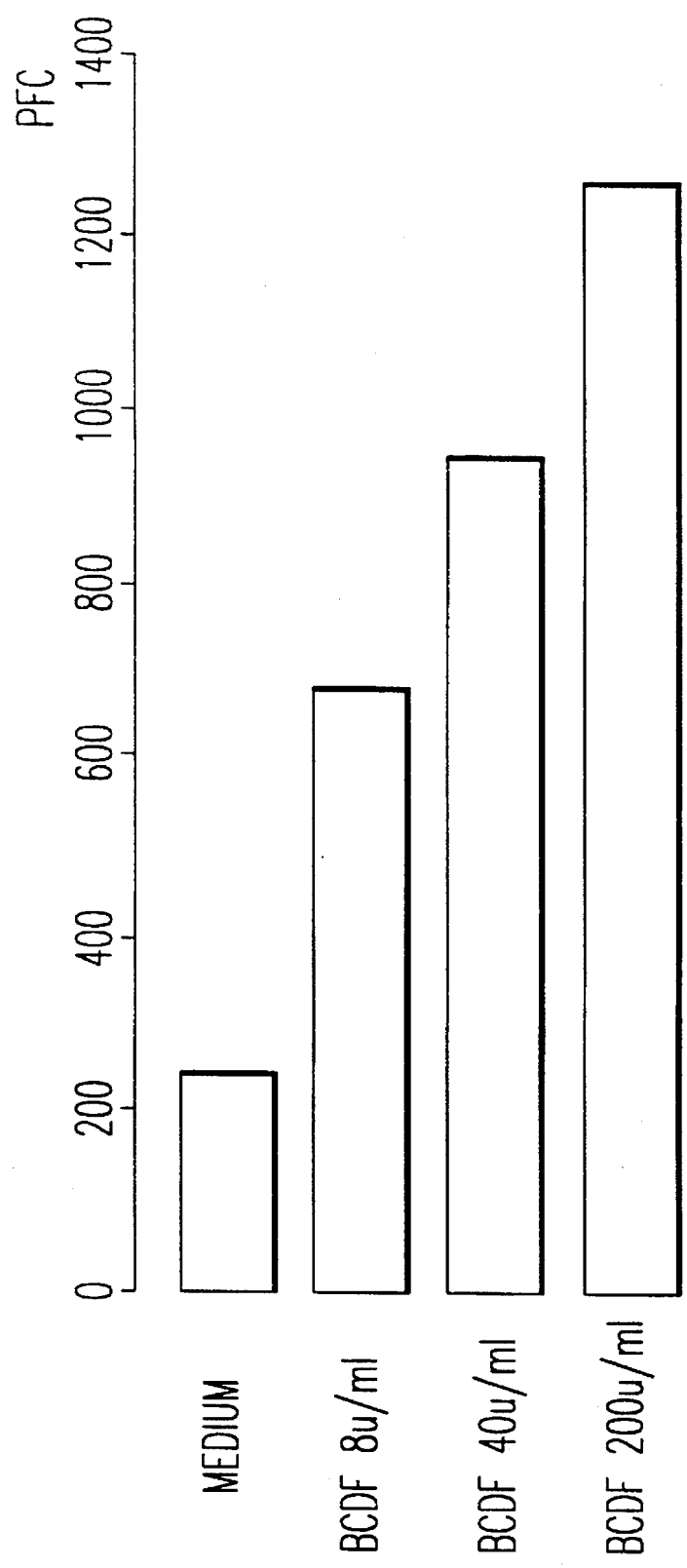
FIG. 26 indicates an increase of SRBC-specific antibody-producing cell numbers of the C3H/HeJ (LPS Low Responder Mouse) spleen cells by the addition of BCDF.

As shown in FIG. 26, BCDF augmented production of the SRBC-specific antibody-producing cells from the SRBC-sensitized spleen cells singly.

EXAMPLE 25

5FU was administered intravenously to DBA/2 mice in a dose of 0.5 mg/head for consecutive 3 days and SRBC was administered intravenously in vivo on Day 3 in a dose of $1 \times 10^8$/head. BCDF was subcutaneously given for 3 consecutive days from 2 days after the administration of SRBC in a dose of 0.01 to 1.0 μg/head. Sera were subjected to sampling 5 days after the administration of SRBC. The concentration of SRBC-specific antibody in serum was measured by a SRBC agglutination test using a 96 well microplate. As an agglutination titer, the reciprocal number of dilution magnification was used.

Figure 27:
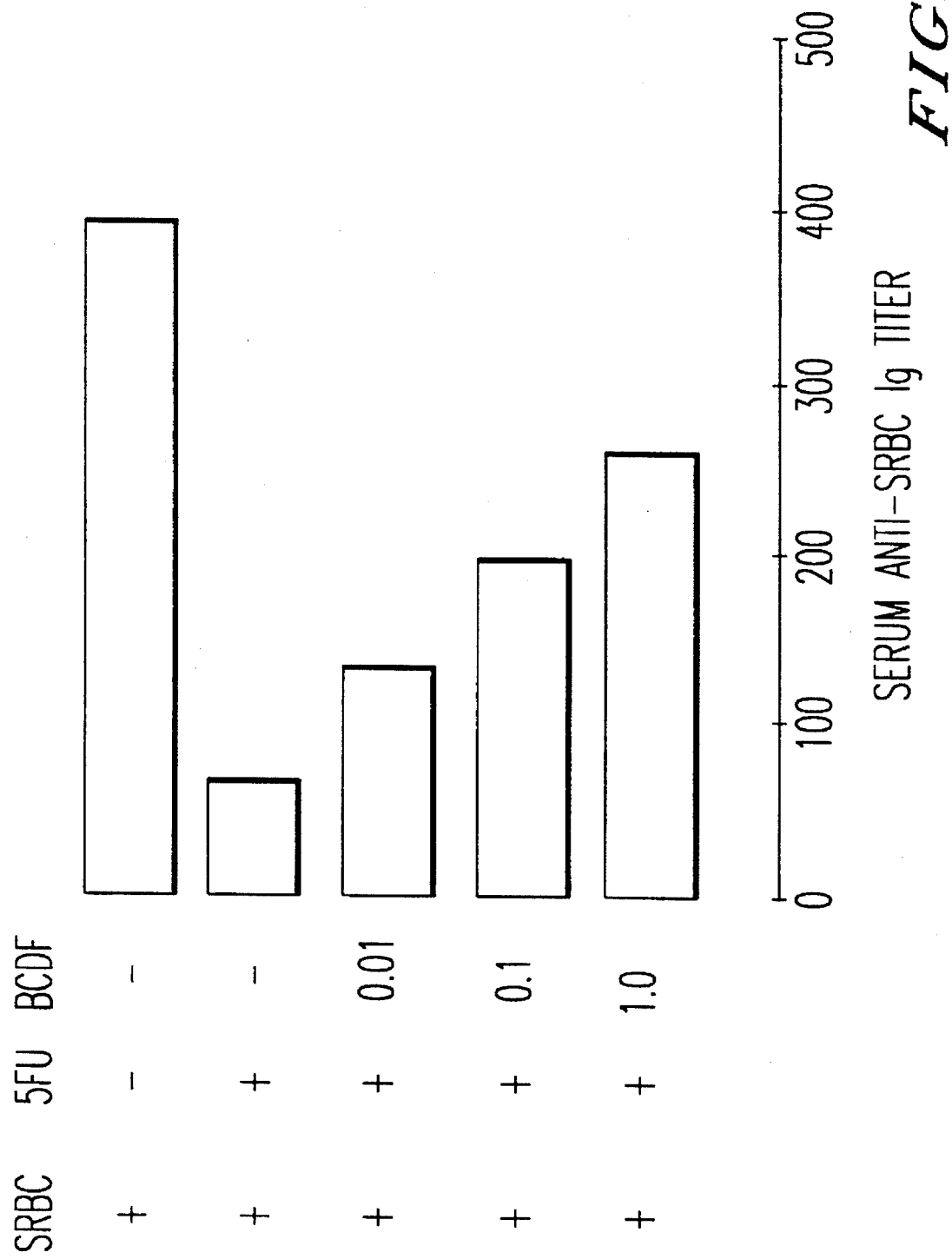
FIG. 27 indicates an increase of anti-SRBC Ig titer in serum by administration of BCDF in vivo.

As shown in FIG. 27, the administratin of BCDF accelerated in a dose dependent manner antibody productivity reduced by the administration of 5-FU.

EXAMPLE 26

Figure 28:
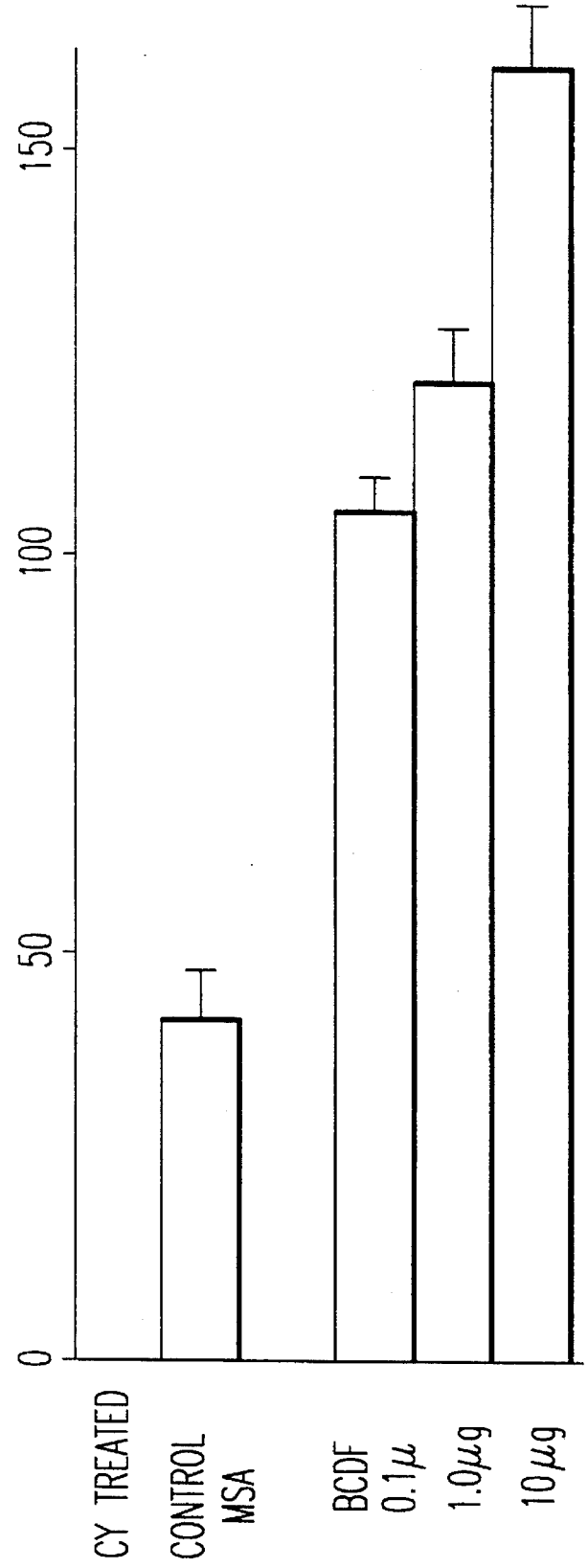
FIG. 28 indicates an augmentation of splenic hematopoiesis by administration of BCDF in vivo.

Cyclophosphamide (CY) was intraperitoneally administered to DBA/2 mice of 6 weeks age in a dose of 4 mg/head (day 0). BCDF was then administered subcutaneously and intraperitoneally every day (day 0-day 6). On Day 7 after the CY administration, the spleen cells were isolated and $7.5 \times 10^4$ of the cells were incubated in a soft agar medium for 6 days together with 10% PWM-stimulated spleen cell supernatant. Thus the number of clusters was measured. For control, mouse serum albumin (MSA) was administered. The results are shown in FIG. 28.

The number of the clusters from spleen cells formed by the addition of PWM-stimulated spleen cell supernatant increased depending upon the dose of BCDF and reached 4 times at the maximum in the group administered with BCDF, as compared to the group administered with MSA.

It is assumed that the in vivo administration of BCDF would stimulate the growth of hematopoietic stem cells in the spleen.

Many modifications and variations of the present invention are possible in light of the above teachings. Therefore, it is to be understood that within the scope of the appended claims, the invention may be practiced otherwise than as specifically described.

What is claimed as new and desired to be secured by letters patent of the United States is:

1. A method for producing a purified nonglycosylated polypeptide which stimulates production of IgM in human B-cell line CL4 comprising:

culturing *Escherichia coli* transformed by a recombinant DNA comprising a gene coding for a polypeptide having amino acid sequence (I) in a medium and collecting a polypeptide having amino acid sequence (I); wherein amino acid sequence (I) is:

---

PRO VAL PRO PRO GLY GLU ASP SER LYS ASP VAL
ALA ALA PRO HIS ARG GLN PRO LEU THR SER SER
GLU ARG ILE ASP LYS GLN ILE ARG TYR ILE LEU
ASP GLY ILE SER ALA LEU ARG LYS GLU THR CYS
ASN LYS SER ASN MET CYS GLU SER SER LYS GLU
ALA LEU ALA GLU ASN ASN LEU ASN LEU PRO LYS
MET ALA GLU LYS ASP GLY CYS PHE GLN SER GLY
PHE ASN GLU GLU THR CYS LEU VAL LYS ILE ILE
THR GLY LEU LEU GLU PHE GLU VAL TYR LEU GLU
TYR LEU GLN ASN ARG PHE GLU SER SER GLU GLU
GLN ALA ARG ALA VAL GLN MET SER THR LYS VAL
LEU ILE GLN PHE LEU GLN LYS LYS ALA LYS ASN
LEU ASP ALA ILE THR THR PRO ASP PRO THR THR
ASN ALA SER LEU LEU THR LYS LEU GLN ALA GLN
ASN GLN TRP LEU GLN ASP MET THR THR HIS LEU
ILE LEU ARG SER PHE LYS GLU PHE LEU GLN SER
SER LEU ARG ALA LEU ARG GLN MET

---

\* \* \* \* \*

UNITED STATES PATENT AND TRADEMARK OFFICE
CERTIFICATE OF CORRECTION

PATENT NO. : 5,541,088　　　　　　　　　　Page 1 of 2
DATED : July 30, 1996
INVENTOR(S) : Tadamitsu KISHIMOTO, et al.

It is certified that error appears in the above-identified patent and that said Letters Patent is hereby corrected as shown below:

Title page, item [54], & Column 1, line 3, "DEFFERENTIATION FACTOR" should read --DIFFERENTIATION FACTOR--.

Column 3, line 18, underline "*in vivo*";
　　　　line 48, underline "*in vivo*";
　　　　line 50, underline "*in vivo*".

Column 4, line 36, delete the period (.) in front of "notable".

Column 9, line 43, "haemopoietic" should read --hemopoietic--.

Column 14, line 62, "weight of $3.5 + 0.5 \times 10^4$" should read --weight of $3.5 \pm 0.5 \times 10^4$--.

Column 20, line 24, "follows by treatment" should read --followed by treatment--;
　　　　line 54, "into medium" should read --into Ψ medium--.

UNITED STATES PATENT AND TRADEMARK OFFICE
CERTIFICATE OF CORRECTION

PATENT NO. : 5,541,088
DATED : July 30, 1996
INVENTOR(S) : Tadamitsu KISHIMOTO, et al.

It is certified that error appears in the above-identified patent and that said Letters Patent is hereby corrected as shown below:

Column 21, line 4, "(100l)" should read --(100 $\mu l$)--;
      line 26, "hybrization" should read --hydridization--.

Column 22, line 47, "(50$\mu$)" should read --(50$\mu l$)--.
      line 52, "(150 M)" should read --(150$\mu M$)--.

Column 24, line 65, "ws introduced" should read --was introduced--.

Column 25, line 61, "$CaC_2$" should read --$CaCl_2$--.

Column 31, line 60, delete "for" after "The".

Column 35, line 56, "5,% $CO_2$" should read --5% $CO_2$--.

Signed and Sealed this

Third Day of March, 1998

*Attest:*

BRUCE LEHMAN

*Attesting Officer*      *Commissioner of Patents and Trademarks*